United States Patent
Klefenz

(10) Patent No.: US 8,189,834 B2
(45) Date of Patent: May 29, 2012

(54) DEVICE AND METHOD FOR GENERATING A FILTERED ACTIVITY PATTERN, SOURCE DIVIDER, METHOD FOR GENERATING A DEBUGGED AUDIO SIGNAL AND COMPUTER PROGRAM

(75) Inventor: Frank Klefenz, Mannheim (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 792 days.

(21) Appl. No.: 12/305,661

(22) PCT Filed: Jun. 26, 2007

(86) PCT No.: PCT/EP2007/005649
§ 371 (c)(1),
(2), (4) Date: Dec. 19, 2008

(87) PCT Pub. No.: WO2008/000444
PCT Pub. Date: Jan. 3, 2008

(65) Prior Publication Data
US 2010/0232631 A1   Sep. 16, 2010

(30) Foreign Application Priority Data
Jun. 30, 2006   (DE) .......................... 10 2006 030 276

(51) Int. Cl.
*H04R 25/00* (2006.01)
(52) U.S. Cl. ....................................... 381/313; 381/312
(58) Field of Classification Search .................. 381/312, 381/313
See application file for complete search history.

(56) References Cited

U.S. PATENT DOCUMENTS

| | | | |
|---|---|---|---|
| 5,434,924 A | 7/1995 | Jampolsky |
| 6,442,510 B1 | 8/2002 | Klefenz |
| 6,987,856 B1 | 1/2006 | Feng et al. |
| 7,043,684 B2 | 5/2006 | Joly |
| 2002/0012438 A1 | 1/2002 | Leysieffer et al. |
| 2003/0115054 A1 | 6/2003 | Iso-Sipila |
| 2003/0171786 A1 | 9/2003 | Blamey et al. |

(Continued)

FOREIGN PATENT DOCUMENTS

DE   10 2005 030 326 A1   1/2007

(Continued)

OTHER PUBLICATIONS

Baumarte, "A Physiological Ear Model for the Emulation of Masking", Journal for Oto-Rhino-Laryngology, Sep.-Oct. 1999, pp. 294-304.

(Continued)

*Primary Examiner* — Kenneth Parker
*Assistant Examiner* — John Lin
(74) *Attorney, Agent, or Firm* — Keating & Bennett, LLP

(57) ABSTRACT

A device for generating a filtered activity pattern based on a first activity pattern at an auditory model of a first ear and a second activity pattern at an auditory model of a second ear includes an identifier for identifying a first trajectory in the first activity pattern and a second trajectory in the second activity pattern which are associated with the same sound event. The device further includes a determiner for determining whether the two trajectories are associated with a sound event of a useful sound source. The device further includes a filter for filtering the first activity pattern or the second activity pattern based on a result of determining whether a trajectory is associated with a sound event of the useful sound source.

51 Claims, 22 Drawing Sheets

U.S. PATENT DOCUMENTS

| | | |
|---|---|---|
| 2005/0069162 A1 | 3/2005 | Haykin et al. |
| 2005/0177205 A1 | 8/2005 | Kwon et al. |
| 2005/0192646 A1 | 9/2005 | Grayden et al. |
| 2007/0005348 A1 | 1/2007 | Klefenz |

FOREIGN PATENT DOCUMENTS

| | | |
|---|---|---|
| DE | 10 2005 030 327 A1 | 1/2007 |
| WO | 2006/002748 A1 | 1/2006 |

OTHER PUBLICATIONS

Zwicker, "A Hardware Cochlear Nonlinear Preprocessing Model with Active Feedback", The Journal of the Acoustical Society of America, vol. 80., Jul. 1986, pp. 146-153.

Zwicker et al., "Cochlear Preprocessing in Analog Models, in Digital Models and in Human Inner Ear", Hearing Research, vol. 44, issues 2-3, Mar. 1990, pp. 209-216.

Official communication issued in counterpart International Application No. PCT/EP2007/005649, mailed on Jun. 30, 2006.

Szepannek et al.: "Vowel Classification by a Perceptually Motivated Neurophysiologically Parameterized Auditory Model," Studies in Classification, Data Analysis, and Knowledge Organization; Mar. 2006; pp. 1-8.

Harczos: "A Revised Neurobiologically Parameterized Model of the Cochlea and an Attached Auditory Image Processing Network," PPCU Multidisciplinary Doctoral School; 2005-2006; pp. 1-4.

Harczos et al.: "A Neurobiologically Inspired Vowel Recognizer Using Hough-Transform: A Novel Approach to Auditory Image Processing," Institute for Systems and Technologies of Information, Control and Communications; Feb. 2006; pp. 251-256.

Klefenz: "Device, Method, and Computer Program for Analyzing an Audio Signal," U.S. Appl. No. 11/172,605, filed Jun. 29, 2005.

Klefenz et al.: "Device, Method, and Computer Program for Analyzing an Audio Signal," U.S. Appl. No. 11/944,170, filed Dec. 28, 2007.

English translation of the International Patent Application No. PCT/EP2006/004399; filed on May 10, 2006.

DEVICE AND METHOD FOR GENERATING A FILTERED ACTIVITY PATTERN, SOURCE DIVIDER, METHOD FOR GENERATING A DEBUGGED AUDIO SIGNAL AND COMPUTER PROGRAM

BACKGROUND OF THE INVENTION

The present invention generally relates to a device and a method for generating a filtered activity pattern, to a source divider, to a method for generating a debugged audio signal and to a computer program, in particular to a concept for noise source filtering.

In the field of today's medical technology, it is an important challenge to enable persons with impaired hearing to participate in normal life. For this purpose, from medical technology a great number of different hearing aids are known. It is a special challenge if the inner ear of a patient is damaged. In this case it is necessary to directly excite the auditory nerves of the patient.

Although this may already be successfully achieved with the help of cochlear implants, patients having cochlear implants still have special difficulties when they are close to several different sound sources. In this case, among other things speech intelligibility clearly decreases.

For this reason there is a need to improve the hearing impression of patients with a cochlear implant in particular in situations in which several sound sources are present.

In the following, some documents are discussed which provide background information regarding the mentioned problems.

The article "A revised neurobiologically parameterized model of the cochlea and an attached auditory image processing network" by T. Harczos (a doctorate student in his second year) and his tutor Dr. T. Roska (PPCU Multidisciplinary Doctoral School, 2005-2006 annual report) describes a neurobiologically parameterized model of the cochlea. In the described model, a basilar membrane modeling is used according to an extended Zwicker/Baumgarte model. Further, an inner hair cell is replicated using the model by Meddis, by which a vesicle release is calculated. Further, additionally the synaptic cleft is modeled, and further also processes after the synaptic cleft are modeled.

Further information with regard to a processing of sound data using a Hough transformation are, for example, found in the article "A neurobiologically inspired vowel recognizer using Hough-transform" by T. Harczos, F. Klefenz and A. Kátai (published in the Proceedings VISAPP 2006, Setubal, Portugal, 25-28 Feb. 2006).

The main contribution SCHALLANALYSE with the title "Neuronale Repräsentation des Hörvorgangs als Basis" by G. Szepannek, F. Klefenz and C. Weihs, published online on 28 Sep. 2005, Informatik-Spektrum, Springer-Verlag GmbH, ISSN: 0170-6012 (Paper), describes a modeling of the response of an auditory nerve and an information extraction.

Further information is found in the article "Feature Extraction for sound classification by means of a perceptionally motivated neurophysiologic parameterized auditory model" by T. Harczos, A. Katai, F. Klefenz, P. Schikowski and G. Szepannek (published at the conference of the Gesellschaft für Klassifikation GfKl 2006 from 8 Mar. to 10 Mar. 2006 in Berlin.

Further, the non-prepublished German patent application with the official file number 10 2005 030 326 discloses a concept for analyzing an audio signal. The mentioned patent application, to which, moreover, an international subsequent application with the file number PCT/EP 2005/006315 exists, describes a method and a computer program for analyzing an audio signal to obtain an analysis representation of the audio signal. Further, the mentioned document describes a concept for the neurophysiologically parameterized simulation of the first stages of the auditory system. The teachings and definitions of DE 10 2005 030 326 and PCT/EP 2005/006315 are included by reference herein.

Similarly, the German patent application with the official file number 10 2005 030 327 describes the use of a neurophysiological auditory model and the generation of signals based thereon. With regard to the mentioned document, a parallel US application exists with the official file Ser. No. 11/172,605. The teachings and definitions of the two last mentioned documents are incorporated herein by reference.

Apart from that, U.S. Pat. No. 6,442,510 B1 describes a concept for determining a run-time differential for signal wave forms for a real-time pattern recognition, localization and monitoring of optical and acoustic signals. The mentioned concept includes steps of a segment-wise detection and a bringing into coincidence of signal wave forms for a conversion into monotonous and continuous trajectories for real-time pattern recognition and for the localization and monitoring of optical and acoustic signals. The method described in the mentioned document determines run-time differentials, wherein pre-programmed key signals are detected by signal sampling. Data are corrected by the sampled signals and pairs of signal combinations of given signal run-time differentials are determined from the coincidence of the detected signals.

The device includes at least two receivers for generating sequences of digital values from incoming acoustic signals. The device further includes vector generators to form the digital values in input vectors, a signal detection unit arranged after each vector generator and comprising parallel, programmable signal flow chains and adder/comparator units. The adder/comparator units are arranged vertically to the signal flow chains at equidistant intervals. The device further includes a multi-coincidence unit consisting of two anti-parallel shift registers forming flip-flop chains, and of AND gates.

SUMMARY

According to an embodiment, a device for generating a filtered activity pattern based on a first activity pattern at an auditory model of a first ear and a second activity pattern at an auditory model of a second ear may have an identifier for identifying a first trajectory in a first activity pattern and a second trajectory in the second activity pattern, associated with the same sound event, a determiner for determining whether the two trajectories are associated with a sound event of a useful sound source, and a filter for filtering the first activity pattern or the second activity pattern based on a result of the determination whether a trajectory is associated with a sound event of the useful sound source, so that in a filtered activity pattern activity events dominate which are associated with a sound event of the useful sound source, or that the activity events not associated with a sound event of the useful sound source are no longer present in the filtered activity pattern, wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model, wherein the identifier is implemented to identify a first curved trajectory in the first activity pattern and a second curved trajectory in the second activity pattern as trajectories belonging to the same sound event, when the first trajectory and the second trajectory have the same curvature within a predetermined tolerance range, and when the first trajectory and the second trajectory occur within a predetermined maximum time range, wherein the identifier is implemented to determine a time shift between the two identified trajectories which are associated with the same sound event, and wherein the determiner is implemented to determine using the time shift whether the two identified trajectories which are associated with the same sound event are associated with a sound event of a useful sound source.

According to another embodiment, a source divider for generating a debugged audio signal based on an audio signal comprising at least two channels may have an activity pattern generator for generating a first activity pattern at an auditory model of a first ear based on a first channel of the audio signal and for generating a second activity pattern at an auditory model of a second ear based on a second channel of the audio signal, a device for generating a filtered activity pattern based on the first activity pattern and the second activity pattern for generating a filtered activity pattern based on a first activity pattern at an auditory model of a first ear and a second activity pattern at an auditory model of a second ear, having an identifier for identifying a first trajectory in a first activity pattern and a second trajectory in the second activity pattern, associated with the same sound event, a determiner for determining whether the two trajectories are associated with a sound event of a useful sound source, and a filter for filtering the first activity pattern or the second activity pattern based on a result of the determination whether a trajectory is associated with a sound event of the useful sound source, so that in a filtered activity pattern activity events dominate which are associated with a sound event of the useful sound source, or that the activity events not associated with a sound event of the useful sound source are no longer present in the filtered activity pattern, wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model, wherein the identifier is implemented to identify a first curved trajectory in the first activity pattern and a second curved trajectory in the second activity pattern as trajectories belonging to the same sound event, when the first trajectory and the second trajectory have the same curvature within a predetermined tolerance range, and when the first trajectory and the second trajectory occur within a predetermined maximum time range, wherein the identifier is implemented to determine a time shift between the two identified trajectories which are associated with the same sound event, and wherein the determiner is implemented to determine using the time shift whether the two identified trajectories which are associated with the same sound event are associated with a sound event of a useful sound source, and a synthesizer for converting the filtered activity pattern into a time illustration, a frequency illustration or a subband illustration to acquire the debugged audio signal.

According to another embodiment, a method for generating a filtered activity pattern based on a first activity pattern at an auditory model of a first ear and a second activity pattern at an auditory model of a second ear may have the steps of identifying a first trajectory in the first activity pattern and a second trajectory in the second activity pattern, which are associated with the same sound events, determining a time shift between the two identified trajectories associated with the same sound event, determining whether the two trajectories are associated with a sound event of a useful sound source, and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern, wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model, wherein identifying a first trajectory and a second curved trajectory includes identifying a first curved trajectory in the first activity pattern and a second curved trajectory in the second activity pattern as trajectories belonging to the same sound event, when the first trajectory and the second trajectory have the same curvature within a predetermined tolerance range, and wherein determining whether the two identified trajectories are associated with a sound event of a useful sound source is executed using the time shift.

According to another embodiment, a method for generating a debugged audio signal based on an audio signal comprising at least two channels may have the steps of, generating a first activity pattern at an auditory model of a first ear based on a first channel of the audio signal and generating a second activity pattern at an auditory model of a second ear based on a second channel of the audio signal, generating a filtered activity pattern based on the first activity pattern and the second activity pattern according to a method for generating a filtered activity pattern based on a first activity pattern at an auditory model of a first ear and a second activity pattern at an auditory model of a second ear, having the steps of identifying a first trajectory in the first activity pattern and a second trajectory in the second activity pattern, which are associated with the same sound events, determining a time shift between the two identified trajectories associated with the same sound event, determining whether the two trajectories are associated with a sound event of a useful sound source, and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern, wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model, wherein identifying a first trajectory and a second curved trajectory includes identifying a first curved trajectory in the first activity pattern and a second curved trajectory in the second activity pattern as trajectories belonging to the same sound event, when the first trajectory and the second trajectory have the same curvature within a predetermined tolerance range, and wherein determining whether the two identified trajectories are associated with a sound event of a useful sound source is executed using the time shift, and converting the filtered activity pattern into a time illustration, a frequency illustration or a subband illustration to acquire the debugged audio signal.

According to another embodiment, a computer program for performing a method for generating a filtered activity pattern based on a first activity pattern at an auditory model of a first ear and a second activity pattern at an auditory model of a second ear may perform the steps of identifying a first trajectory in the first activity pattern and a second trajectory in the second activity pattern, which are associated with the same sound events, determining a time shift between the two identified trajectories associated with the same sound event, determining whether the two trajectories are associated with a sound event of a useful sound source, and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern, wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model, wherein identifying a first trajectory and a second curved trajectory includes identifying a first curved trajectory in the first activity pattern and a second curved trajectory in the second activity pattern as trajectories belonging to the same sound event, when the first trajectory and the second trajectory have the same curvature within a predetermined tolerance range, and wherein determining whether the two identified trajectories are associated with a sound event of a useful sound source is executed using the time shift, when the computer program is executed on a computer.

According to another embodiment, a computer program for performing a method for generating a debugged audio signal based on an audio signal comprising at least two channels may perform the steps of generating a first activity pattern at an auditory model of a first ear based on a first channel of the audio signal and generating a second activity pattern at an auditory model of a second ear based on a second channel of the audio signal, generating a filtered activity pattern based on the first activity pattern and the second activity pattern according to a method for generating a filtered activity pattern based on a first activity pattern at an auditory model of a first ear and a second activity pattern at an auditory model of a second ear, with the steps of identifying a first trajectory in the first activity pattern and a second trajectory in the second activity pattern, which are associated with the same sound events, determining a time shift between the two identified trajectories associated with the same sound event, determining whether the two trajectories are associated with a sound event of a useful sound source, and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern, wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model, wherein identifying a first trajectory and a second curved trajectory includes identifying a first curved trajectory in the first activity pattern and a second curved trajectory in the second activity pattern as trajectories belonging to the same sound event, when the first trajectory and the second trajectory comprise the same curvature within a predetermined tolerance range, and wherein determining whether the two identified trajectories are associated with a sound event of a useful sound source is executed using the time shift, and converting the filtered activity pattern into a time illustration, a frequency illustration or a subband illustration to acquire the debugged audio signal, when the computer program is executed on a computer.

The present invention provides a device for generating a filtered activity pattern according to patent claim 1.

It is the central idea of the present invention that a filtered activity pattern may be generated in an especially reliable way based on a first activity pattern on the auditory model of a first ear and a second activity pattern on the auditory model of a second ear, by identifying trajectories in the first activity pattern and in the second activity pattern associated with the same sound event by determining whether the two identified trajectories are associated with a sound event from a useful sound source, and by obtaining the first activity pattern or the second activity pattern based on the result of determining whether a trajectory is associated with a sound event from the useful sound source (or a sound event from an interfering sound source).

It was found that, by the use of two activity patterns formed on the auditory model of a first ear and an auditory model of a second ear, especially precise information may be achieved about whether two trajectories occurring in both activity patterns and associated with the same sound event come from a useful sound source or an interfering sound source. If a first trajectory based on the auditory model of the first ear and a second trajectory based on the auditory model of the second ear are determined, wherein the trajectories belong to the same sound event, then it may be seen in an especially simple and reliable way by comparing the two trajectories, whether the trajectories come from a useful sound source or an interfering sound source.

The reason for this is that trajectories coming from a useful sound source are usually distorted and/or temporally shifted with regard to each other at the two ears in a different way than trajectories belonging to the interfering sound source. Due to the distortion and/or shifting of two trajectories belonging to the same sound event, in the two activity patterns thus an especially simple assignment is possible whether the trajectories are associated with a useful sound event or an interfering sound event.

The knowledge whether a trajectory is associated with a useful sound event or an interfering sound event (and/or a useful sound source or an interfering sound source) is, moreover, used within the scope of the inventive filter to obtain the filtered activity pattern from the first activity pattern or from the second activity pattern such that in the filtered activity pattern activity events which are associated with a sound event from the useful sound source dominate with respect to sound events associated with an interfering sound source, or that in the filtered activity pattern activity events which are not associated with a sound event from the useful sound source are no longer present and/or removed.

In other words, the inventive concept basically consists in determining, by a comparison and/or determination of a distortion or a temporal shift of trajectories in the first activity pattern and in the second activity pattern which are associated with the same sound event, whether the trajectories belong to a useful sound event from a useful sound source or to an interfering sound event from an interfering sound source, and to filter the first activity pattern or the second activity pattern based on the mentioned information in order to obtain the filtered activity pattern.

It is a basic advantage of the present invention that, when generating a filtered activity pattern, two ears are used. For the determination whether a trajectory is associated with a useful sound source or an interfering sound source, thus the complete available information of two auditory models is used (e.g. of a left ear and a right ear). For the identification of trajectories of useful sound sources and/or or interfering sound sources, thus relationships between trajectories of the first activity pattern and the second activity pattern which belong together (belonging to the same sound event) may be used. By this, an especially efficient and reliable differentiation of trajectories of useful sound sources and interfering sound sources is achieved which is, moreover, based on the binaural processing of acoustic signals in the human brain.

According to an embodiment of the present invention, the identifier is implemented to determine a time shift between the two identified trajectories associated with the same sound event. In this case, the determiner is implemented to determine, using the time shift, whether two trajectories which are associated with the same sound event are associated with a sound event from a useful sound source or a sound event from the interfering sound source.

The described concept according to one embodiment of the present invention is based on the finding that in particular a time shift between two trajectories is an especially differentiating feature which enables trajectories from a useful sound event and/or a useful sound source to be separated from trajectories from an interfering sound source and/or an interfering sound event. The time shift between the trajectories is a measure for a spatial position of the sound source. A time shift typically results from a run-time difference between the sound source and the first ear and between the sound source and the second ear. This run-time difference depends on a position of the sound source relative to the two (spaced apart) ears.

It has further turned out that in particular the run-time difference, i.e. the direction from which the sound from a useful sound source and/or an interfering sound source comes, is an especially important and efficient feature for separating useful sound sources and interfering sound sources, as it typically leads to good results to receive sound events from exactly one direction and/or from a limited (possibly also non-adjacent) angular range and to regard sound events which have their origin outside the mentioned angle range as interfering sound sources. It is thus advantageous to reduce or suppress activities which have their origin outside the mentioned angle range.

The present invention further provides a corresponding method for generating a filtered activity pattern according to claim 51.

With regard to the findings underlying this method and the advantages of the inventive method as compared to conventional methods, apart from that reference is made to the implementations with regard to the device according to claim 1.

The present invention further provides a source divider according to claim 50.

According to a central idea of the present invention it has been found that it is advantageous for the separation of several sources, for example a useful sound source and an interfering sound source in at least a two-channel audio signal, first of all to separately convert the two channels of the audio signal into activity patterns on the auditory model of a first ear and on the auditory model of a second ear. Based on the activity patterns, then trajectories in the activity patterns which are associated with the same sound event are recognized. Based on the detection and/or identification of two trajectories which are associated with the same sound event, then, as already explained above, it is determined whether the two trajectories are associated with a sound event from a useful sound source or a sound event from an interfering sound source. Thus, a source separation may take place in the inventive way on the basis of the activity patterns.

It has turned out that, in particular using activity patterns on an auditory model, sound sources may be separated in an especially efficient way, as the sound events from different sound sources in the activity pattern are represented as distinguishable trajectories. While, in a temporal representation of an audio signal and/or in a frequency representation of the audio signal, the signals belonging to different sound sources overlap, the different sound sources and/or the information contents of the different sound sources in activity patterns of an auditory model are represented by separate, distinguishable trajectories. For this reason, a filtering on the basis of the activity patterns of the auditory model is especially efficient and, apart from that, adapted to a processing in a human brain, so that in the filtered activity pattern interfering sound sources may be suppressed or removed, respectively, with an especially high suppression. The detection of the trajectories belonging to useful sound events or interfering sound events, respectively, is, moreover, as already described above, achieved in an especially reliable and efficient way by the use of two activity patterns for auditory models of two ears. By a subsequent back-transformation of the filtered activity pattern into a time representation, a frequency representation or a subband representation of the debugged audio signal described by the filtered activity pattern, a further conventional post-processing of the filtered audio signal (i.e. of the audio signal obtained from the filtered activity pattern by back-transformation) is enabled.

Apart from that, the present invention provides a method for generating a debugged audio signal according to patent claim 52. The mentioned concept for generating a debugged activity pattern corresponds to that of the inventive source divider regarding its functioning.

The present invention further provides a computer program according to claim 53.

Apart from that, it is to be noted that embodiments of the present invention are defined by the dependent patent claims.

BRIEF DESCRIPTION OF THE DRAWINGS

In the following, embodiments of the present invention are explained in more detail with reference to the accompanying drawings, in which:

FIG. 4b shows a schematical illustration of a filtered activity pattern generated based on the activity patterns according to FIG. 4a;

FIG. 5b shows a detailed circuit diagram of a column of an inventive multi-coincidence means according to FIG. 5a;

FIG. 5c shows a circuit diagram of a coincidence cell for use in a multi-coincidence means according to FIG. 5a;

DETAILED DESCRIPTION OF THE INVENTION

Figure 1:
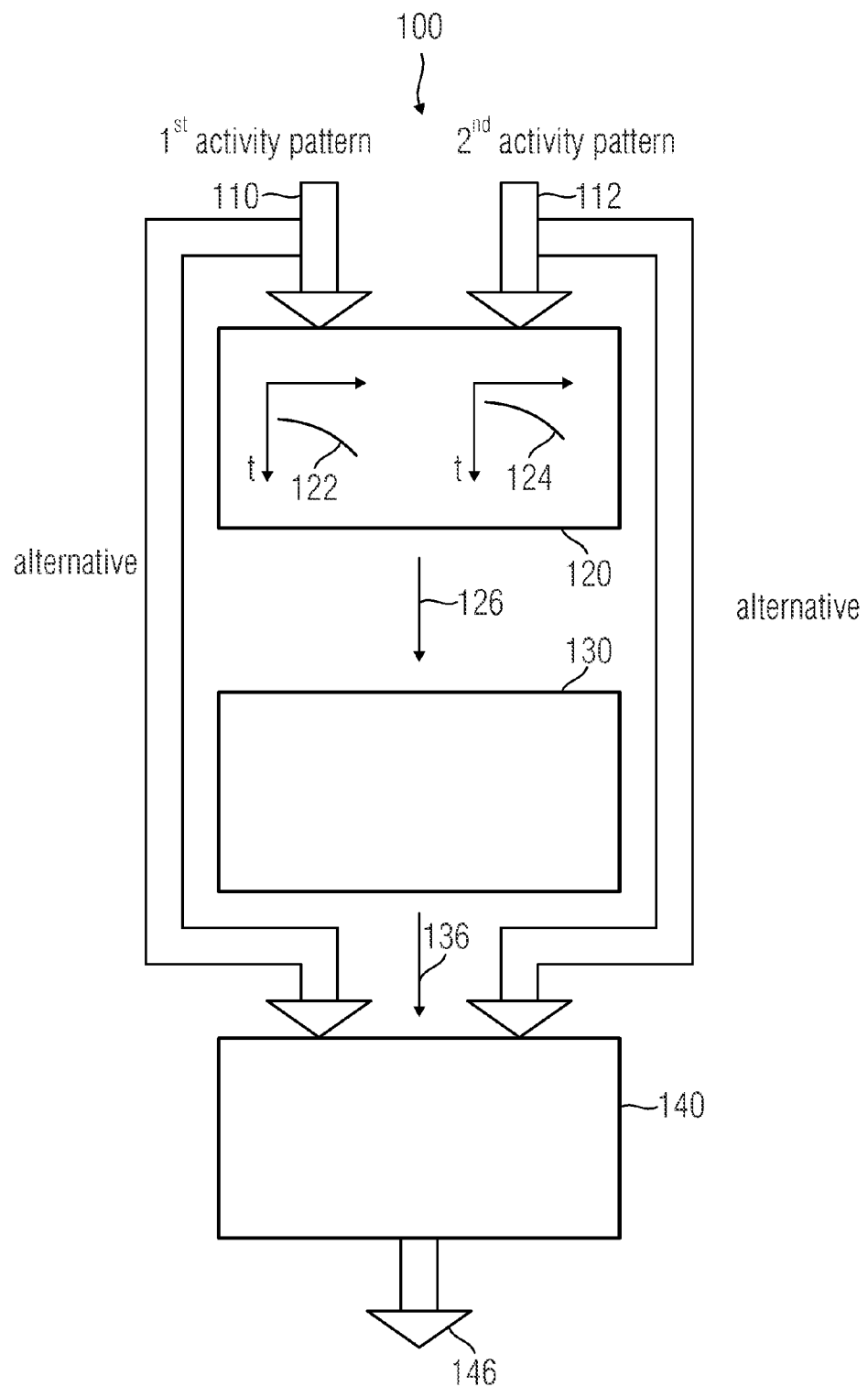
FIG. 1 shows a block diagram of an inventive device for generating an activity pattern according to one embodiment of the present invention.

FIG. 1 shows a block diagram of an inventive device for generating a filtered activity pattern based on a first activity pattern on an auditory model of a first ear and a second activity pattern on an auditory model of a second ear. The device according to FIG. 1 is designated by 100 in its entirety. The device 100 is implemented to receive a first activity pattern 110 from an auditory model of a first ear. The device 100 is further implemented to receive a second activity pattern 112 from an auditory model of a second ear. The device 100 includes an identifier 120 which is implemented to receive the first activity pattern 110 and the second activity pattern 112. The identifier 120 is implemented to detect a first trajectory in the first activity pattern and a second trajectory in a second activity pattern which are associated with the same sound event (e.g. the start of a vowel, a consonant, a sound, a clocking noise or another sound which results in a traveling wave on the basilar membrane). The same sound event is here, for example, a sound event which leads to trajectories (at least approximately or within a tolerance range, respectively) having the same curvature and/or the same length. Advantageously, the same sound event is an equal event in an acoustic signal originating from a sound source.

The identifier 120 is further implemented to provide information 126 describing the first trajectory 122 in the first activity pattern 110 and the second trajectory 124 in the second activity pattern 112, which are both associated with the same sound event. A determiner 130 receives information 126 and is implemented to determine, based on the information 126 about the first trajectory 122 and the second trajectory 124, whether the two trajectories 122, 124 are associated with an equal sound event, a sound event from a useful sound source or a sound event from an interfering sound source. The determiner 130 thus provides information 136 which indicates whether the trajectories 122, 124 are associated with a useful sound event from a useful sound source or an interfering sound event from an interfering sound source.

The device 100 further includes a filter 140 for filtering the first activity pattern 110 or the second activity pattern 112 based on a result 136 of the determination whether a trajectory is associated with a sound event from the useful sound source or a sound event from the interfering sound source. The filter 140 thus either receives the first activity pattern 110 or, alternatively, the second activity pattern 112. It is, however, also possible for the filter 140 to receive both the first activity pattern 110 and also the second activity pattern 112.

Apart from that, the filter 140 is implemented to generate a filtered activity pattern 146 so that in the filtered activity pattern activity events dominate which are associated with a sound event from the useful sound source or that activity events which are not associated with a sound event from the useful sound source are not present any more or removed from the filter activity pattern, respectively.

Based on the structural description above, in the following the functioning of the device 100 is explained in more detail. The identifier 120 receives a first activity pattern 110 and a second activity pattern 112. The activity patterns 110, 112 are, for example, each a plurality of parallel signals describing an activity in or at auditory cells (advantageously inner auditory cells or inner hair cells) of an auditory model. In other words, the first activity pattern 110 includes a plurality of parallel signals or information, respectively, describing an activity in or at a plurality of auditory cells of a first ear (e.g. a left ear). The second activity pattern 112 further typically includes a plurality of parallel information or signals describing an activity in or at auditory cells (advantageously inner auditory cells or inner hair cells) of a second ear.

Alternatively, the activity patterns may also describe an activity on nerve fibers of auditory nerves. For example, the first activity pattern 110 may describe an activity (or the time course of an activity, respectively) on a plurality of nerve fibers belonging to a first ear (e.g. left ear), while the second activity pattern 112 describes an activity on a plurality of nerve fibers belonging to a second ear (e.g. a right ear).

Apart from that, it is advantageous that the first activity pattern 110 and the second activity pattern 112 are gained by the use of auditory models for the first ear and the second ear. In other words, the auditory model for the first ear receives a first audio signal, for example from a first microphone arranged at the left side of a (for example human) head and provides the first activity pattern.

It is further advantageous, that the second activity pattern is determined by an auditory model of a second ear (e.g. a right ear) based on a second audio signal. The second audio signal may, for example, be provided by a second microphone, for example arranged at the right side of a (for example human) head.

Thus, the first activity pattern 110 and the second activity pattern 112 typically describe two audio signals from two different audio signal sources (e.g. from two differently arranged microphones). The two activity patterns may, however, also describe audio signals from at least two channels of a multi-channel audio signal.

Apart from that, it is to be noted that the first activity pattern 110 and the second activity pattern 112 are typically formed by a plurality of time signals, for example describing (for example in a two-dimensional representation of the same) a two-dimensional pattern. For example, the first activity pattern N may contain information or parallel time signals, respectively, describing an activity in or at N different auditory cells or at N different auditory nerves as a function of time. Similarly, the second activity pattern 112 may include a plurality of information or parallel (time) signals, respectively, describing a time course of an activity in or at a plurality of auditory cells or at a plurality of auditory nerves.

The occurrence of an activity (i.e., for example an active state, for example indicated by a characteristic change in the concentration of a certain substance or an electric potential) is referred to in the following as an activity event and may be seen from the activity patterns 110, 112. An activity event may, for example, be a neurotransmitter vesicle occurrence in an auditory cell (for example at the synaptic cleft of the auditory cell) or an occurrence of an (active) action potential on a nerve fiber.

The identifier 120 is implemented to receive the first activity pattern 110 and the second activity pattern 112 and to identify a first trajectory 122 in the first activity pattern 110 and a second trajectory 124 in the second activity pattern 112 which are associated with the same sound event. In this respect it is to be noted, that trajectories associated with the same sound event typically comprise at least a similar form and/or a similar length and may be identified as belonging together or belonging to the same sound event, respectively, based on the mentioned features. It is further known that trajectories associated with the same event or belonging to the same sound event, respectively, typically occur within a predetermined maximum time interval.

Thus, the identifier 120 is implemented to identify trajectories which are similar to each other, i.e., for example, trajectories whose curvatures deviate by less that a predetermined maximum admissible deviation and which occur within a predetermined maximum time interval, as trajectories belonging to the same sound event. Alternatively or additionally, the identifier 120 may further be implemented to consider a length of trajectories when determining whether two trajectories are associated with the same sound event. In other words, the identifier 120 may, for example, be implemented to indicate that two trajectories belong to an equal sound event when the same occur within a predetermined maximum time interval and when the same further comprise an equal length except for a predetermined maximum admissible deviation.

Based on a finding that two trajectories 122, 124 are associated with an equal sound event, the identifier 120 provides information 126 including information about the two identified trajectories 122, 124 belonging together. The information 126 may, for example, include information which enables finding at least one of the identified trajectories 122, 124 belonging together (or associated activity events, respectively) in the first activity pattern 110 or in the second activity pattern 112.

For example, the information 126 may include information about a point in time at which the trajectories 124 belonging together occur. Further, the information 126 may alternatively or additionally include information about a length of the two trajectories 122, 124. Alternatively or additionally, the information 126 further includes an indication as to how strongly the two trajectories 122, 124 are different from each other. The mentioned information 126 may, for example, give an indication as to in how far curvatures of the two trajectories 122, 124 which belong together and are associated with the same sound event differ. Further, the information 126 may alternatively or additionally carry information on how large a time shift between the two trajectories 122, 124 is.

The determiner 130 is implemented to receive the information 126 from the identifier 120 and to determine, based on that, whether the two identified trajectories 122, 124 belonging together are associated with a useful sound event or a useful sound source, respectively, or an interfering sound event or an interfering sound source, respectively. In an embodiment, the determiner 130 is implemented to derive information as to whether the two identified trajectories belonging together are associated with a useful sound source or an interfering sound source by a comparison of characteristics or features, respectively, of the two trajectories 122, 124 belonging together. Thus, the identifier 130 may, for example, be implemented to compare the lengths of two trajectories 122, 124 identified as belonging together. If the lengths deviate, for example, this may be seen as a sign that the two identified trajectories 122, 124 are associated with an interfering sound source, if it is, for example, assumed that the lengths of trajectories associated with a useful sound source are equal to each other within a predetermined tolerance range.

Further, the determiner 130 may be implemented to compare the curvatures of the two trajectories 122, 124 identified as belonging together to provide an indication based on that as to whether the two trajectories 122, 124 are associated with a useful sound source or an interfering sound source.

In a further embodiment the determiner is implemented to determine a time shift between the two trajectories 122, 124 identified as belonging together and to make the decision whether the trajectories identified as belonging together are associated with a sound event of a useful sound source or an interfering sound source based on a magnitude of the time shift between the trajectories 122, 124 identified as belonging together.

The filter 140 is implemented to receive information on the fact which trajectories identified by the identifier 120 are associated with a sound event of a useful sound source and/or which of the trajectories identified by the determiner 130 are associated with a sound event of an interfering sound source. In one embodiment, the filter 140 is implemented to receive the first activity pattern or the second activity pattern and to further receive information as to which of the trajectories contained in the first activity pattern or in the second activity pattern are associated with a useful sound source. The filter 140 is in this case implemented to take over the trajectories (or their activity events, respectively) designated by the information 136, associated with a sound event of a useful sound source, into the filtered activity pattern 146 and, for example, to suppress the remaining trajectories (or their activity events, respectively) in the first activity pattern 110 and the second activity pattern 112 when generating the filtered activity pattern 146 or at least to attenuate the same with regard to trajectories and/or activity events belonging to the useful sound events of the useful sound source.

In a further embodiment, the filter 140 is implemented to obtain information, as information 136, as to which of the trajectories 122, 124 identified by the identifier 120 are associated with a sound event of an interfering sound source. In this case, the filter 140 is implemented to remove or attenuate those trajectories (or the activity events belonging to the corresponding trajectories, respectively) from the first activity pattern 110 or from the second activity pattern 112 which belong to a sound event from the interfering sound source according to the information 136.

In other words, the filter 140 may, for example, be implemented, based on the first activity pattern 110 or on the second activity pattern 112, to only pass on those trajectories or sound events, respectively, which are associated with a sound event of the useful sound source according to the information 136. Alternatively, the filter 140 may be implemented to remove those trajectories or activity events, respectively, from the first activity pattern 110 or from the second activity pattern 112, which, according to the information 136, belong to a sound event from an interfering sound source.

Thus, at the output of the filter 146 all in all a filtered activity pattern results, in which trajectories or activity events, respectively, belonging to sound events of the interfering sound source, are suppressed or attenuated, and in which activity events or trajectories belonging to sound events from the useful sound source are contained in an unattenuated or amplified way.

Figure 2:
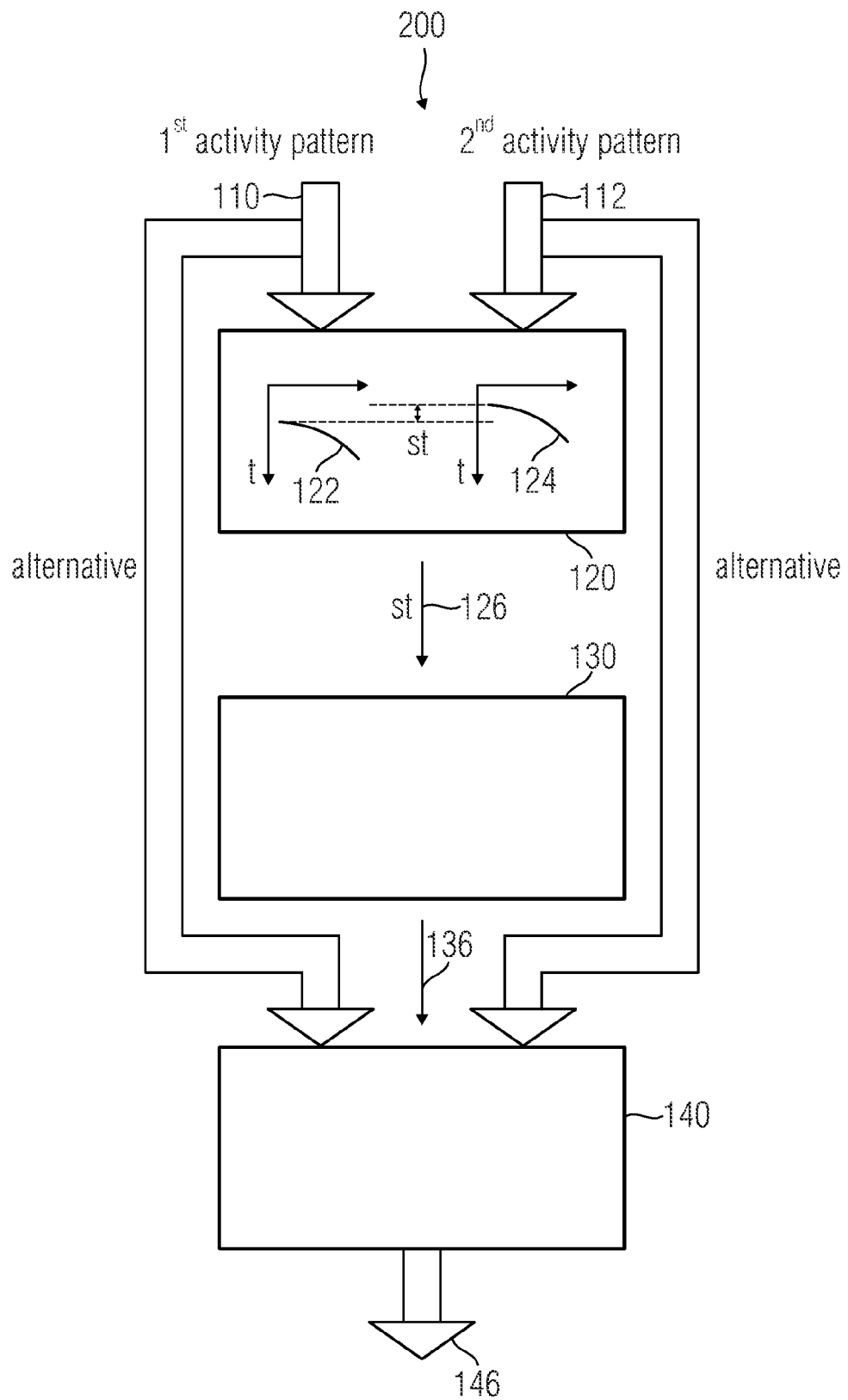
FIG. 2 shows a block diagram of an inventive device for generating a filtered activity pattern according to an embodiment of the present invention.

FIG. 2 shows a block diagram of an inventive device for generating a filtered activity pattern based on a first activity pattern on an auditory model of a first ear and a second activity pattern on an auditory model of a second ear. The device according to FIG. 2 is designated by 200 in its entirety. As the device 200 according to FIG. 2 is very similar to the device 100 according to FIG. 1, in the devices 100, 200 according to FIGS. 1 and 2, same features and signals are designated by the same reference numerals and are not discussed again.

The identifier 120 in the device 200 is selected to identify a first trajectory 122 in the first activity pattern 110 and a second trajectory 124 in the second activity pattern 112, which are associated with the same sound event. This identification may, for example, as already described above, be executed using a comparison of the curvatures of the two trajectories 122, 124 and/or of the lengths of the two trajectories 122, 124. Apart from that, for identifying two trajectories 122, 124 which are associated with an equal sound event, also one of the pattern recognition means described in the following may be used.

In addition to the identifier described with regard to the device 100, the identifier 120 of the device 200 is implemented to determine a time shift between the two trajectories 122, 124 belonging together (i.e. associated with the same sound event). The identifier 120 thus provides the information about the time shift between the two trajectories 122, 124 identified as belonging together as information 126 or as part of information 126, respectively, to the determiner 130. The determiner 130 is implemented to determine, using the time shift $\Delta t$ (or at least based on the time shift, respectively), whether the two trajectories 122, 124 are associated with a sound event of a useful sound source.

For this purpose, the determiner 130 may, for example, check whether the time shift $\Delta t$ between the two trajectories 122, 124 is within a predetermined admissible range. If the time shift $\Delta t$ between the two trajectories 122, 124 is within the predetermined admissible range, the determiner 130 may, for example, determine that the trajectories belong to a sound event from the useful sound source. If the time shift $\Delta t$ is outside of the predetermined admissible range, the determiner 130 may determine that the trajectories 122, 124 are associated with a sound event from the interfering sound source.

The admissible range may, for example, be firmly predetermined and is defined by the fact that, if a time shift $\Delta t$ within the admissible range is present, it is assumed that the two trajectories 122, 124 belong to the sound event from a useful sound source. In an embodiment it is assumed that the admissible range for the time shift of the trajectories 122, 124 includes values for the time shift whose amount is smaller than a predetermined upper limit. In other words, the two trajectories are identified as a sound event from a useful sound source when a time shift $\Delta t$ between the trajectories is smaller than a predetermined maximum value.

If it is assumed that the first activity pattern comes, for example, from a microphone arranged in the proximity of a first ear, and that the second activity pattern comes, for example, from a microphone arranged in the proximity of a second human ear, trajectories 122, 124 arriving at the same time in the two activity patterns 110, 112 indicate, for example, that the sound source is straight ahead of the head. A definition which determines a maximum amount of the time difference $\Delta t$ to identify two trajectories 122, 124 as belonging to the sound event from the useful sound source thus corresponds to the determination of an angle range in front of the head of a person, in the proximity of whose ears the audio signals are recorded on which the first activity pattern 110 and the second activity pattern 112 are based.

In an alternative embodiment, it is, however, advantageous to determine the admissible range based on characteristics of the signals underlying the activity patterns 110, 112. For this purpose, it may, for example, be determined for a plurality of ranges of time shifts when associated trajectories occur for each of the ranges of time shifts. In other words, for example pairs of all those trajectories belonging together are determined (which comprise the same curvature or are associated to the same sound event), whose time shift with regard to each other is in a range between $\Delta t$ and $\Delta t_2$. Based on the trajectories having time shifts in the range between $\Delta t_1$ and $\Delta t_2$, then an occurrence pattern is determined which indicates at which point in time trajectories with a time shift in the range between $\Delta t_1$ and $\Delta t_2$ occur. From the occurrence pattern or statistics derived from the occurrence pattern it is then, for example, determined whether the trajectories having time shifts in the range between $\Delta t_1$ and $\Delta t_2$ belong to a voice signal. In other words, from the occurrence pattern of trajectories having a time shift in the range or interval, respectively, between $\Delta t_1$ and $\Delta t_2$ statistics are determined which, for example, include an average time distance between points in time at which trajectories occur, a standard deviation between points in time at which trajectories occur, a maximum time distance between the occurrence of two trajectories, a minimum time distance between the occurrence of two trajectories or another statistical variable (e.g. an associated standard deviation of one of the above-mentioned statistical values). Based on one of the mentioned statistic variables or a combination of the mentioned statistical variables it may then be determined whether the trajectories whose time shifts are in the range between $\Delta t_1$ and $\Delta t_2$ describe a sound event of a useful signal or an interference signal.

As an alternative to the calculation of the statistics, apart from that also a pattern recognition may be applied to the occurrence pattern of the trajectories. In other words, the time pattern with which trajectories occur whose time shifts are in the range between $\Delta t_1$ and $\Delta t_2$ may be compared to at least one comparison pattern in order to determine whether the trajectories with a time shift in the range between $\Delta t_1$ and $\Delta t_2$ describe a useful signal or an interference signal. The comparison patterns may here include, for example, characteristic patterns which characterize an occurrence of trajectories in a typical useful signal (e.g. a voice signal) and/or in a typical interference signal.

If it is thus known, based on the above-described proceedings, that trajectories belonging together which comprise a time shift in the range between $\Delta t_1$ and $\Delta t_2$ describe sound events from a useful sound source or an interfering sound source, based on that the interval between the delay times $\Delta t_1$ and $\Delta t_2$ may be added to the admissible range or be removed from the admissible range.

In other words, the determiner 130 in this case includes a range adjustment means which is implemented to determine for a plurality of intervals of delay times (between two trajectories belonging together) whether trajectories with delay times within the respective intervals are associated with a useful sound source or an interfering sound source and to obtain the admissible range as a combination of those time intervals (of time shifts between trajectories belonging together) which are associated with useful sound sources.

Thus, the range selection means is implemented to select the admissible range (i.e. the range of time shifts $\Delta t$, so that trajectories 122, 124 belonging together having a time shift from the admissible range are identified as trajectories belonging to sound events from a useful sound source), so that the admissible range includes one or several (continuous or non-continuous) time intervals describing time shifts belonging to trajectories based on sound events from one or several useful sound sources.

The selection of the admissible range of time shifts $\Delta t$ may, apart from that, also be determined based on other characteristics of the acoustic signals on which the first activity pattern 110 and/or the second activity pattern 112 are based. For example, it may be determined which trajectories in the first activity pattern belong to a loudest sound signal. The admissible range may thereupon be set such that the trajectories belonging to a loudest sound signal comprise a time shift $\Delta t$ which is within the admissible range.

In other words, for setting the admissible range it is, for example, advantageous to determine, based on characteristics of an audio signal portion that may be determined (e.g. correlation characteristics, volume, time course of the intensity, bandwidth, occurrence time of trajectories), whether the corresponding audio signal portion is to be regarded as a useful signal from a useful signal source or as an interference signal from an interference signal source. Based on the mentioned classification of a signal portion as a useful signal from a useful signal source or an interference signal from an interference signal source and a determination of a time shift $\Delta t$ between trajectories 122, 124 belonging together which belong to the corresponding signal portion, then a range of time shifts is determined between $\Delta t_1$ and $\Delta t_2$, so that trajectories belonging to a useful signal from a useful signal source comprise a time shift $\Delta t$ in the range between $\Delta t_1$ and $\Delta t_2$, and that trajectories belonging to an interference signal from an interference signal source comprise a time shift outside the mentioned range.

In the following, it is determined by the determiner 130 that trajectories belonging together comprising a time shift $\Delta t$ in the range between $\Delta t_1$ and $\Delta t_2$ are to be regarded as trajectories belonging to the useful signal and are to be processed further.

Thus, all in all a dynamic adjustment of the admissible range of time delays $\Delta t$ is possible, wherein trajectories with a time delay within the admissible range are identified by the determiner 130 as trajectories belonging to a useful signal from a useful signal source.

After the determination of an admissible range $\Delta t$, apart from that only a time shift between trajectories 122, 124 belonging together has to be evaluated in order to decide whether the trajectories are to be identified as associated with a sound event of the useful signal source or associated with a sound event of the interfering signal source. Thus, after adjusting the admissible range, no cost and time-consuming processing of the activity patterns 110, 112 (for example in the form of a continuous determination of correlation characteristics) is needed any more to separate trajectories of the activity events based on the sound event of a useful signal source from trajectories of activity events based on a sound event of an interference signal source.

The separation of useful signals and interference signals is maintained as long as a time shift between trajectories belonging together associated with a sound event from a useful sound source do not change substantially. Only when, for example, the position of the useful sound source with regard to the microphones which serve for recording the audio signals on which the first activity pattern 110 and the second activity pattern 112 are based is changed, is a new setting of the admissible range that is needed.

It will be described in the following how the presence of a first trajectory 122 in the first activity pattern 110 and the presence of a second trajectory 124 in the second activity pattern 112 which are associated with an equal sound event may be detected and how further the time shift $\Delta t$ between the two trajectories 122, 124 may be determined in a technically advantageous way.

In this respect, it is first explained again briefly what a trajectory is and in what form the first activity pattern 110, the second activity pattern 112 and the filtered activity pattern 146 may be represented.

Figure 3A:
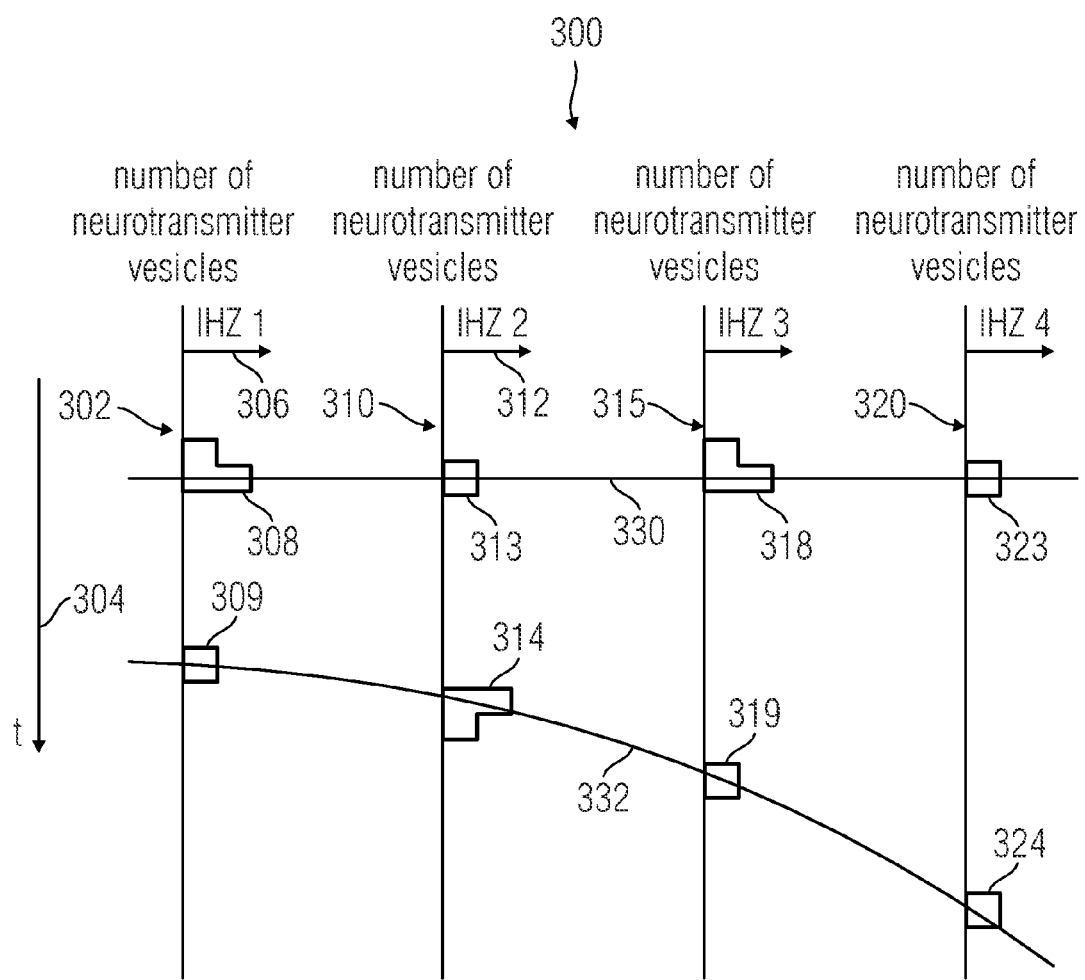
FIG. 3a shows a schematical illustration of trajectories in an activity pattern describing a number of neurotransmitter vesicles.

For this purpose, FIG. 3a shows a graphical illustration of two trajectories in an illustration of a neurotransmitter vesicle occurrence in or at an inner auditory cell, respectively.

The graphical illustration of FIG. 3a is designated by 300 in its entirety. A first illustration 302 shows a time course of a number of neurotransmitter vesicles occurring in or at a first inner auditory cell IHZ1. A time axis is here designated by 304, while a number axis 306 describes a number of neurotransmitter vesicles which are released within a time unit or which exist at a certain point in time in or at the considered inner auditory cell (for example in a released form). The first graphical illustration 302 shows a first neurotransmitter vesicle occurrence 308 and a second neurotransmitter vesicle occurrence 309. The first neurotransmitter vesicle occurrence 308 may, for example, be considered as a first activity event, and the second neurotransmitter vesicle occurrence 309 may, for example, be considered as a second activity event. A second graphical illustration 310 shows a neurotransmitter vesicle occurrence at a second inner auditory cell IHZ2. A number axis 312 describes a number of neurotransmitter vesicles in or at the inner auditory cell IHZ2 which are released per time unit or exist overall at a certain point in time (e.g. in a released form). A first neurotransmitter vesicle occurrence at the inner auditory cell IHZ2 is designated by 313, and a second neurotransmitter vesicle occurrence at the inner auditory cell IHZ2 is designated by 314. A third graphical illustration 315 shows, in a similar way, a neurotransmitter vesicle occurrence at a third inner auditory cell IHZ3, wherein a first neurotransmitter vesicle occurrence at the inner auditory cell IHZ3 is designated by 318, wherein a second neurotransmitter vesicle occurrence is designated by 319. A fourth graphical illustration 320 finally shows a first neurotransmitter vesicle occurrence 232 at a fourth inner auditory cell IHZ4 and a second neurotransmitter vesicle occurrence 324 at the fourth inner auditory cell IHZ4.

It is here to be noted that the inner auditory cells IHZ1, IHZ2, IHZ3, IHZ4 are, for example, arranged in such a way as will be described in the following with reference to FIG. 15.

Regarding the graphical illustration 300 of FIG. 3a, it may be seen that the first activity event 308 at the first auditory cell IHZ1, the first activity event 313 at the second inner auditory cell IHZ2, the first activity event 318 at the third inner auditory cell IHZ3 and the first activity event 323 at the fourth inner auditory cell IHZ4 are connected to each other by an approximately straight line 330 over time in a two-dimensional illustration of the activity events. The line 330 is thus a first trajectory. The second activity event 309 at or in the first inner auditory cell IHZ1, the second activity event 314 at or in the second inner auditory cell IHZ2, the second activity event 319 at or in the third inner auditory cell IHZ3 and the second activity event 324 at or in the fourth inner auditory cell IHZ4 are connected by a second line 332 in the graphical illustration 300 of FIG. 3a which forms a second trajectory.

A trajectory is here generally defined as being a line-shaped course connecting two, but advantageously more than two activity events belonging together which are based on the same sound event. A trajectory is typically either straight or curved in one single direction, i.e. does not change its direction of curvature. Further, a trajectory typically is a smooth curve which does not show any bends or non-differentiable thresholds, respectively. Apart from that, it is assumed within the scope of the present description that a plurality of activity events is associated with a trajectory, so that the term trajectory also includes the activity events associated with the trajectory. For example, the trajectory 330 includes the activity events 308, 313, 318, 323. The trajectory 332 moreover includes the activity events 309, 314, 319, 324.

It is further to be noted that a trajectory includes a plurality of activity events based on the propagation of a traveling wave on a basilar membrane of a human inner ear.

Figure 3B:
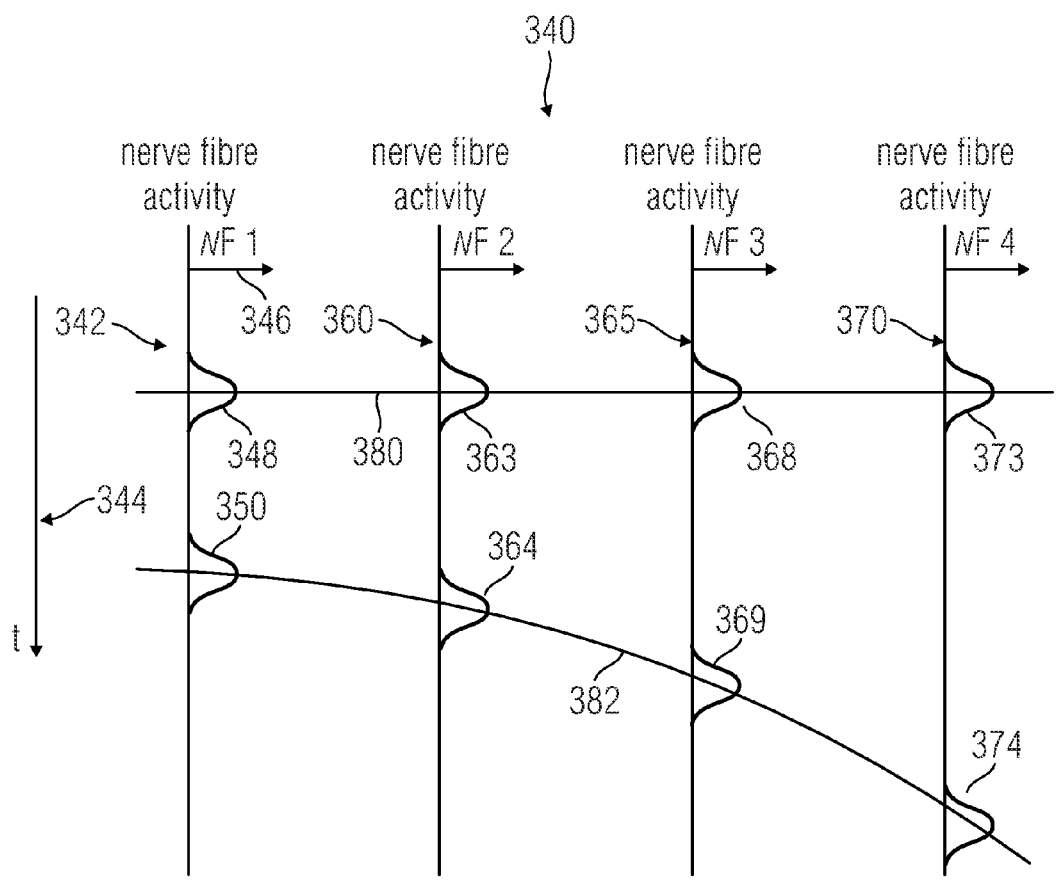
FIG. 3b shows a schematical illustration of trajectories in an activity pattern with regard to a plurality of nerve fibers.

FIG. 3b shows a graphical illustration of an activity on a plurality of nerve fibers coupled to the inner auditory cells of an auditory model. The graphical illustration of FIG. 3b is designated by 340 in its entirety. A first graphical illustration 342 shows an activity of a first nerve fiber which is, for example, coupled to the first inner auditory cell IHZ1. A time axis 344 here describes the time, while a potential axis 346 for example describes a potential on a first nerve fiber NF1. The graphical illustration 342, for example, shows a first activity event 348 which includes a triggering of an action potential on the first nerve fiber NF1. In other words, a potential course on the first nerve fiber NF1 comprises an activity (time change or impulse, respectively) forming the activity event 348. The first graphical illustration 342 further shows a second activity event 350 on the first nerve fiber NF1. A second graphical illustration 360 shows an activity of a second nerve fiber NF2 which is, for example, coupled to a second inner auditory cell IHZ2. Here, two activity events 363, 364 are obvious on the second nerve fiber NF2. A third graphical illustration 365 shows two activity events 368, 369 on a third nerve fiber NF3. Further, a fourth graphical illustration 370 shows two activity events 373, 374 on a fourth nerve fiber NF4.

It may further be seen that, in the graphical illustration 340 of FIG. 3b, describing an activity on a plurality of nerve fibers NF1, NF2, NF3, NF4 as a function of time, the activity events 348, 363, 368, 373 are connected to a first trajectory 380 or are all lying on the trajectory 308, respectively. Further, the activity events 350, 364, 369, 374 are connected by the trajectory 382 or are all lying on the trajectory 382, respectively.

Figure 3C:
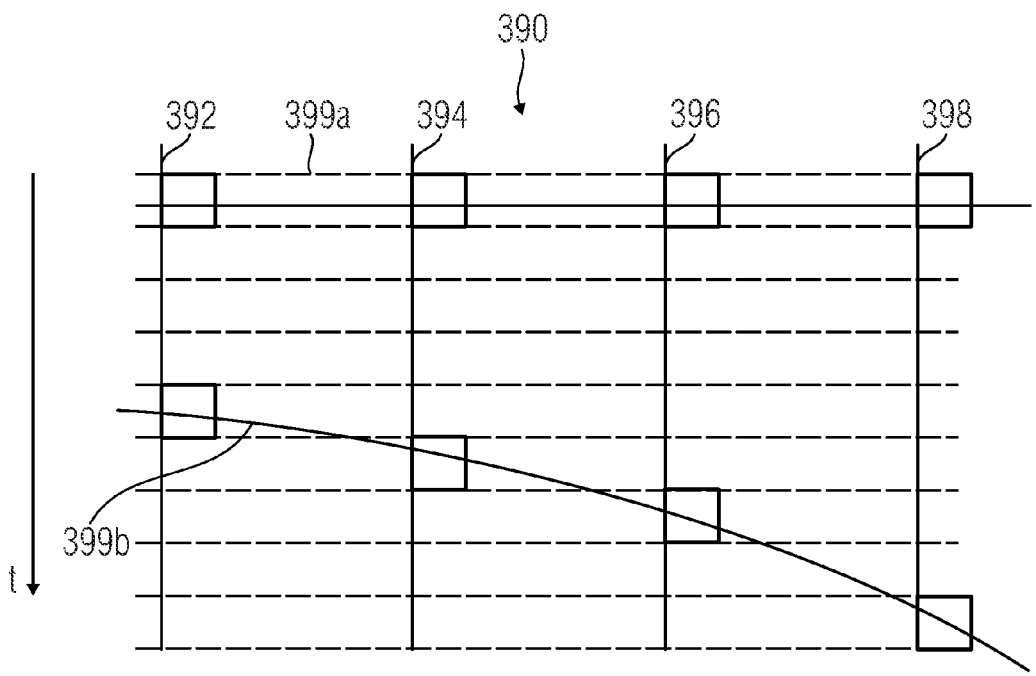
FIG. 3c shows a schematical illustration of digitized signals illustrating the activity patterns according to FIGS. 3a and 3b.

FIG. 3c shows a graphical illustration of time-discretized and value-discretized signals, for example based on the activity events illustrated in FIG. 3a or 3b. In other words, for example a plurality of time-discrete and value-discrete signals may be gained from the temporal illustration of the number of neurotransmitter vesicles at a plurality of inner auditory cells, wherein the signals describe the occurring activity events 3089, 313, 318, 323, 309, 314, 319, 324. For example, a first signal 392 describes activity events occurring at or in the first inner auditory cell IHZ1. A second signal 394 describes, for example, activity events occurring at or in a second inner auditory cell IHZ2. A third signal 396 describes, for example, activity events occurring at or in the third inner auditory cell IHZ3, and a fourth signal 398 describes, for example, activity events occurring at or in the fourth inner auditory cell IHZ4.

Alternatively, the four signals 392, 394, 396, 398 may also describe activity events on the nerve fibers NF1, NF2, NF3, NF4. In the two-dimensional time illustration 390 of FIG. 3c, activity events (or active states, respectively), are lying on the signals 392, 394, 396, 398 on the trajectories 398a, 399b.

In other words, the parallel (for example binary-valued) signals 392, 394, 396, 398 only represent an electric (for example binary-valued) representation of the activity events 308, 313, 318, 323, 309, 314, 319, 324 or of the activity events 348, 363, 368, 373, 350, 364, 369, 374, respectively. The fact that activity events within a two-dimensional illustration lie on trajectories is not influenced by the conversion into a representation as parallel signals 392, 394, 396, 398.

Figure 3D:
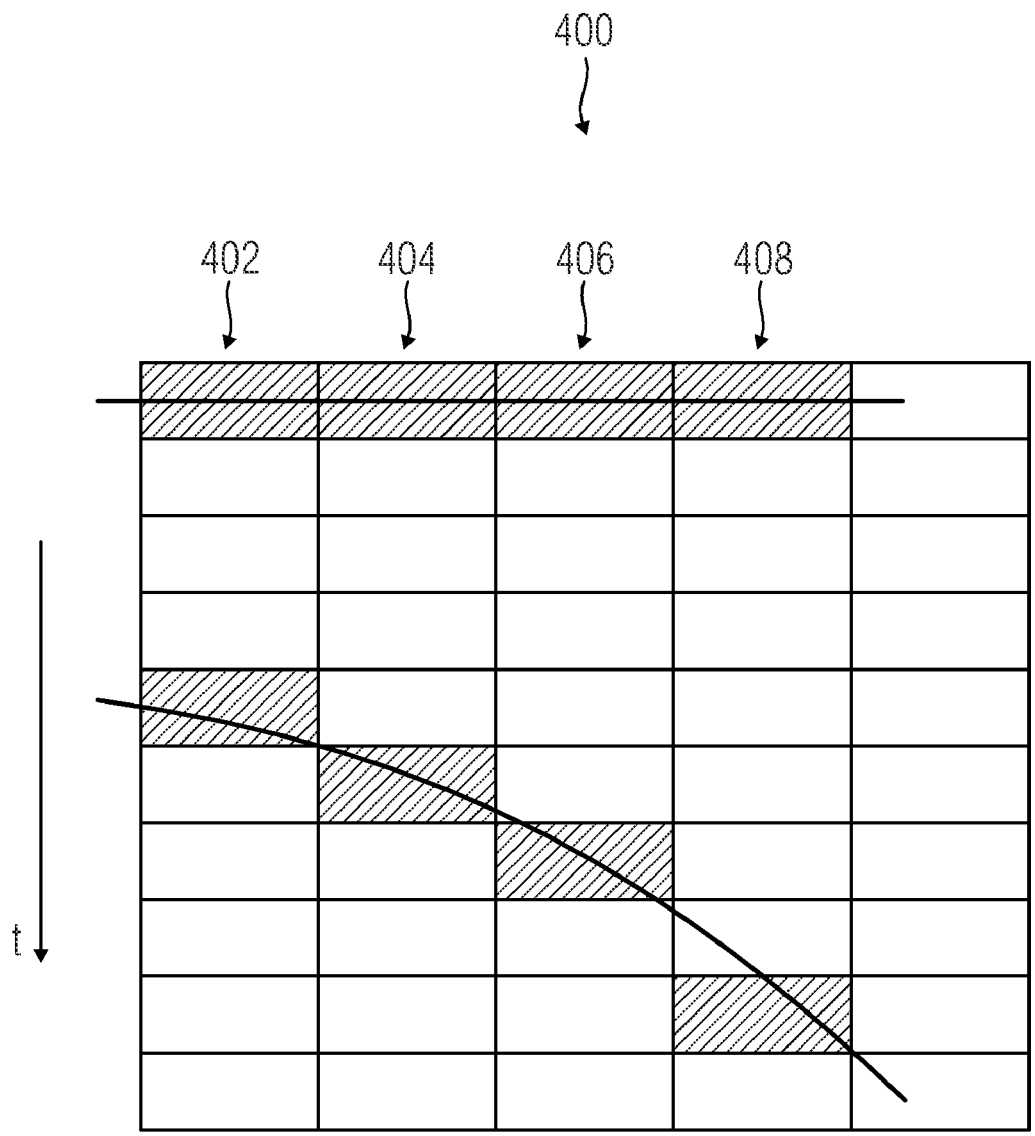
FIG. 3d shows a schematical illustration of a two-dimensional pattern describing the activity patterns according to FIG. 3a or 3b and which is based on the digitized signals according to FIG. 3c.

FIG. 3d further shows a graphical illustration of a pattern associated with the electric signals 392, 394, 396, 398 illustrated in the graphical illustration 390 of FIG. 3c. A time course of the first signal 392 here corresponds to a first column 402 of the pattern illustrated in the graphical illustration 400. A time course of the second signal 394 corresponds to a second column 404 of the pattern illustrated in the graphical illustration 400. A time course of the third signal 396 is represented by a third column 406 of the pattern 400. A time course of the fourth signal 398 is represented by a fourth column 408 of the pattern 400.

In other words, the pattern 400 according to FIG. 3d represents an occurrence of activity events 308, 309, 313, 314, 318, 319, 323, 324; 348, 350, 363, 364, 368, 369, 373, 374 in or at a plurality of (inner) auditory cells of an auditory model or at a plurality of nerve fibers of the auditory model. A conversion of the activity pattern according to FIGS. 3a, 3b into a pattern according to FIG. 3d may, for example, take place by a temporal, parallel sampling of the signals 392, 394, 396, 398 and by a shifting-on of samples of the mentioned signals by a shifting means.

It is thus to be noted that the activity patterns according to FIGS. 3a, 3b are open for methods of pattern recognition.

Figure 4A:
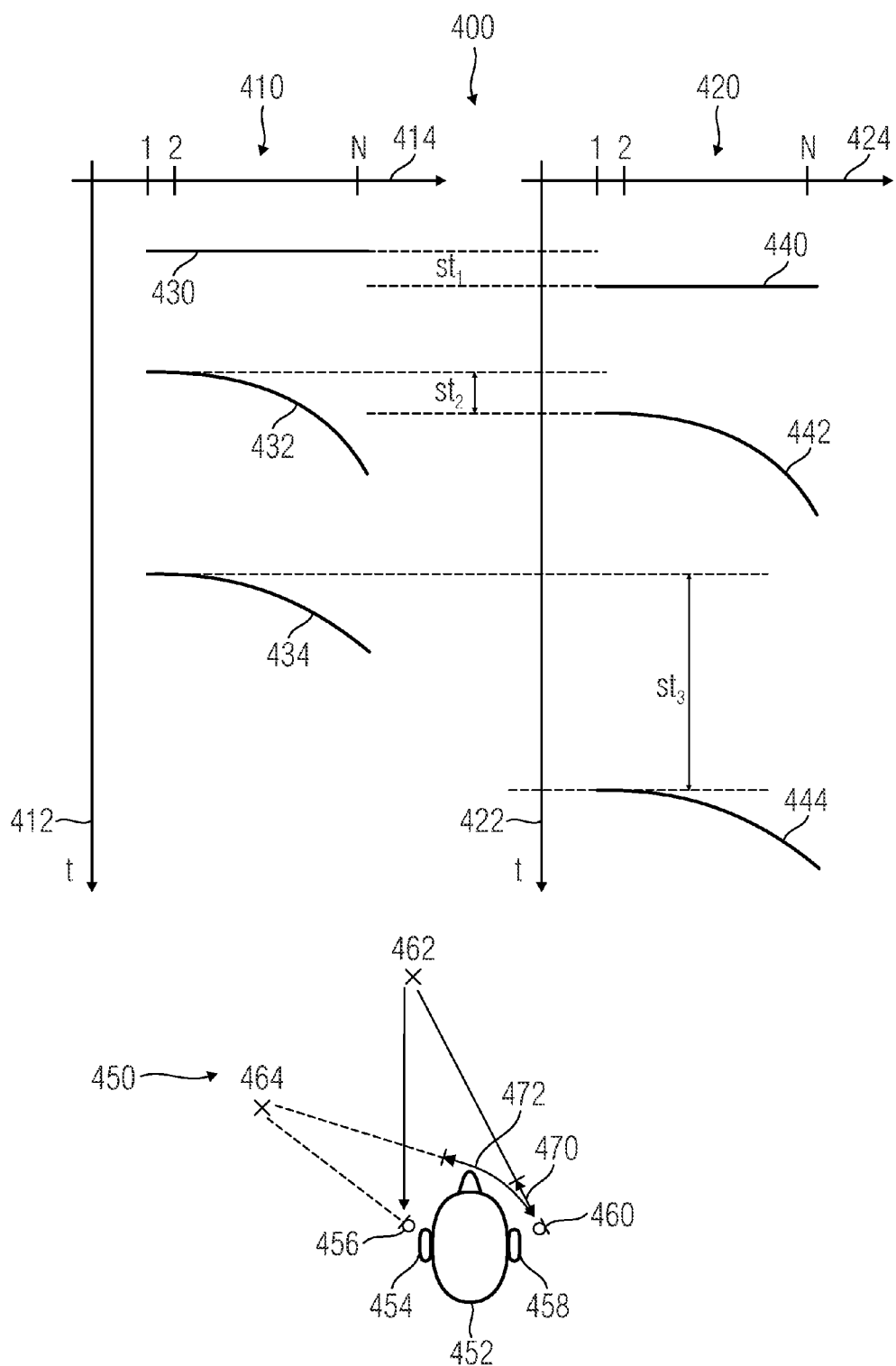
FIG. 4a shows a schematical illustration of a first activity pattern and a second activity pattern including a plurality of trajectories.
Figure 4B:
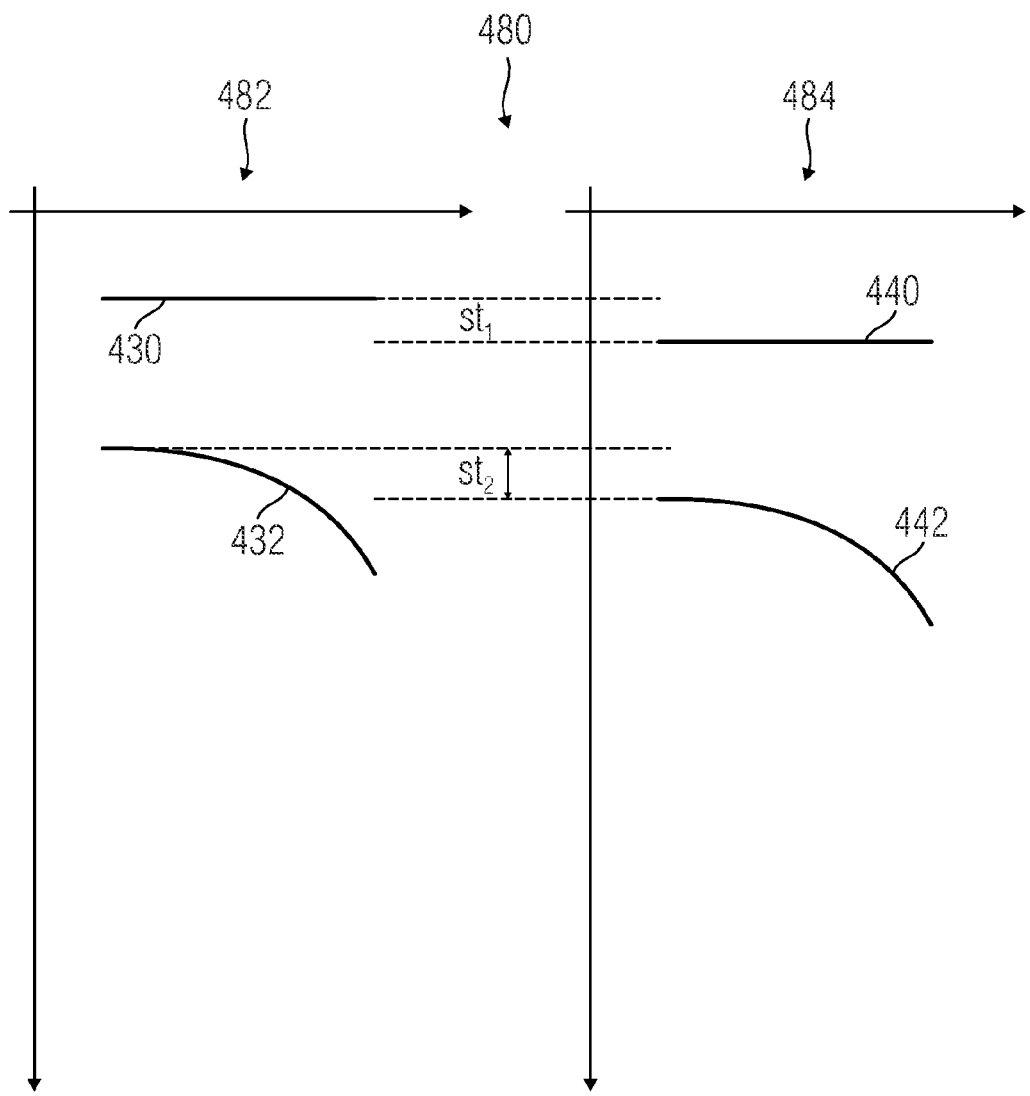

In the following, with reference to FIGS. 4a and 4b, an example of a processing of two activity patterns is described. The graphical illustration of FIG. 4a is designated by 400 in its entirety. A first graphical illustration 410 describes trajectories in an activity pattern at or in a plurality of inner auditory cells of an auditory model or at a plurality of nerve fibers of an auditory model. A first axis 412 here describes the time, while a second axis 414 describes a spatial position of inner auditory cells (on whose activity the activity pattern or, respectively, the trajectories are based) along a cochlea. Alternatively, the second axis 414 shows an index of a nerve fiber, wherein it is assumed that the nerve fibers are coupled to inner auditory cells and that the index of the nerve fiber describes a position of the inner auditory cell to which the nerve fiber is coupled along the cochlea in a monotonous way.

Apart from that it is to be noted that for reasons of clarity the graphical illustration 400 shows no individual activity events any more, but that a plurality of activity events belonging together (belonging to one single sound event) are described by a trajectory connecting the activity events in the two-dimensional illustration.

The first graphical illustration 410 moreover describes an activity pattern at an auditory model of a first ear, wherein it is assumed that the auditory model of the first ear is pulsed with a first audio signal. The second graphical illustration 420 shows a corresponding illustration of an activity pattern in the form of associated trajectories on an auditory model of a second ear, wherein it is assumed that the auditory model of the second ear is pulsed with a second audio signal.

The second graphical illustration 420 analog to the first graphical illustration 410 comprises an abscissa 422 at which the time is plotted. An ordinate 424 describes a spatial position of inner auditory cells along the cochlea or an index of the nerve fibers, respectively, as it was explained above.

The first graphical illustration 410 shows a first trajectory 430 which is straight or only comprises a slight first curvature. A second trajectory 432 comprises a stronger curvature than the first trajectory 430 and occurs in time after the trajectory 430. A third trajectory 434 for example comprises a third curvature which is different from the first curvature of the first trajectory 430 and the second curvature of the second trajectory 432. The third trajectory 434 moreover occurs in time after the first trajectory 430 and the second trajectory 432. The second activity pattern illustrated in the graphical illustration 420 comprises a fourth trajectory 440. It is assumed here that the first trajectory 430 and the fourth trajectory 440 are based on the same sound event of a useful sound source, and that thus the first trajectory 430 and the fourth trajectory 440 comprise the same curvature or curvatures which do not differ by more than a predetermined admissible deviation. Apart from that, it is to be noted that the fourth trajectory 440 occurs delayed in time by a time delay $\Delta t_1$ compared to the first trajectory 430.

The graphical illustration 420 further shows a fifth trajectory 442 contained in the second activity pattern. It is assumed here that the second trajectory 432 and the fifth trajectory 442 are based on the same sound event of the useful sound source. Thus, the second trajectory 432 and the fifth trajectory 442 comprise an equal curvature, or the curvatures of the second trajectory 432 and the fifth trajectory 442 differ by less than a predetermined maximum admissible deviation. It is further to be noted that the fifth trajectory 442 is delayed by the delay time $\Delta t_2$ compared to the second trajectory 432. As the trajectories 430, 432, 440, 442 are all based on sound events of the same useful signal source, it may be assumed that the delay time $\Delta t_2$ deviates by no more than a predetermined maximum admissible deviation from the delay time $\Delta t_1$.

The second graphical illustration 420 further shows a sixth trajectory 444 contained in the second activity pattern. It is here assumed that the third trajectory 434 and the sixth trajectory 444 are both based on an equal sound event of an interfering sound source. For this reason it may be assumed that the third trajectory 434 and the sixth trajectory 444 for example comprise the same curvature, or that the curvatures of the third trajectory 434 and the sixth trajectory 444 do not differ by more than a predetermined maximum admissible deviation. It is further assumed that the interfering sound source is located at a different location than the useful sound source. A graphical illustration 450 exemplarily shows this circumstance.

The graphical illustration 450 shows a top view of a human head 452. In the proximity of a first ear 454 (for example a left ear) a first microphone 456 is arranged. In the proximity of a second ear 458 (for example a right ear) a second microphone 460 is arranged. The graphical illustration 450 further shows the useful sound source 462 and the interfering sound source 464. It is further to be noted that it is assumed that the first graphical illustration 410 describes the first activity pattern generated from the audio signal received from the first microphone 456 using an auditory model of the human ear, and that further the second graphical illustration 420 shows the second activity pattern generated based on the microphone signal provided by the second microphone 460 by application of an auditory model (e.g. of the human ear) to the audio signal provided by the second microphone 460.

From the arrangement of the microphones 456, 460 as well as the useful sound source 462 and the interfering sound source 464 illustrated in the top view 450 it may be seen that there is, for example, a run-time difference between the useful sound source 462 and the first microphone 456 and between the useful sound source 462 and the second microphone 460. In other words, a sound event of the useful sound source 462 arrives at the first microphone 456 earlier than at the second microphone 460. The corresponding traveling difference is moreover designated by 470 and results in the time shift $\Delta t_1$.

In other words, due to the traveling difference 470, the fourth trajectory 440 in the second activity pattern is generated later by the delay time $\Delta t_1$ than the first trajectory 430 in the first activity pattern. If it is assumed that the useful sound source 462 does not move, it may thus further be assumed that the second delay time $\Delta t_2$ is equal to the first delay time $\Delta t_1$.

It is further to be noted that a traveling path between the interfering sound source 464 and the first microphone 456 is shorter by a traveling difference 472 than a traveling path between the interfering sound source 464 and the second microphone 460. For this reason, the sixth trajectory 444 describing a sound event of the interfering sound source 464 occurs later by the delay time $\Delta t_3$ than the third trajectory 434 which describes the same sound event of the interfering sound source 464. The delay time $\Delta t_3$ is here determined by the traveling difference 472.

In the illustrated example, the traveling difference 472 is greater than the traveling difference 470. Thus, the delay time $\Delta t_3$ is greater than the delay time $\Delta t_1$ or greater than the delay time $\Delta t_2$, respectively. In other words, the delay times $\Delta t_1$, $\Delta t_2$, $\Delta t_3$ between trajectories 430, 440; 432, 442; 434, 444 in the first activity pattern and in the second activity pattern which belong to the same sound events, depends on a position of the respective sound source relative to the two microphones 456, 460 (and depends on an angle under which the corresponding sound sources are located with regard to a connecting line of the two microphones 456, 460).

As already described above, the inventive device is implemented to first identify a trajectory in the first activity pattern and a second trajectory in the second activity pattern which are based on the same sound event. This may, for example, be executed by identifying trajectories comprising the same curvature and/or an equal length, and which further optionally additionally occur within a predetermined maximum time interval. By the determination of a maximum time interval it is considered that a time shift between two trajectories belonging to the same sound event in the first activity pattern and in the second activity pattern is limited to the top by a run-time difference between the first microphone 456 and the second microphone 460.

Based on the mentioned processing specification, the identifier 120 for example detects that the first trajectory 430 in the first activity pattern and the fourth trajectory 440 in the second activity pattern comprise an equal curvature, and thus associates the two trajectories 430, 440 to the same sound event. The identifier 120 further detects that the second trajectory 432 and the fifth trajectory 442 are based on the same sound event, as the two trajectories comprise an equal curvature and/or an equal length. Further, the identifier 120 detects that the third trajectory 434 and the sixth trajectory 444 are based on the same sound event.

The determiner 120 further determines the time delay $\Delta t_1$ between the occurrence of the first trajectory 430 and the fourth trajectory 440, i.e. between the trajectories belonging together which are based on the same sound event. Further, the determiner moreover determines the time delay $\Delta t_2$ between the occurrence of the second trajectory 432 and the occurrence of the fifth trajectory 442. Apart from that, the identifier 120 determines the time delay $\Delta t_3$ between the occurrence of the third trajectory 434 and the sixth trajectory 444.

The determiner 130 determines, based on the information about the trajectories 430, 432, 434, 440, 442, 444, which of the trajectories 430, 432, 434, 440, 442, 444 are associated with a sound event of a useful sound source and which trajectories are associated with a sound event of the interfering sound source.

In the simplest case the determiner 130 includes a means for determining whether a time shift between two trajectories 430, 440; 432, 442; 434, 444 belonging together is within a predetermined admissible range. It is assumed here that the determiner 130 includes a stored minimum delay value $\Delta t_{min}$ and a stored maximum delay value $\Delta t_{max}$, wherein the minimum admissible delay value $\Delta t_{min}$ and the admissible maximum delay value $\Delta t_{max}$ define an admissible range as an interval $[\Delta t_{min}; \Delta t_{max}]$. It is assumed here that the following applies:

$$\Delta t_{min} \leq \Delta t_1 \leq \Delta t_{max} \text{ and } \Delta t_{min} \leq \Delta t_2 \leq \Delta t_{max}.$$

Further, the following, for example, applies:

$$\Delta t_{max} \leq \Delta t_3.$$

Thus, the determiner 130 determines that the time delay $\Delta t_1$ between the first trajectory 430 and the fourth trajectory 440 is in the admissible range, and that further the time delay $\Delta t_2$ between the second trajectory 432 and the fifth trajectory 442 is in the admissible range. Thus, the determiner 130 signals by the signal 136, that the trajectories 430, 432, 440, 442 are trajectories associated with a sound event of the useful sound source. The determiner 130 further detects that the time delay $\Delta t_3$ is outside the admissible range and thus signalizes, for example via the signal 136, that the trajectories 434, 444 are associated with a sound event of the interfering sound source.

Based on the information 136 provided by the determiner, the filter 140 generates a filtered activity pattern. One example of the filtered activity pattern is illustrated in FIG. 4b. The graphical illustration of FIG. 4b is designated by 480 in its entirety. The graphical illustration 480 in a first graphical illustration 482 shows a first filtered activity pattern based on the first activity pattern according to the graphical illustration 410. The first filtered activity pattern includes the first trajectory 430 and the second trajectory 432 according to the first activity pattern. However, the first filtered activity pattern does not include the third trajectory 430 which is based on a sound event of the interfering signal source. In other words, in the generation of the first filtered activity pattern, for example, the filter 140 removes the trajectory 434 associated with the sound event of the interfering sound source. Alternatively, the filter 140 only takes over the trajectories 430 and 432 based on useful sound events of the useful sound source into the first filtered activity pattern.

A second graphical illustration 484 shows a second filtered activity pattern. The second filtered activity pattern 484, according to the second activity pattern, contains the fourth trajectory 440 and the fifth trajectory 442, but not the sixth trajectory 444. The second filtered activity pattern thus contains those trajectories of the first activity pattern associated with useful sound events from the useful sound source, but not trajectories associated with interfering sound events from the interfering sound source. Analog to that, the second filtered activity pattern includes the sound events of the second activity pattern associated with useful sound events of the useful sound source, but not trajectories associated with the interfering sound events of the interfering sound source.

Apart from that, it is to be noted that the first filtered activity pattern includes a plurality of activity events forming the respective trajectories. In other words, each trajectory represents a plurality of individual activity events.

Thus, it is, all in all, to be said that the first filtered activity pattern describes the information content of the useful sound source which may be perceived at the location of the first microphone 456. The information content of the interfering sound source 464 is not contained in the first filtered activity pattern, however, or only in a weakened form. Analog to that, the second filtered activity pattern contains an information content of the useful sound source 464 which may be perceived at the location of the second microphone 460, but not an information content of the interfering sound source 464, or only in a weakened form.

In the following, an extension of the above-described concept will be described which may be used to achieve an improved auditory impression or to achieve an improved distance of interference signals from an interference signal source, respectively. According to one embodiment of the present invention, nerve activity patterns are separately calculated for inner auditory cells with different response sensitivities.

In other words, an extended identification means receives a first activity pattern from an ear model of a first ear describing activity events in or at inner auditory cells comprising a first response sensitivity, a second activity pattern describing activity events in or at inner auditory cells comprising a second response sensitivity and a third activity pattern describing activity events in or at inner auditory cells comprising a third response sensitivity. The first response sensitivity is greater than the second response sensitivity, and the second response sensitivity is greater than the third response sensitivity. Apart from that, it is to be noted that the first activity pattern, the second activity pattern and the third activity pattern describe activity events at different types of inner auditory cells having different response sensitivities which result due to an excitation of the different auditory cells based on the same audio signal. For example, the three activity patterns originate from inner auditory cells having a low spontaneous emission rate (LSR), having a medium emission rate (MSR) or having a high spontaneous emission rate (HSR).

The extended identification means further receives a fourth activity pattern from an auditory model of a second ear, which describes activity events in or at inner auditory cells comprising a fourth response sensitivity, a fifth activity pattern describing activity events in or at inner auditory cells comprising a fifth response sensitivity and a sixth activity pattern describing activity events in or at inner auditory cells comprising a sixth response sensitivity. The fourth response sensitivity is greater than the fifth response sensitivity, and the fifth response sensitivity is greater than the sixth response sensitivity. Apart from that it is to be noted that the fourth activity pattern, the fifth activity pattern and the sixth activity pattern describe activity events at different types of inner auditory cells having different response sensitivities resulting due to an excitement of the different auditory cells based on the same audio signal.

The auditory models of the first ear and the second ear may, apart from that, optionally be part of the inventive device.

In other words, the first activity pattern for example describes activity events resulting at inner auditory cells of a high sensitivity, when the auditory cells of the high sensitivity are excited with a first audio signal. The second activity pattern describes activity events resulting in or at auditory cells of a medium sensitivity when the auditory cells are excited by the first audio signal. The third activity pattern further describes an activity pattern or activity events, respectively, resulting in or at inner auditory cells having a low sensitivity, when the inner auditory cell (or an ear model, respectively, including the corresponding inner auditory cells) is excited by the first audio signal.

The fourth activity pattern describes activity events resulting at inner auditory cells of a high sensitivity when the corresponding inner auditory cells (or, respectively, the underlying auditory model) are excited by a second audio signal. The fifth activity pattern describes activity events in or at inner auditory cells of a medium sensitivity, when the inner auditory cells are excited by the second audio signal, and the sixth activity pattern describes activity events in or at inner auditory cells of a low sensitivity, when the corresponding inner auditory cells are excited by the second audio signal.

In other words, the first, second and third activity patterns describe activity events at inner auditory cells having different sensitivities of an auditory model of a first ear excited by the first audio signal. The fourth, fifth and sixth activity patterns describe activity events at inner auditory cells having different sensitivities of an auditory model of a second ear excited by the second audio signal.

The identifier is in this case implemented to process activity patterns at the auditory model of the first ear and activity patterns at the auditory model of the second ear with each other which are associated with inner auditory cells of an equal sensitivity stage (high sensitivity; medium sensitivity; low sensitivity). For example, the identifier is in this case implemented to identify a first trajectory in the first activity pattern and a fourth trajectory in the fourth activity pattern which are associated with an equal sound event. For this purpose, for example the first activity pattern and the fourth activity pattern are supplied to a first detection means which is implemented to identify trajectories having the same curvature and/or the same length as the trajectories belonging together in the first activity pattern and the fourth activity pattern. The first detection means may, for example, be a multi-coincidence unit (for example according to FIG. 5a) or a detection means according to FIG. 7. The corresponding first detection means thus provides information at which points in time and with what time shift trajectories which are associated with an equal sound event occur in the first activity pattern and the fourth activity pattern.

In a similar way, a second detection means for example receives the second activity pattern and the fifth activity pattern and determines trajectories therein which are associated with an equal sound event. The second detection means thus provides information about when and/or with what time shift with respect to each other trajectories are contained in the second activity pattern and the fifth activity pattern which are associated with the same sound event.

A third detection means further receives the third activity pattern and the sixth activity pattern and identifies trajectories therein which are associated to equal sound events. The third detection means thus provides information about trajectories in the third pattern and the sixth activity pattern which are associated to the same sound events, and information about a time shift between trajectories which are associated with the same sound events.

By comparing information provided by the first detection means, the second detection means and the third detection means, it may be determined how high a volume of a sound event is which is described by a trajectory in one of the activity patterns.

In the following, three volume degrees are differentiated between. Thus, it is assumed that there are sound events of a high volume, sound events of a medium volume and sound events of a low volume. It is assumed that a sound event of a high volume results in a trajectory both in the first activity pattern, in the second activity pattern, in the third activity pattern, in the fourth activity pattern, in the fifth activity pattern and in the sixth activity pattern. It is further assumed that a sound event of a medium volume results in a trajectory in the first activity pattern, in the second activity pattern, in the fourth activity pattern, and in the fifth activity pattern, but not trajectories in the third activity pattern and in the sixth activity pattern. The reason for this is that the third activity pattern and the sixth activity pattern are formed by auditory cells of a low sensitivity, as it is assumed that a sound event of a medium volume is not strong enough to excite the auditory cells of a low sensitivity (whose reaction is described by the third activity pattern and the sixth activity pattern). A sound event of a low volume, however, only generates trajectories in the first activity pattern and in the fourth activity pattern. It is assumed that a sound event of a low volume is not sufficient to excite auditory cells of a medium sensitivity and of a low sensitivity, so that a sound event of a low volume does not lead to a trajectory in the second activity pattern and in the fifth activity pattern (formed by the auditory cells of a medium sensitivity) and just as little in the third activity pattern and the sixth activity pattern (formed by auditory cells of a low sensitivity).

It is thus possible, by a comparison of the trajectories in the first activity pattern, in the second activity pattern and in the third activity pattern, to gain information about a volume of a sound event.

In other words, a sound event volume detection means which is, for example, part of the identifier or part of the determiner, may be implemented to generate information and a volume of a sound event underlying a trajectory for a plurality of trajectories. The volume detection means may, for example, be implemented to detect whether in the first activity pattern and in the second activity pattern simultaneously (or, respectively, within a predetermined maximum time interval) trajectories having the same curvature (or, respectively, trajectories of a different curvature whose curvatures are different by less than a predetermined maximum admissible curvature difference) are present. If it is determined here that a trajectory of a certain curvature occurs in a first activity pattern for which no associated trajectories having a corresponding (at least approximately) equal curvature are present in the second activity pattern, then the volume determiner may, for example, detect that the trajectories present in the first activity pattern are associated with sound events of a low volume. Further, the volume detector may alternatively or additionally be implemented to detect whether in the second activity pattern and in the third activity pattern trajectories having at least approximately the same curvature occur at least approximately simultaneously. If for a trajectory no corresponding approximately simultaneously occurring associated trajectory of approximately the same curvature exists in the second activity pattern, then the volume detector may, for example, detect that the sound event to which the corresponding curvature in the second activity pattern belongs comprises a medium volume.

Further, the volume detector may, for example, determine that a sound event comprises a high volume when both in the first activity pattern and also in the second and the third activity patterns approximately simultaneously trajectories of approximately the same curvature occur.

A corresponding processing may also take place for the fourth activity pattern, the fifth activity pattern and the sixth activity pattern. If a trajectory occurs in the fourth activity pattern for which no corresponding, approximately simultaneously occurring trajectory of approximately the same curvature exists in the fifth activity pattern, then the volume detector may determine that the curvature occurring in the fourth activity pattern is associated with a sound event with a low volume. If the volume detector further identifies a trajectory in the fifth activity pattern for which no associated approximately simultaneously occurring trajectory of approximately the same curvature exists in the sixth activity pattern, then the volume detector may determine that the trajectory identified in the fifth activity pattern is associated with a sound event of a medium volume. If the volume detector further determines that in the fourth activity pattern, in the fifth activity pattern and in the sixth activity pattern approximately simultaneously occurring trajectories of approximately the same curvature occur, then the volume detector may determine that corresponding trajectories are associated with a sound event of a high volume.

In other words, the volume detector is implemented to associate volume information with the trajectories (or at least a part of the trajectories) occurring in the examined activity patterns.

For this purpose, the volume detector generally analyzes whether in the different considered activity patterns trajectories of the same curvature occur approximately simultaneously (i.e. within a predetermined maximum time interval), and, if yes, in which of the activity patterns trajectories of approximately the same curvature occur approximately simultaneously. Based on the mentioned information or, respectively based on a comparison between trajectories which occur in different activity patterns which are associated with the inner auditory cells of a different sensitivity, the volume detector thus determines volume information associated with the trajectories.

Apart from that, in one embodiment the filter 140 is implemented to consider the volume information during filtering. In other words, the filter 140 may be implemented to receive the volume information from the volume detector. Thus, the filter 140 may, for example, be implemented to filter out or, respectively, to remove or to attenuate all trajectories whose associated volume information is lower than a predetermined minimum volume. Alternatively, the filter may also be implemented to generate the filtered activity pattern such that in the filtered activity pattern only trajectories are contained which are associated with sound events according to the information provided by the volume detector, which comprise a volume within a predetermined range. For example, the filter 140 may be implemented to generate the filtered activity pattern such that in the activity pattern trajectories are emphasized or amplified, respectively, belonging to sound events of a low volume, while, for example, trajectories belonging to sound events of a higher volume are attenuated or even completely removed relative to that.

In this way it may, for example, be achieved that in the filtered activity pattern only or at least mainly trajectories are contained belonging to sound events of a low volume. Thus, it is enabled that, by the filtered activity pattern, in particular quiet signal portions in the original activity patterns are described, whereby an intelligibility of the quiet portions is improved or only enabled in the original activity patterns.

All in all, it may be said that the inventive device according to FIG. 1 or FIG. 2, respectively, may be extended by the device receiving two sets of activity patterns at auditory models of two ears, respectively describing activity events at auditory cells with a high spontaneous emission rate, a medium spontaneous emission rate and a low spontaneous emission rate. An identification of trajectories belonging to the same sound events thereupon takes place separately for activity patterns of auditory cells of different emission rates. In other words, an activity pattern of the ear model of the first ear for auditory cells of a high emission rate is processed together with an activity pattern at the ear model of the second ear for auditory cells of a high emission rate to obtain information on corresponding trajectories (based on the same sound event). In a similar way, a common processing is performed for two activity patterns belonging to auditory cells of a medium emission rate. Further, a common processing for two activity patterns of auditory cells of a low emission rate is performed. By a comparison between the trajectories in the first activity pattern, in the second activity pattern and in the third activity pattern, further volume information is gained which indicates whether the corresponding trajectories are associated with sound events of a low, high or medium volume. The volume information is then considered when filtering or when generating information whether trajectories are associated with a useful sound event or an interfering sound event.

Apart from that, it is to be noted that in an embodiment both volume information and also information about the time shift is to be considered. Thus, the filter (in connection with the determiner) may be implemented to obtain the filtered activity pattern such that in the filtered activity pattern trajectories dominate whose associated volume information is, for example, within a predetermined range, and whose associated time shift information is within a predetermined range. Thus, the filter (in connection with the determiner) may be implemented, for example, to generate the filtered activity pattern such that the filtered activity pattern basically includes an audio signal originating from a spatially limited range. An angular limitation of the range is here given by the limitation of the admissible time shift between two trajectories belonging together. A limitation regarding the distance here results from the limitation of the volume to a predetermined range.

In other words, the circuitry of FIG. 1 or FIG. 2, respectively (or at least the identifier 120 therefrom) is replicated three times in one embodiment. Thus, three parallel branches for three volume spaces HSR, MSR, LSR result. The setup is here structurally equal, however one time activity events or activity patterns, respectively, of auditory cells (or spiral ganglion cells) with a high spontaneous emission rate are processed, one time activity patterns of auditory cells with a medium spontaneous emission rate and one time also activity patterns of auditory cells with a low spontaneous emission rate.

In summary it may be said: in one embodiment the circuit (e.g. the identifier, the determiner, the multi-coincidence unit 500 and/or the detection means 700) are set up three times for an HSR space, an MSR space and an LSR space.

Thus, the present invention includes the following aspects:
a) binaural vesicle filtering by matching delay trajectories with regard to each other by a time shift;
b) direct vesicle filtering with regard to each other for determining the coincidence pairs;
c) noise suppression resulting therefrom by raking out the vesicles from noise sources;
d) precisely timed clocking and synchronization of the left and the right cochlear implant, so that sound sources may be located correctly in space.

According to a further aspect, the present invention provides a method and a device according to the aspects a), b), and c) in all three HSR, MSR, LSR spaces (wherein an HSR space is regarded as a plurality of auditory cells with a high spontaneous emission rate, wherein an MSR space is regarded as a plurality of auditory cells with a medium spontaneous emission rate, and wherein an LSR space is regarded as a plurality of auditory cells with a low spontaneous emission rate). As all three spiral ganglion cells (or, respectively, all three types of spiral ganglion cells, i.e. HSR cells, MSR cells and LSR cells) comprise different dynamic thresholds, by comparison, where the different types of cells (HSR, MSR, LSR) simultaneously trigger vesicles and/or by the formation of differential pairs, loud and faint sound sources may be separated.

In other words, the inventive system (for example according to FIGS. 1 and 2) is set up three times in one embodiment, wherein separate signals or activity patterns, respectively, from spiral ganglion cells with a high spontaneous emission rate, a medium spontaneous emission rate and a low spontaneous emission rate (HSR, MSR, LSR) are used. As the spiral ganglion cells with a different spontaneous emission rate have different response level ranges, a vesicle release (or in general: activity patterns) are different for loud, medium and quiet tones. Thus, signal sources of a different volume may be separated.

Figure 5A:
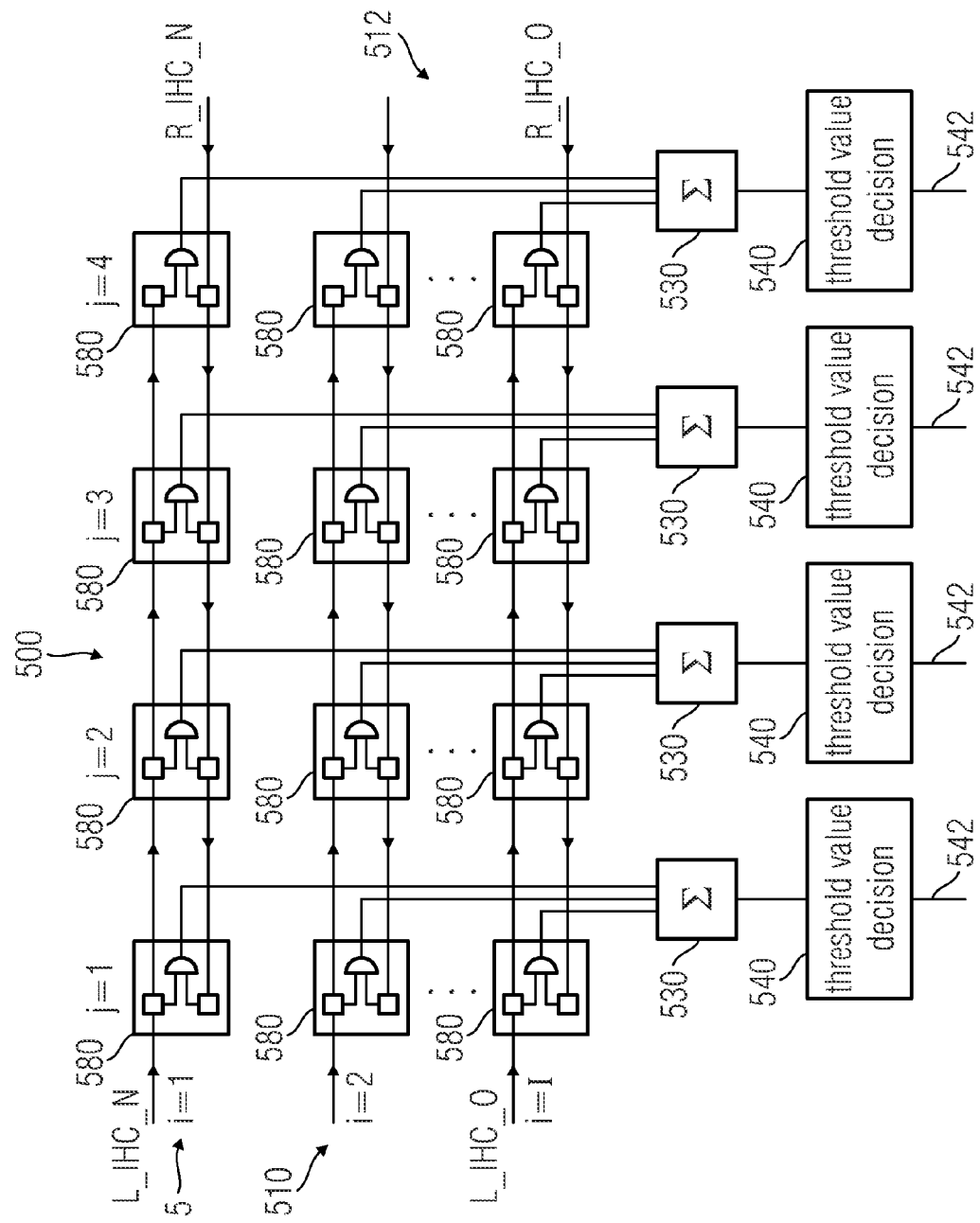
FIG. 5a shows a block diagram of an inventive multi-coincidence means according to an embodiment of the present invention.

FIG. 5a shows a circuit diagram of an inventive multi-coincidence unit for use in an inventive device according to one embodiment of the present invention. The circuitry according to FIG. 5a is designated by 500 in its entirety. The circuitry 500 is implemented to receive a first plurality 510 of parallel signals and a second plurality 512 of parallel signals. It is assumed that the first plurality 510 of parallel signals for example describe an activity pattern. In other words, time courses of the signals of the first plurality 510 of parallel signals describe a two-dimensional pattern (see FIGS. 3a to 3d). The same applies to signals of the second plurality 512 of parallel signals.

The circuitry 500 includes a field of coincidence cells. One example of a single coincidence cell is illustrated in FIG. 5c. In other words, FIG. 5c shows a circuit diagram of a coincidence cell. A coincidence cell 580 comprises a first data input 582 and a second data input 584. The coincidence cell 580 further comprises a first data output 586 and a second data output 588. The coincidence cell 580 includes a first memory means 590 and a second memory means 592. The first memory means or memory cell 590, respectively, and the second memory means or memory cell 592, respectively, are implemented to receive a common (or separate) clock signal 594 and to take over and store information from the input in response to the clock signal 594. Thus, the first memory cell 590 is, for example, implemented to take over an information (for example a binary value) from the first input 582, store the same and output it to the first output 586. Further, the second memory cell 592 is implemented to take over information (e.g. a binary value) from the second input 584 in response to the clock signal 594, store the same and output it at the second output 588. The coincidence cell 580 further includes an AND gate which is, for example, implemented to determine when both outputs 586, 588 of the coincidence cell 580 comprise an active state. The AND gate is designated by 596 and provides a coincidence signal 598.

The multi-coincidence unit 500 consists of a plurality of coincidence cells 580 whose interconnection will be described in the following. It is to be noted that the multi-coincidence unit 500 is set up in the form of a matrix of coincidence cells 580. The coincidence cells are designated by two indices i, j in the following, wherein the index i designates a line and wherein the index j designates a column. Apart from that, it is assumed that the multi-coincidence unit comprises at least I lines and at least J columns, wherein $I \geq 3$ and $J \geq 3$. The individual coincidence cells are designated by $Z(i,j)$.

Generally, the following applies: a first output of the coincidence cell $Z(i,j)$ is coupled to a first input of an adjacent coincidence cell $Z(i,j+1)$, wherein $1 \leq j \leq J-1$. Further, the second input of the coincidence cell $Z(i,j)$ is coupled to the second output of the coincidence cell $Z(i,j+1)$, wherein $1 \leq j \leq J-1$. A first input of the coincidence cell $z(i,j=1)$ receives an $i^{th}$ signal from a first plurality 510 of parallel input signals. A second input of the coincidence cell $Z(i,j=J)$ further receives an $i^{th}$ signal of the second plurality 512 of parallel signals.

In other words, the coincidence cells of the $i^{th}$ line are implemented to pass on the $i^{th}$ input signal of the first plurality 510 of parallel input signals step by step (in response to the time signal 594) in a first direction (e.g. from left to right), and to pass on the $i^{th}$ input signal of the second plurality 512 of parallel input signals step by step in a second direction (e.g. from right to left).

Thus, at the outputs 586, 588 of the coincidence cells Z(i,j) the passed-on signals are applied. The coincidence cells are here implemented to detect when the passed-on signal of the first plurality 510 of parallel signals at the first output 586 of the corresponding coincidence cell and the passed-on signal of the second plurality 512 of parallel signals at the second output 588 of the coincidence cell are simultaneously active. In this case, the corresponding coincidence cell outputs a coincidence signal at the output 598.

The multi-coincidence unit 500 further includes a summator 530. Here, at least one summator 530 is associated with a column of the multi-coincidence unit 500. In other words, a $j^{th}$ summator 530 is implemented to receive the coincidence signals 598 of the coincidence cells 580 of the $j^{th}$ column and sum the same up. Thus, the $j^{th}$ summator 530 is implemented to determine at the outputs of how many coincidence cells 580 of the $j^{th}$ column coincidence signals 598 occur simultaneously or within a predetermined time interval. The summator 530 may, apart from that, be implemented to receive a reset signal synchronously or asynchronously. In other words, time intervals may be defined in which a number of coincidences are summed up in the $j^{th}$ column of the multi-coincidence unit 500 to detect, for example, a trajectory.

The multi-coincidence unit 500 further includes threshold value deciders 540 which are implemented to receive an associated sum signal from an associated summator 530. The threshold value deciders 540 are thus implemented to detect when at least a predetermined number of coincidences occurred in the coincidence cells 580 of the $j^{th}$ column within the time interval during which a summation takes place within a single column j. In this case, the threshold value deciders 540 provide an associated threshold value signal 542.

In other words, the coincidence unit 500 is implemented to determine whether, within a predetermined time interval in a $j^{th}$ column, at least a predetermined number of coincidences occurred, while two activity patterns were shifted in the opposite direction through the multi-coincidence unit 500. A coincidence here is, as defined above, the simultaneous existence of two active signals in a coincidence stage 580.

It is assumed that, by the coincidence unit 500, two activity patterns which contain trajectories are shifted in opposite directions. Thus, a coincidence occurs when in the same coincidence cell both an activity event of the first activity pattern and also an activity event of the second activity pattern is applied. To put it simply, a coincidence occurs when a first trajectory in the first activity pattern (for example input into the multi-coincidence unit 500 via the first plurality 510 of parallel inputs) intersects a second trajectory in the second activity pattern (for example input into the multi-coincidence unit 500 via the second plurality 512 of parallel inputs). Thus, the multi-coincidence unit is all in all implemented to determine in what locations trajectories of the first activity pattern and trajectories of the second activity pattern intersect in the course of a shift of the two activity patterns.

A possibility of evaluating the results of the multi-coincidence unit 500 will be described in the following.

Figure 5B:
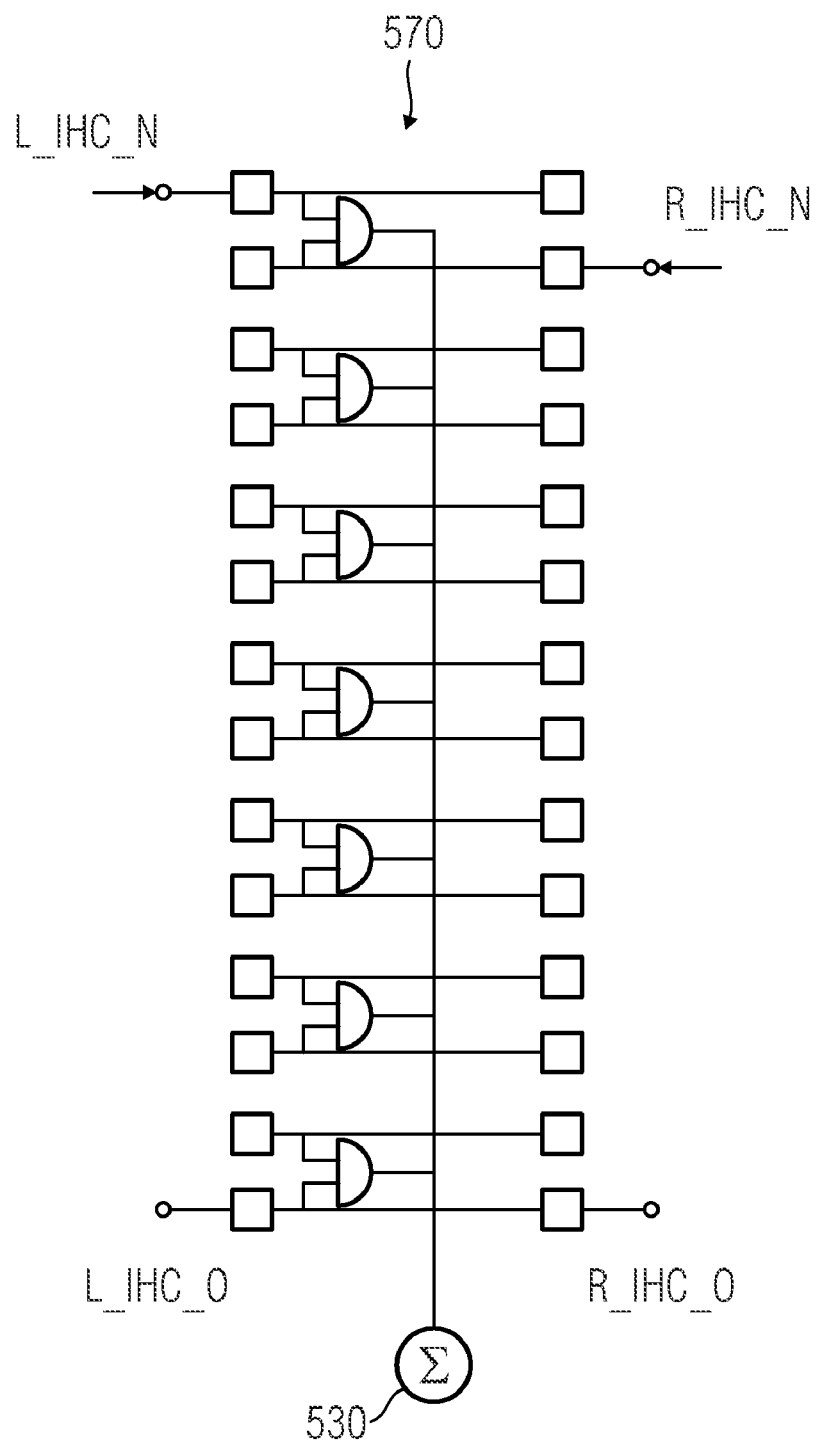
Figure 5C:
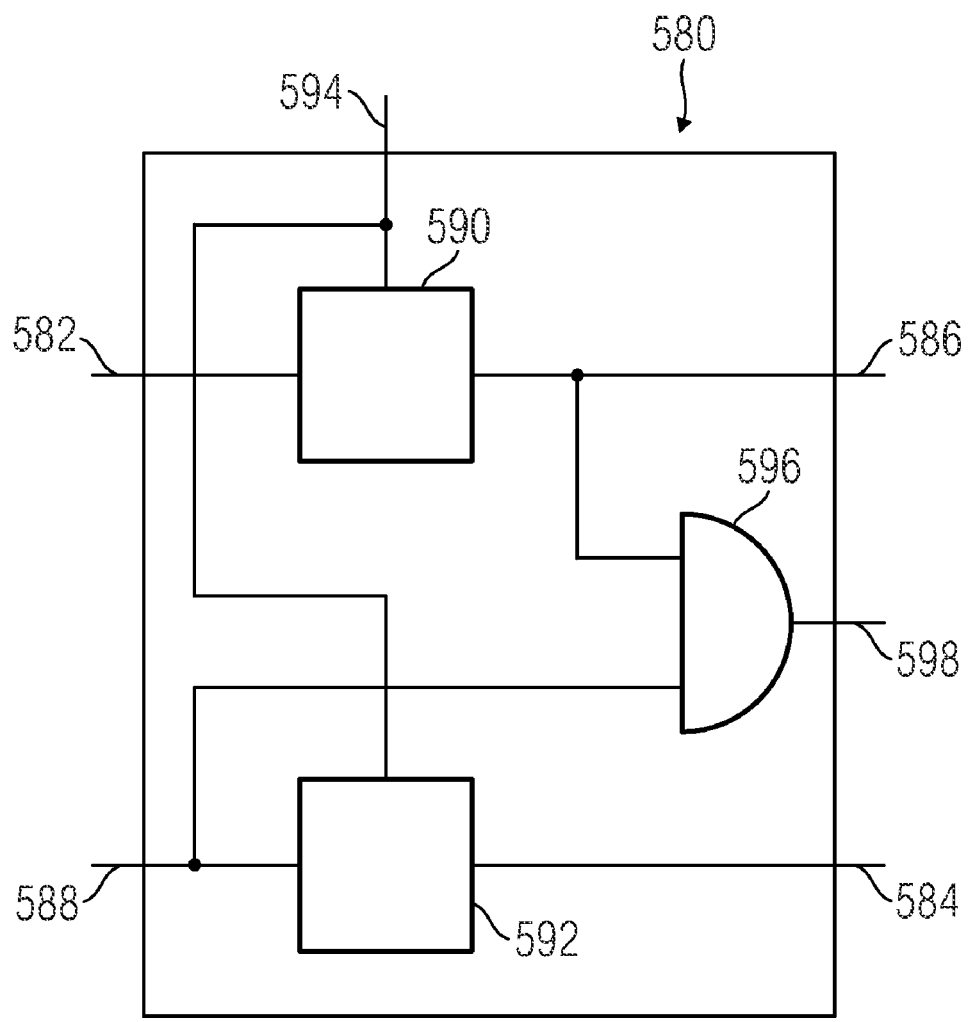

FIG. 5b moreover shows a circuit diagram of a column as it may, for example, be used in a multi-coincidence unit 500. A detailed description is omitted here, as the column 570 illustrated in FIG. 5b basically corresponds to a column j of coincidence cells 580 with regard to its setup (see FIGS. 5a and 5c).

Figure 6A:
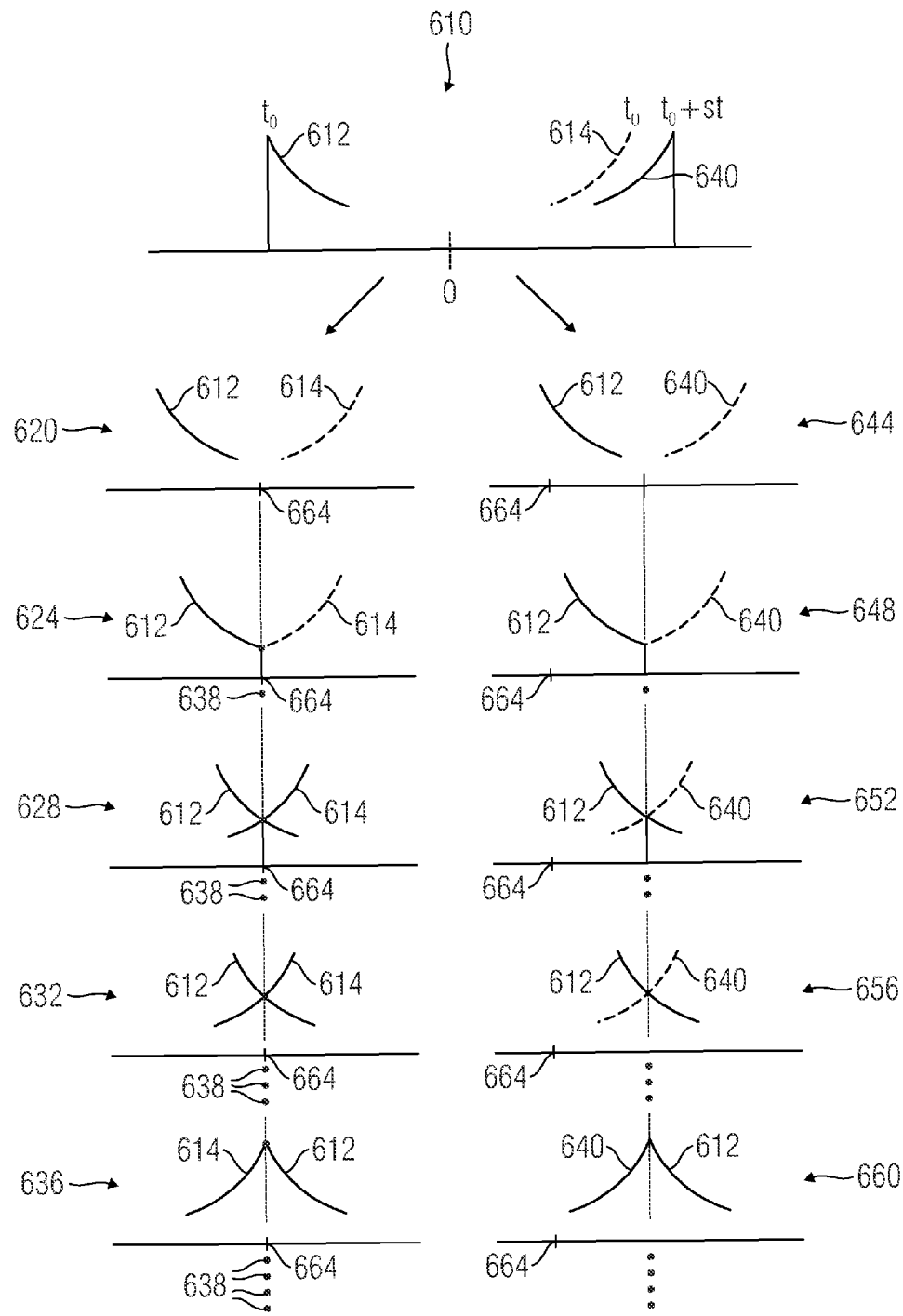
FIG. 6a shows a schematical illustration of a step-wise processing of two trajectories of the same curvature in an inventive multi-coincidence means without and with the presence of a time-shift between the trajectories.

FIG. 6a shows a schematical illustration of the processes in the multi-coincidence unit 500, when two trajectories of a first activity pattern and a second activity pattern are shifted through the multi-coincidence unit 500. It is here to be noted that shifting a trajectory through the multi-coincidence unit 500 in a graphical description corresponds to shifting the trajectory (for example by a column). Apart from that, it is to be noted that the trajectories illustrated in FIGS. 6a, 6b and 6c in the scope of an evaluation by the multi-coincidence unit 500 are represented by a plurality of parallel time signals. In a first graphical illustration 610, FIG. 6a shows a first trajectory 612 which is, for example, contained in the first activity pattern and which is assumed to be input into the multi-coincidence unit by a plurality of parallel signals of the first plurality 510 of parallel signals. The graphical illustration 610 further shows a second trajectory 614 in the second activity pattern. It is assumed that the second trajectory 614 in the second activity pattern is input into the multi-coincidence unit 500 by a plurality of parallel signals of the second plurality 512 of parallel binary signals. It is further assumed that the two trajectories 612, 614 have the same curvature and further occur simultaneously. The graphical illustrations 620, 624, 628, 632 show a step-by-step shifting of the trajectories 612, 614 through the stages of the multi-coincidence unit 500. As it is assumed that the trajectories 612, 614 have the same curvature and further occur simultaneously, in the course of shifting the trajectories 612, 614 a coincidence occurs in a middle column each of the multi-coincidence unit 500. When a shifting of the trajectories continues, coincidences occur in different lines of the multi-coincidence unit 500, however. The summator 530 belonging to the middle column of the multi-coincidence unit 500 thus increases its count when the shifting of the trajectories 612, 614 continues, as it is illustrated by the bold points 638 in the graphical illustrations 624, 628, 632, 636.

In the following it is assumed that instead of the trajectory 614 a trajectory 640 which is time shifted with regard to the same is input into the multi-coincidence unit. As the trajectory 640 is time-shifted with regard to the trajectory 612, the trajectory 612 has already been shifted further through the multi-coincidence unit than the trajectory 640 when a coincidence between the trajectory 612 and the trajectory 614 occurs. The corresponding circumstances are illustrated by the graphical illustrations 644, 648, 652, 656 and 660. A middle column of the multi-coincidence unit 500 is moreover designated by 664. In the graphical illustrations 644, 648, 652, 656, 660 it may be seen that, when the trajectory 640 which is time shifted with respect to the trajectory 612 is present, a coincidence between the shifted trajectory 612 and the shifted trajectory 640 occurs, wherein a location of the coincidence is shifted with regard to the middle column 664 of the multi-coincidence unit 500.

In other words, it is assumed that a first trajectory supplied to the multi-coincidence unit 500 via the first plurality 510 of parallel signals and a second trajectory 614, 640 supplied to the multi-coincidence unit 500 via a second plurality 512 of parallel signals have the same curvature, and thus a time shift between the first trajectory 612 and the second trajectory 614, 640 decides in what column j of the multi-coincidence unit 500 a coincidence occurs. In other words, information about a time shift between a first trajectory in the first activity pattern (supplied to the multi-coincidence unit via the first plurality 510 of parallel signals) and a second trajectory in the second activity pattern (supplied to the multi-coincidence unit 500 via the second plurality 512 of parallel signals) may be derived from the fact at what column of the multi-coincidence unit the coincidence occurs.

Figure 6B:
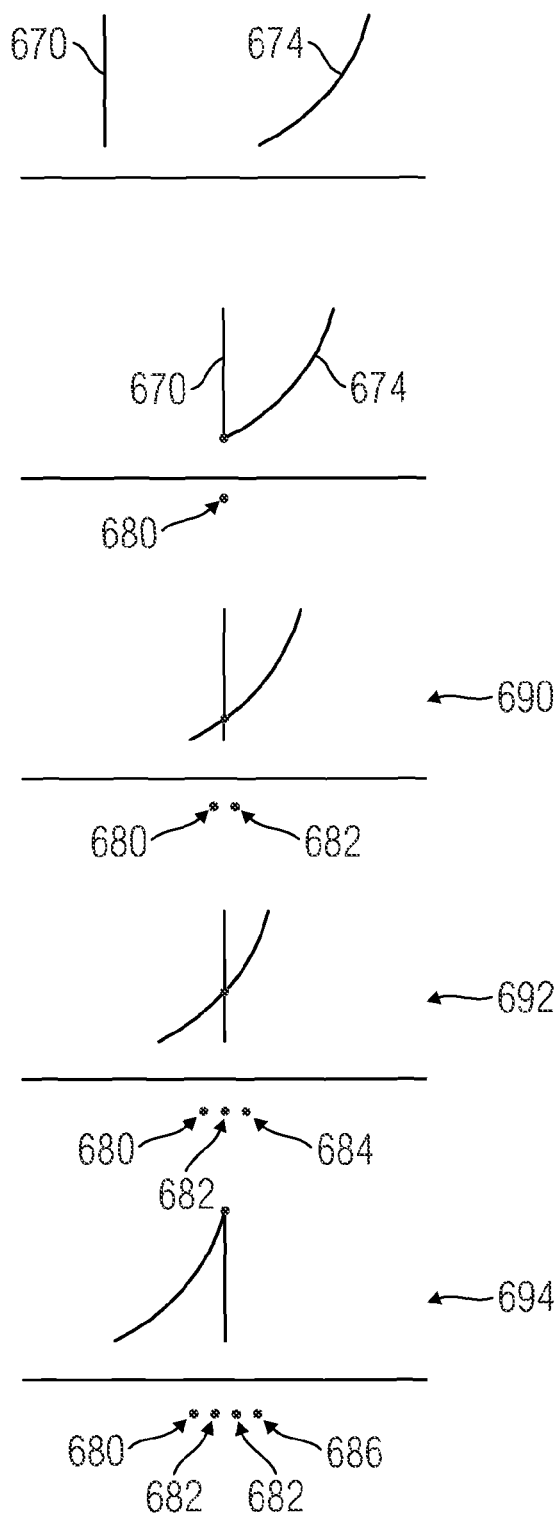
FIG. 6b shows a schematical illustration of a step-wise processing of two trajectories of a different curvature in an inventive multi-coincidence means.

FIG. 6b shows a schematical illustration of the ratios resulting in the multi-coincidence unit 500 when the multi-coincidence unit 500 is pulsed with a first trajectory 670 contained in the first activity pattern and with a second trajectory 674 which is contained in the second activity pattern, wherein it is assumed that the first trajectory 670 and the second trajectory 674 comprise a different curvature. In the illustrated extreme example according to FIG. 6b, it is assumed for reasons of clarity that the first trajectory 670 is not curved or straight, respectively. If the first trajectory 670 and the second trajectory 674 are shifted in opposite directions by the multi-coincidence unit 500 as described above, then a first coincidence occurs in a column of the multi-coincidence unit 500 which is designated here by 680. If the trajectory 670 is shifted further in the first direction, while the trajectory 674 is shifted further in the opposite direction, a next coincidence does not occur in column 680, but typically in an adjacent column 682 of the multi-coincidence unit 500 (see graphical illustration 690). After a further shifting of the trajectories 670, 674, finally a coincidence occurs in a column 684 which is typically adjacent to the column 682 (see graphical illustration 692). A further continuation of the shifting is illustrated in the graphical illustration 694, wherein a coincidence in yet a further column 686 results.

In other words, the multi-coincidence unit 500 is implemented such that coincidences occur in the same column each when trajectories of the same curvature are shifted in opposite directions step by step through the multi-coincidence unit 500. If trajectories of a different curvature are shifted step by step through the multi-coincidence unit 500, however, coincidences occur in different columns.

In one embodiment, the threshold value of the threshold value decider 540 is set so that the threshold value decider 540 only responds (or outputs an active output signal, respectively) when trajectories of the same curvature (or with different curvatures which deviate from each other by no more than a predetermined maximum deviation) are shifted in opposite directions through the multi-coincidence unit 500.

In other words, the multi-coincidence unit 500 is implemented so that the occurrence of an active output signal at any of the threshold value deciders 540 indicates that in the first activity pattern and the second activity pattern two trajectories of approximately (within a predetermined tolerance range) the same curvature are present. From the fact, which of the threshold value deciders 540 gives out an active signal at its output, further information about a time shift between the trajectories of the same curvature result.

It is to be noted, however, that the multi-coincidence unit 500 may be replaced by any other means which is able to detect trajectories (or in line-shaped geometrical forms, respectively) in a first activity pattern and in a second activity pattern which comprise at least approximately (i.e. for example within the same tolerance range) the same curvatures, to determine a time shift between the trajectories having the same or approximately the same curvature. It is further possible, apart from the curvature of the trajectories in the first activity pattern and in the second activity pattern, to further use a length of the trajectories in the first activity pattern and in the second activity pattern in order to decide whether a first trajectory in the first activity pattern and a second trajectory in the second activity pattern are associated with the same sound event.

Figure 7:
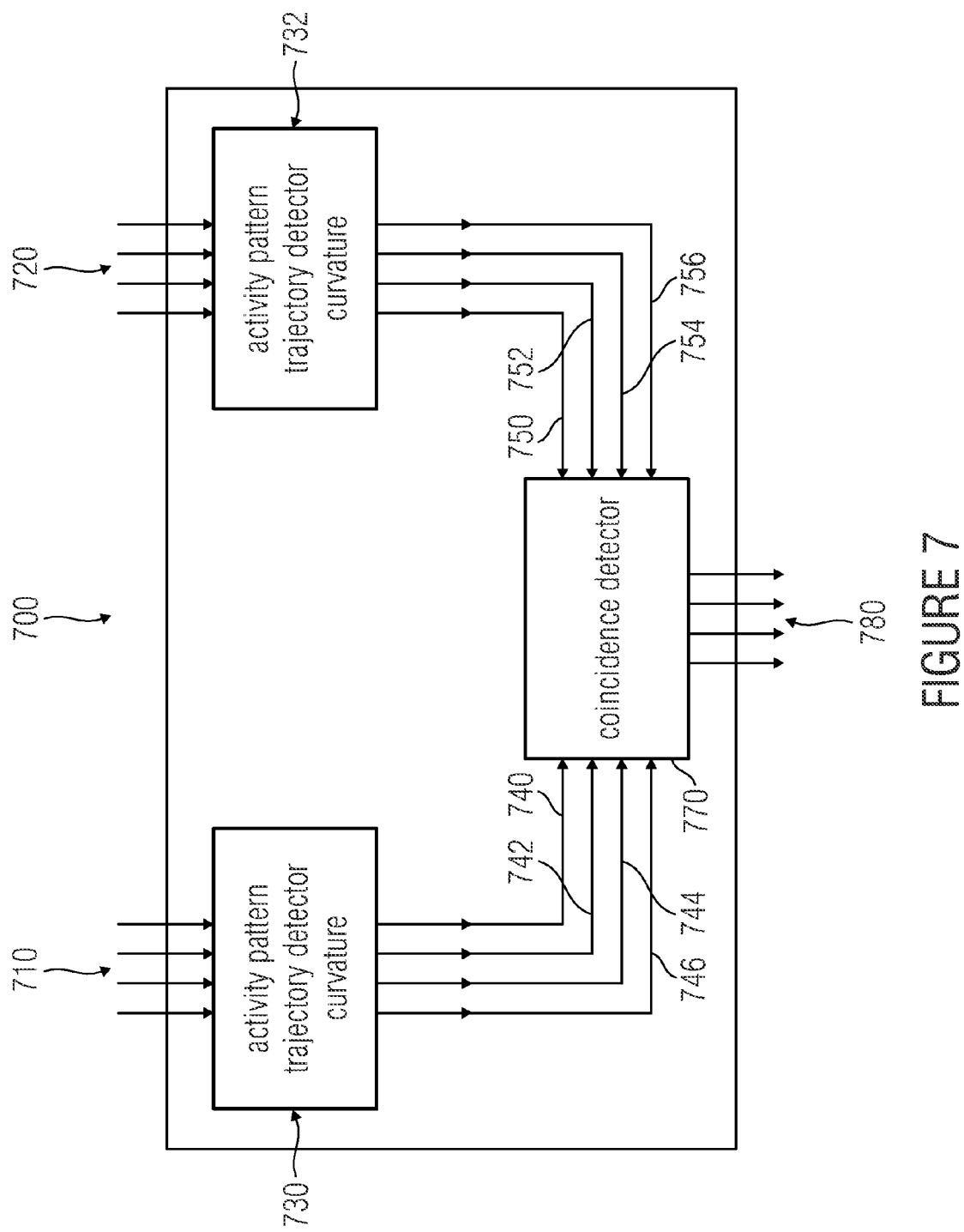
FIG. 7 shows a block diagram of an inventive identifier for identifying trajectories in two activity patterns according to one embodiment of the present invention.

FIG. 7 shows a block diagram of an inventive identifier according to an embodiment of the present invention. The identifier according to FIG. 7 is designated by 700 in its entirety. The identifier 700 is implemented to receive a first activity pattern in the form of a first plurality 710 of parallel signals or parallel information, respectively. Further, the identifier 700 is implemented to receive a second activity pattern in the form of a second plurality 720 of parallel signals. The description of the activity patterns by the parallel signals 710, 720 may here, for example, be executed by binary signals, wherein active states indicate the occurrence of an activity event.

The identifier 700 includes a first trajectory detector 730 and a second trajectory detector 732. The first trajectory detector 730 is implemented to receive the first activity pattern via the first plurality 710 of parallel signals and to detect trajectories in the first activity pattern. For example, the first trajectory detector 730 is implemented to detect line-shaped structures in the first activity pattern which comprise a certain predetermined curvature. For example, the trajectory detector may be implemented to detect line-shaped structures with a plurality of different predetermined curvatures. An example of a trajectory detector is moreover described later with regard to FIGS. 8, 9 and 10. Analogously, the second trajectory detector 732 is implemented to receive the second activity pattern via the second plurality 720 of parallel signals. The second trajectory detector 732 is here, for example, implemented to detect trajectories of a different curvature.

For example, the first trajectory detector 730 is implemented to activate an output line based on the first activity pattern so that the fact, which one of the several output lines is activated, includes information about a curvature of a trajectory identified in the activity pattern. In other words, if the trajectory detector 730 detects a trajectory in the first activity pattern, the trajectory detector activates one (but possibly also more than one) of its output lines 740, 742, 744, 746 depending on the curvature of the trajectory. Further, the second trajectory detector 732 is implemented, for example, to activate at least one (exactly one, but possibly also several) of its output lines 750, 752, 754, 756 depending on a curvature of a trajectory detected in the second activity pattern. Here, the first trajectory detector 730 and the second trajectory detector 732 are implemented so that corresponding output lines of the two trajectory detectors 730, 732 show the same curvature of trajectories (within a tolerance range). In other words, an $i^{th}$ output signal of the first trajectory detector 730 indicates the presence of a trajectory with a certain $i^{th}$ curvature in the first activity pattern, and an $i^{th}$ output signal of the second trajectory detector 732 indicates the presence of a trajectory with the same $i^{th}$ curvature in the second activity pattern.

The identifier 700 further includes a coincidence detector 770. Regarding its setup, the coincidence detector 770 for example corresponds to the multi-coincidence unit 500. The coincidence detector 700, for example, receives the output signals 740, 742, 744, 746 of the first trajectory detector 730 as input signals at the first plurality 510 of inputs. The coincidence detector 770 further receives the output signals 750, 752, 754, 756 of the second trajectory detector 732 at the inputs of the second plurality 512 of inputs. It is assumed here that the $i^{th}$ output signal of the first trajectory detector 730 and the $i^{th}$ output signal of the second trajectory detector 732 are supplied to the $i^{th}$ line of the multi-coincidence unit 500. If the first trajectory detector 730 and the second trajectory detector 732 thus detect trajectories of the same curvature, the first trajectory detector 730 and the second trajectory detector 732 activate corresponding output signals (for example each $i^{th}$ output signal). Thus, for example, in the $i^{th}$ line of the multi-coincidence unit 500 (which forms the coincidence detector 770) a coincidence occurs. The fact in what column j of the multi-coincidence unit 500 the coincidence occurs represents a measure of how great a time shift between the trajectories of the same curvature is.

In other words, the mere occurrence of a coincidence in a coincidence cell of the multi-coincidence unit 500 already indicates the presence of trajectories of the same curvature at the identifier 700. Thus, for example when using the multi-coincidence unit 500 as a coincidence detector 770, the threshold value decider 540 and also the summators 1530 may optionally be omitted. The coincidence detector 770 thus provides a plurality of parallel output signals which indicate with what time shift trajectories of the same curvature occur. The output signals of the coincidence detector 770 are designated by 780.

Thus, the circuitry 700 represents a further alternative to determine, based on two activity patterns, whether in the two activity patterns trajectories of the same curvature (i.e. trajectories associated with the same sound events) are present and, if so, what time shift these trajectories comprise.

Apart from that, it is to be noted that in an embodiment when using the multi-coincidence unit 500 instead of the coincidence detector 770, the summators 530 may be replaced by an OR operation so that the output signals of the OR operations form the output signals 780 of the coincidence detector 770 or the identifier 700, respectively.

In the following, with reference to FIGS. 8, 9 and 10 different devices will be described which may, for example, be used as trajectory detectors and which may thus occur in certain embodiments of the present invention instead of the trajectory detectors 730, 732.

Figure 8:
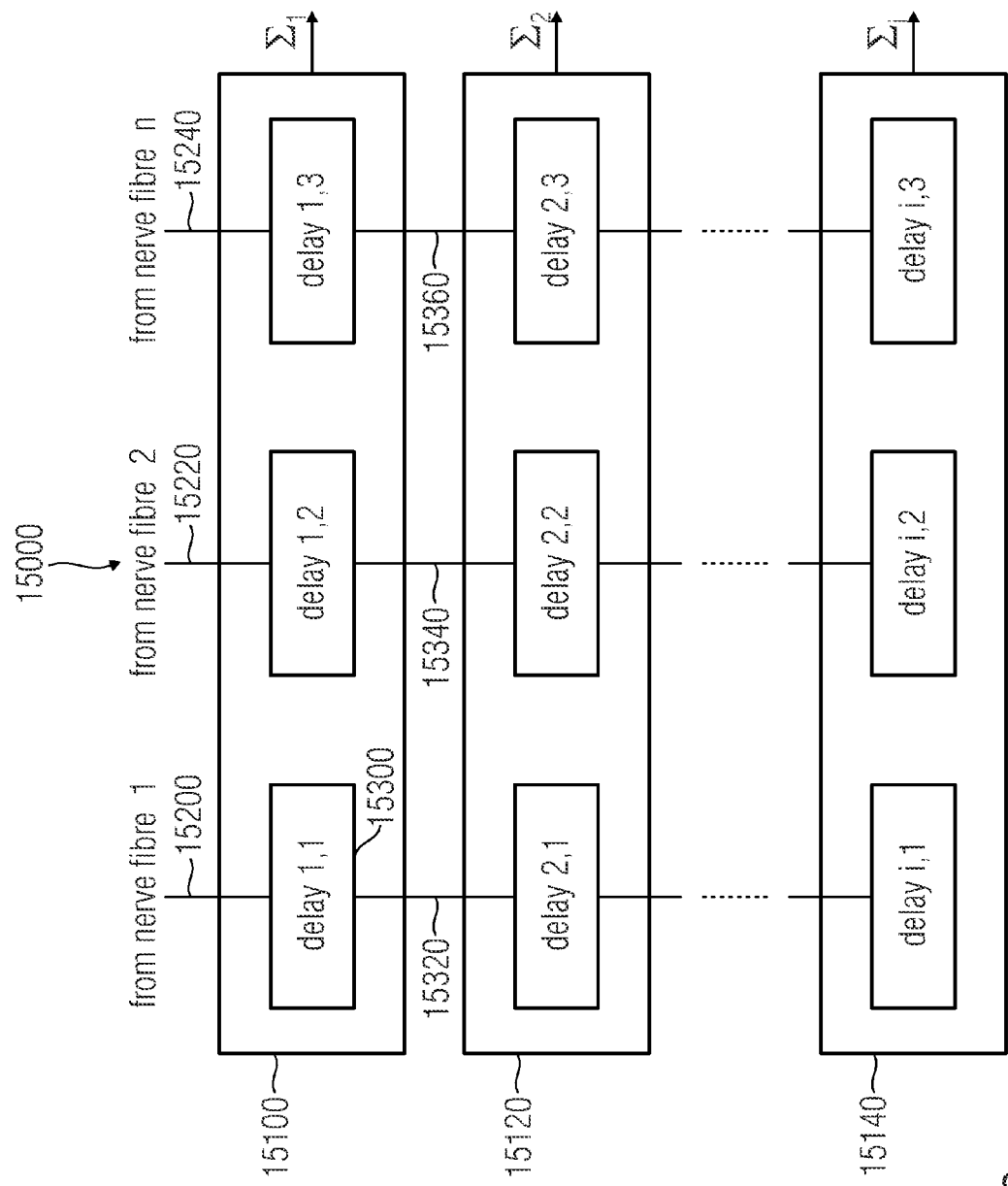
FIG. 8 shows a block diagram of a device for the inventive execution of a pattern recognition based on an activity pattern.

FIG. 8 shows a block diagram of a device for an inventive processing of the neural activity pattern. The device indicated in FIG. 8 is designated by 15000 in its entirety. The illustrated device 15000 comprises a plurality of stages 15100, 15120, 15140, wherein the first stage 15100 receives parallel signals 15200, 15220, 15240 from nerve cells. The signals 15200, 15220, 15240 describe an activity pattern (e.g. action potentials on nerve fibers coupled to the corresponding nerve cells or inner hair cells, respectively, or neurotransmitter vesicle occurrence at a plurality of inner auditory cells). The signals 15200, 15220, 15240 thus for example describe the neural activity pattern. The signals may, however, also describe another activity pattern, for example a neurotransmitter vesicle occurrence in a plurality of inner hair cells.

In a first stage 15100 the first signal or nerve signal 15200, respectively, is then, for example, subjected to a delay in a first delay means 15300 and then passed on as a delayed signal or nerve signal 15320 to a second stage 15120. In a similar way, also the second signal or nerve signal 15220, respectively, is delayed in the first stage 15100 and passed on as a delayed signal or nerve signal to the second stage 15120. In the same way, also the remaining signals or nerve signals, respectively, are processed in the first stage 15100 (i.e. for example also the $n^{th}$ signal or nerve signal 15240, respectively).

The second stage 15120 is implemented in parallel to the first stage 15100, i.e. again enables the delayed forwarding of the delayed signals or nerve signals 15320, 15340, 15360, respectively, whereby twice delayed signals or nerve signals, respectively, result. A device for the inventive processing of the activity pattern includes a plurality of series-connected stages set up like the first stage 15100 or the second stage 15120, respectively. The signals or nerve signals 15200, 15220, 15240, respectively, are passed on in parallel through the plurality of stages 15100, 15120, 15140, wherein each stage adds a settable delay to the signals or nerve signals, respectively.

Further, each of the stages 15100, 15120, 15140 is implemented to form a sum of its incoming or outgoing signals or nerve signals, respectively (or m-times delayed nerve signals, respectively). Further, the stages 15100, 15120, 15140 are implemented to compare this sum to a settable threshold value in order to determine whether at a certain point in time at least a predetermined number of signals or nerve signals or delayed signals or nerve signals, respectively (i.e. incoming signals or nerve signals, respectively, or outgoing signals or nerve signals, respectively) are active (or, respectively, comprise an action potential).

It is further advantageous that the delays of the delay means present in the stages 15100, 15120, 15140 are set differently so that, for example, a first signal or nerve signal 15200, respectively, is subject to a different delay when passing the stages 15100, 15120, 15140 than the second signal or nerve signal 15220, respectively. Delays may, for example, be set such that for the signals or nerve signals 15200, 15220, 15240, respectively, different overall delays result when passing through the stages 15100, 15120, 15140 (wherein it is of course allowed that for example two signals or nerve signals, respectively, are delayed in the same way). In other words, the means 15000 is implemented such that the same delays do not result for all signals or nerve signals, respectively. Apart from that, it is advantageous that in the presence of j stages 15100, 15120, 15140 at least (j−1) stages 15100, 15120 are implemented such that delay means contained in one stage for the plurality of signals do not all comprise the same delay. In this way it may be achieved that an activity pattern entering an inventive means 15000 over time when passing through the described means is distorted with regard to time so that individual signals or nerve signals, respectively, are time shifted with regard to other signals or nerve signals, respectively. By the distortion in a temporal illustration bent line-like patterns, i.e. trajectories, may be bent to be straight in the activity pattern.

It is further to be noted that by the summation within a stage it may be detected when an originally bent trajectory was bent into a straight line in the activity pattern (wherein a straightened line is described or detected, respectively, by the fact that a predetermined number of the delayed signals or nerve signals, respectively, comprise an active stage or an action potential virtually simultaneously or overlapping in time, respectively).

Figure 9:
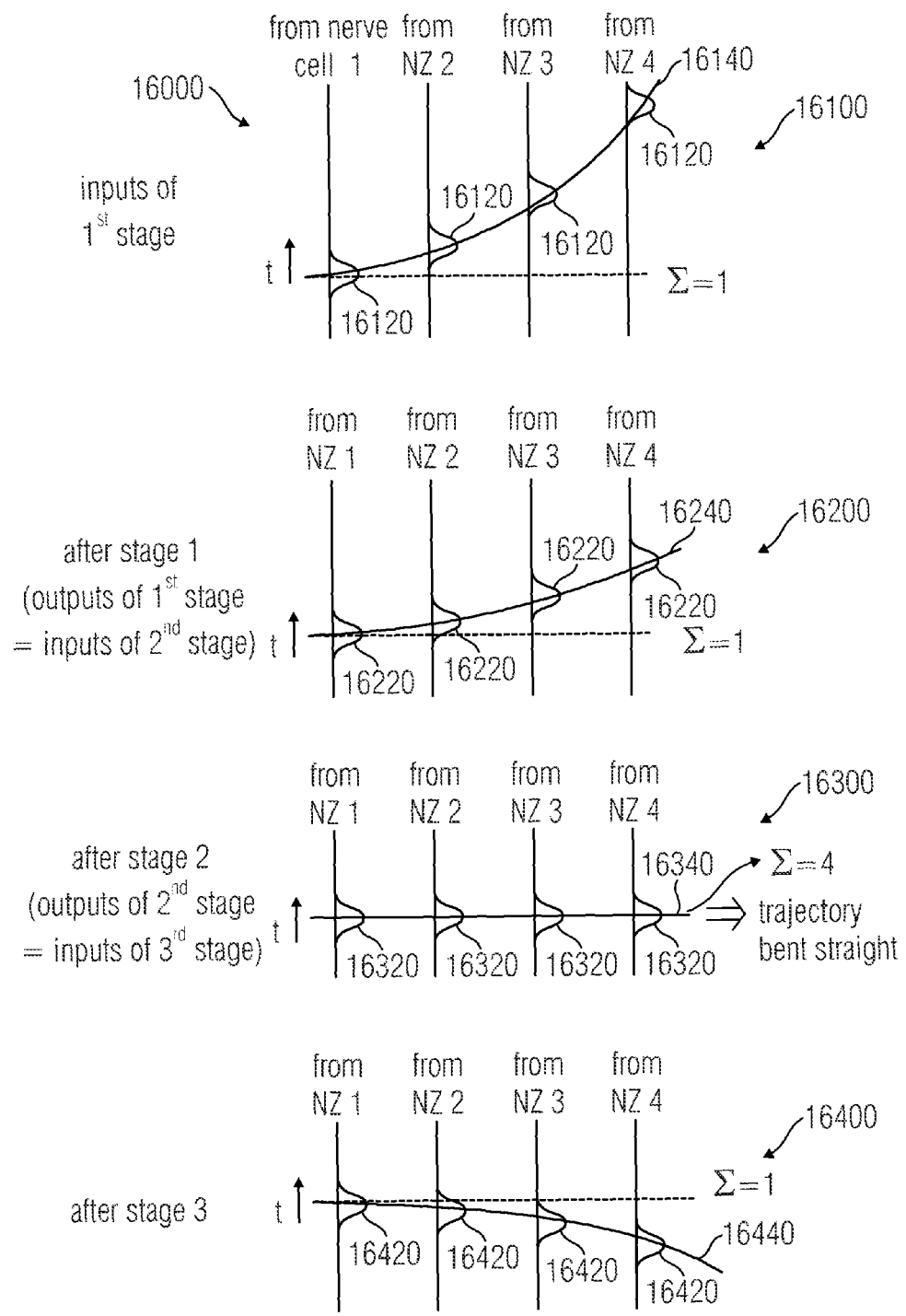
FIG. 9 shows a graphical illustration of signals in a device for the inventive execution of a pattern recognition.

The functioning of the means 1500 is to be illustrated with regard to FIG. 9. FIG. 9 shows an exemplary graphical illustration of the signals in a device 15000 for an inventive processing of the activity pattern. The graphical illustration of FIG. 9 is designated by 16000 in its entirety.

A first graphical illustration 16100 here describes an exemplary activity pattern at inputs of the device 15000. As an example, the signals of four nerve cells (or on four nerve fibers, respectively) are shown in a time course. Apart from that, it is to be noted that the action potentials 16120 form a trajectory 16140. As it is illustrated, the trajectory 16140 comprises a strong curvature in the temporal illustration, as the action potentials 16120 of the different nerve fibers comprise a substantial time offset at the inputs of the first stage 15100. Thus, in the first stage 15100 at a fixed point in time only one action potential each is present, so that a threshold value for a sum of the action potentials applied to the first stage, which is, for example, set to two, is not exceeded. Consequently, the first stage does not provide an output signal at a threshold value output.

A second graphical illustration 16200 describes the conditions at an output of the first stage 15100. It is assumed here that in the first stage 15100 the nerve signal provided by the first nerve cell NZ1 is delayed more strongly than the nerve signals provided by the other stages. Apart from that, it is assumed that, in the given example, the nerve signal provided by the fourth nerve cell NZ4 is delayed least, while the nerve signal from the third nerve cell NZ3 is delayed a little more and wherein the delay for nerve signals from the nerve cells NZ2 and NZ1 continually increases. Generally speaking, signals belonging to nerve cells which respond to a lower frequency are delayed less than nerve signals from nerve cells detecting higher frequencies.

The second graphical illustration thus shows again action potentials 16240 as a function of time, wherein the action potentials 16220 form a trajectory 16240. As it may be seen from the second graphical illustration 16200, the curvature of the trajectory 16240 at the outputs of the first stage is less than a (temporal-spatial or temporal-frequency, respectively) curvature of the trajectory 16160 at the inputs of the first stage. This results from the different delays of the nerve signals belonging to different nerve cells in the delay means (e.g. 15300) of the first stage. By this, a bent trajectory is so to speak bent to be straight. As it may be seen from the second graphical illustration 16200, the second trajectory 16240 comprises a residual curvature, however, so that the action potentials 16220 coming from different nerve cells or nerve fibers, respectively, are not all simultaneously applied to the outputs of the first stage 15100 or inputs of the second stage 15120, respectively.

Also the second stage 15120 causes a further delay, wherein again signals from nerve cells which are sensitive with regard to low frequencies are delayed less than signals from nerve cells which are sensitive with regard to higher frequencies. A third graphical illustration 1630 shows the nerve signals at outputs of the second stage which are delayed again in the second stage 15120. It may be seen from the third graphical illustration 16300 that in the present example the nerve signals at the outputs of the second stage are each delayed so that action potentials 16320 from several nerve cells are simultaneously applied to the outputs of the second stage. In other words, a trajectory 16340 described by the action potentials 16320 is at least approximately bent to be straight. The action potentials 16320 thus occur simultaneously or approximately simultaneously, respectively (but at least overlapping in time) so that the simultaneous occurrence comprises a clear peak which is high enough to exceed a predetermined threshold value (e.g. two or three) by a summation of the signals applied at the outputs of the second stage (or inputs of the third stage, respectively).

In other words, it may be detected by a suitable summation means (or another suitable means) when a curved trajectory was bent to be straight. The corresponding information enables a conclusion to be reached regarding both the starting time of the trajectory and also the form of the trajectory. It may be determined, after passing how many stages a trajectory was bent straight. By this, when knowing the delays for the individual nerve signals in the stages of means 15000, a conclusion may be drawn concerning an original form of the trajectory. Further, the run-time for the stages is known, so that also the time at which a trajectory entered into means 15000 may be determined. Thus, both characteristic time information of the trajectories and also information about the shape or curvature of the trajectories, respectively, may be determined in order to determine which activity events belong to a trajectory and/or which activity events do not belong to a trajectory.

Apart from that, it is to be noted that a fourth graphical illustration 16400 for improving clarity shows output signals at outputs of a third stage. Action potentials 16420 describe a trajectory 16440 which is, however, bent again by a further bending of the trajectory.

It is further to be noted that the delay in stages 15100, 15120, 15160 may be achieved in different ways. The delay means (e.g. 15300) may, for example, be clocked and/or they may be continuously or discretely settable delay means. Apart from that, it is also possible that one or several delay means are deactivated in a predetermined stage for one or several nerve signals, so that some of the nerve signals are passed on by a stage with a least possible delay. Apart from that it is to be noted, that the means 15000 may all in all be implemented as an analog or digital circuit.

It is further to be noted that an evaluation of a neural activity pattern was described above. The device 15000 may, however, also be used for finding trajectories in any activity patterns.

It is further to be noted that the signals 15200, 15220, 15240 correspond, for example, to the signals 710 or 720, respectively. The threshold value-evaluated sum signals $\Sigma_1$, $\Sigma_2$, $\Sigma_i$ (resulting from a comparison of the sum signals to a threshold value) correspond to the signals 740, 742, 744, 746 or 750, 752, 754, 756, respectively.

Figure 10:
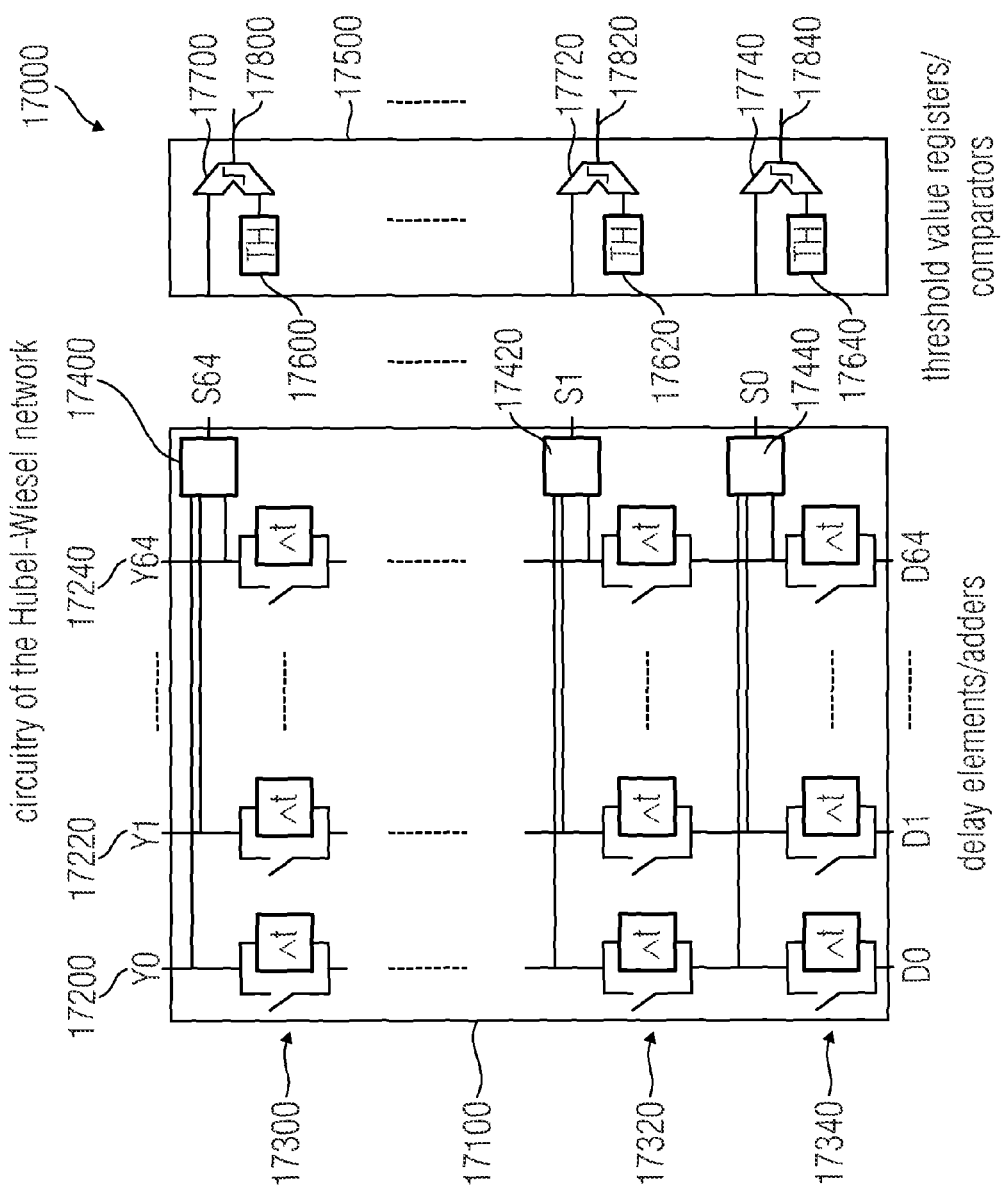
FIG. 10 shows a circuit diagram of a Hubel-Wiesen network for the inventive execution of a pattern recognition.

FIG. 10 shows a circuit diagram of an exemplary Hubel-Wiesel network for the inventive calculation of an analysis illustration of an audio signal according to the second embodiment of the present invention. The circuit diagram of FIG. 17 is designated by 17000 in its entirety. A first circuit block 17100 receives input signals 17200, 17220, 17240 which may, for example, represent a neural activity pattern, an excitation pattern of a basilar membrane or a neurotransmitter vesicle occurrence. The input signals 17200, 17220, 17240 are then guided through a plurality of stages 17300, 17320, 17340. An input signal 17200 thus passes a plurality of stages 17300, 17320, 17340, wherein an input signal 17200 in one stage 17300, 17320, 17340 either passes a delay means or is directly passed on to a subsequent stage. In other words, the delay means may also be bridged.

In other words, each stage for each signal includes a switchable delay means, wherein the delay means may be switched into a signal path which is passed by an input signal or may be bridged. Signals at the inputs of each stage are tapped and supplied to summators 17400, 17420, 17440, wherein the signals applied to the inputs of one stage are each summated. The first circuit block 17100 thus forms a grid of delay elements and adders, interconnected in the illustrated way.

The Hubel-Wiesel network 17000 further comprises a threshold value means 17500, wherein one value each is supplied from a threshold value register 17600, 17620, 17640 and an output of a summator 17400, 17420, 17440 to a comparator 17700, 17720, 17740. Output signals 17800, 17820, 17840 of the comparators 17700, 17720, 17740 here provide an indication whether at the inputs of a predetermined stage 17300, 17320, 17340 a number of signals is active simultaneously, wherein a minimum number for which an active output signal 17800, 17820, 17840 is output is determined by the threshold value registers 17600, 17620, 17640. In other words, by the comparators 17700, 17720, 17740 in connection with the summators 17400, 17420, 17440 and the threshold value registers 17600, 17620, 17640 it may be determined when (or after passing how may of the stages 17300, 17320, 17340, respectively) a trajectory which was read in via the inputs 17200, 17220, 17240 of the first block 17100 is bent straight.

The delays of the individual stages 17300, 17320, 17340 may here be suitably predetermined to enable a detection of a number of trajectories (or trajectory forms, respectively) which is as high as possible.

The input signals 17200, 17220, 17240 for example correspond to the signals 710, 720 according to FIG. 7, while the output signals 17800, 17820, 17840 for example correspond to the signals 740, 742, 744, 746 or to the signals 750, 752, 754, 756, respectively, according to FIG. 7.

In the following it will be described with reference to FIG. 11 how an activity pattern may be calculated for use within the scope of the present invention based on an auditory model of a human ear. It is to be noted that an activity pattern represents a description of an activity in or at a plurality of auditory cells of an auditory model or at a plurality of auditory nerves of an auditory model. In the following it will be described which intermediate variables may, for example, be calculated in the evaluation of an auditory model of an ear. Each of the intermediate variables is, for example, suitable for determining an activity pattern, wherein an activity event is given when the corresponding intermediate variable deviates from a quiescent value resulting without the presence of an audio signal by more than a predetermined value. In other words, an activity event is present when one of the intermediate variables or final variables mentioned in the following exceeds or lies below a predetermined threshold value. Apart from that, it has turned out that for the formation of the activity pattern the transmitter release rate 2680, the neurotransmitter vesicle occurrence 2760 and the neural activity pattern 2840 are especially suitable.

Details of the calculation of the given variables using an advanced auditory model are indicated in the following. It is, however, to be noted that for the calculation of the activity pattern and or the activity patterns, respectively, also other auditory models are suitable in which one or more of the intermediate variables are calculated in another way, or in which the calculation of one or several intermediate variables is omitted.

Figure 11:
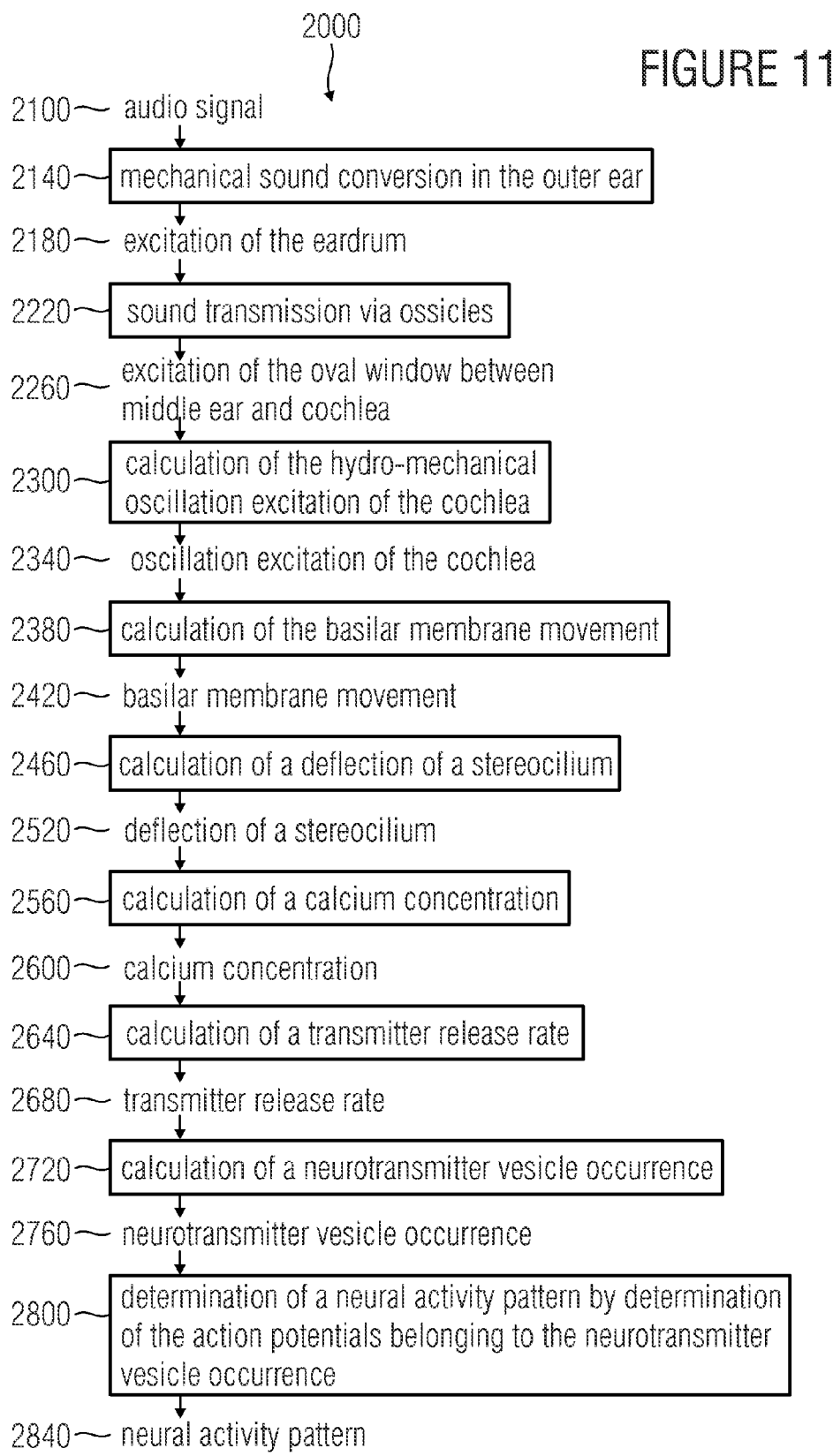
FIG. 11 shows a schematical illustration of a course of events in a simulation of a human hearing and in the simulation of occurring intermediate and final results.

For this purpose, FIG. 11 shows a schematical illustration of the operating sequences in a simulation of a human hearing and of intermediate and final results occurring in the simulation. The schematical illustration of FIG. 11 is designated by 2000 in its entirety. In other words, FIG. 11 describes an auditory model of a human ear for use in connection with the present invention.

The schematical illustration 2000 of FIG. 11 thus describes a simulation model of the human hearing system. An audio signal 2100 serves as an input signal for the simulation model 2000. Based on the audio signal 2100, in a first step 2140 a mechanical sound conversion in an outer ear is evaluated, whereby an excitation 2180 of an eardrum is determined. In a second step 2220, a sound transmission via ossicles is calculated or simulated, respectively, whereby from the excitation 2180 of the eardrum an excitation 2260 of an oval window between a middle ear and a cochlea is determined. In a third step 2300, a hydromechanical oscillation excitation 2340 of the cochlea is calculated or simulated, respectively. In a fourth step 2380, from the oscillation excitation 2340 of the cochlea a basilar membrane movement 2420 is determined. In a fifth step 2460, a conclusion is drawn from the basilar membrane movement 2420 to a deflection 2520 of a stereocilium. Based on the deflection 2520 of the stereocilium, then in a sixth step 2560 a calcium concentration 2600 in a hair cell is calculated. The calcium concentration 2600 is then used in a seventh step 2640 to calculate a transmitter release rate 2680 of transmitter substances. Based on the transmitter release rate 2680, in an eighth step 2720 a neurotransmitter vesicle occurrence 2760 is derived which describes an occurrence of neurotransmitter vesicles. Finally, in a ninth step 2800 a neural activity pattern 2840 is deduced from the neurotransmitter vesicle occurrence 2760. The neural activity pattern 2840 here describes approximately an activity occurring with a healthy hearing on nerve cells of an (human or animal) auditory nerve. The neural activity pattern 2840 is thus well suited for providing a statement about a stimulation of auditory nerves by a cochlear implant.

It is to be noted that, within the scope of the simulation model 2000, several of the steps 2140, 2220, 2300, 2380, 2460, 2560, 2640, 2720, 2800 may be combined without calculating a corresponding intermediate result. In other words, several steps may be processed in a simplified step without calculating the intermediate steps illustrated in the graphical illustration 2000.

The deflection 2520 of a stereocilium as well as the calcium concentration 2600 in an inner hair cell, the transmitter release rate 2680 in an inner hair cell, a neurotransmitter vesicle occurrence 2760 in an inner hair cell or a neural activity pattern 2840 applied to the inner hair cell (or its associated temporal course, respectively) may each represent an activity pattern or a part of an activity pattern, respectively, at an inner hair cell.

Likewise, for example the concentrations 2600 of calcium ions may form an activity pattern in a plurality of inner hair cells. An activity event, when considering the calcium concentration, is, for example, a significant rise of the calcium concentration beyond a certain threshold value or a decrease of the calcium concentration below a certain threshold value.

Apart from that, the activity pattern may, for example, also describe a deviation of the current calcium concentration from balance calcium concentrations. An activity event is in this case described by a significant deviation of the respective calcium concentrations to the top or to the bottom, respectively.

Further, also the time course of a transmitter release rate 2680 or a transmitter release probability may be used in a plurality of inner hair cells as an activity pattern over time. The activity pattern is here formed by the transmitter release rate or the transmitter release probability in the $i^{th}$ inner hair cell.

Apart from that, it is to be noted that, when considering the transmitter release rate 2680 or transmitter release probability, respectively, for example the presence of a neurotransmitter release rate greater than zero or a transmitter release probability greater than zero, respectively, may be regarded as an activity event.

Further, also a neurotransmitter vesicle occurrence 2760 may form an activity pattern in a plurality of inner hair cells. In other words, an activity pattern in the mentioned case describes how many neurotransmitter vesicles are, for example, released during a certain time or time interval, respectively. The neurotransmitter vesicle occurrence 2760 may, however, also describe how many neurotransmitter vesicles are newly released during a time or a time interval, respectively. The respective time course may, for example, further describe how many neurotransmitter vesicles are released in the presynaptic inner hair cell in a time unit or exist in a time interval or at a point in time in a released form. Further, the neurotransmitter vesicle occurrence 2760 may also describe how many neurotransmitter vesicles diffuse, for example, per time unit from the presynaptic inner hair cell into the synaptic cleft which couples the presynaptic inner hair cell to a nerve fiber.

In other words, a neurotransmitter vesicle occurrence is, for example, the number of neurotransmitter vesicles actually present or released per time unit, wherein it is not relevant for the present invention exactly where in a hair cell or synapse the corresponding number of neurotransmitter vesicles or the corresponding release rate of neurotransmitter vesicles is determined. It is to be assumed that neurotransmitter vesicles released in the presynaptic part of the inner hair cell diffuse into the synaptic cleft with a certain time constant.

Apart from that, it is to be noted that a neurotransmitter vesicle occurrence may be described regarding both quality and quantity in order to describe an activity pattern in the sense of the present invention. In other words, a time course belonging to a neurotransmitter vesicle occurrence 2760 may, for example, describe how many neurotransmitter vesicles are released or are present in a released form. The course may only give qualitative information on whether neurotransmitter vesicles are released in a time interval or are present in a released form, respectively.

When regarding a neurotransmitter vesicle occurrence 2760 in or at a plurality of inner hair cells of an auditory model as the activity pattern, for example the release of a number of neurotransmitter vesicles in a time unit which is greater than a certain threshold value may be regarded as the activity pattern. It may, for example, be assumed that an activity event occurs when a neurotransmitter vesicle is released within a time interval. Further, it may be assumed that an activity event exists when at least one (or more generally: more than a predetermined minimum number) free neurotransmitter vesicle is present in an inner hair cell.

In other words, an activity event is an event which occurs in a single inner hair cell. An activity event typically may be noticed from a local minimum or maximum of the activity pattern or from exceeding or falling below a threshold value, respectively.

Further, also a neural activity pattern at a plurality of inner hair cells of an auditory model may be used as an activity pattern. The neural activity pattern here describes the activity or the time course of the activity, respectively, on several different nerve fibers, which are coupled to several different inner hair cells. For example, a temporal course of a potential or a voltage, respectively, of a nerve cell coupled to an $i^{th}$ inner hair cell is associated to an $i^{th}$ time course of the activity pattern. Action potentials, whose occurrence is described by the activity pattern, occur here on the individual nerve fibers. An activity event in this case is the occurrence of an action potential on one of n considered nerve fibers.

All in all, it may be said that, in a method according to flowchart 2000, different quantities 2520, 2600, 2680, 2760 may be calculated for a plurality of different inner hair cells, wherein an activity pattern is formed by the combination of the same quantity for a plurality of different hair cells.

Figure 12:
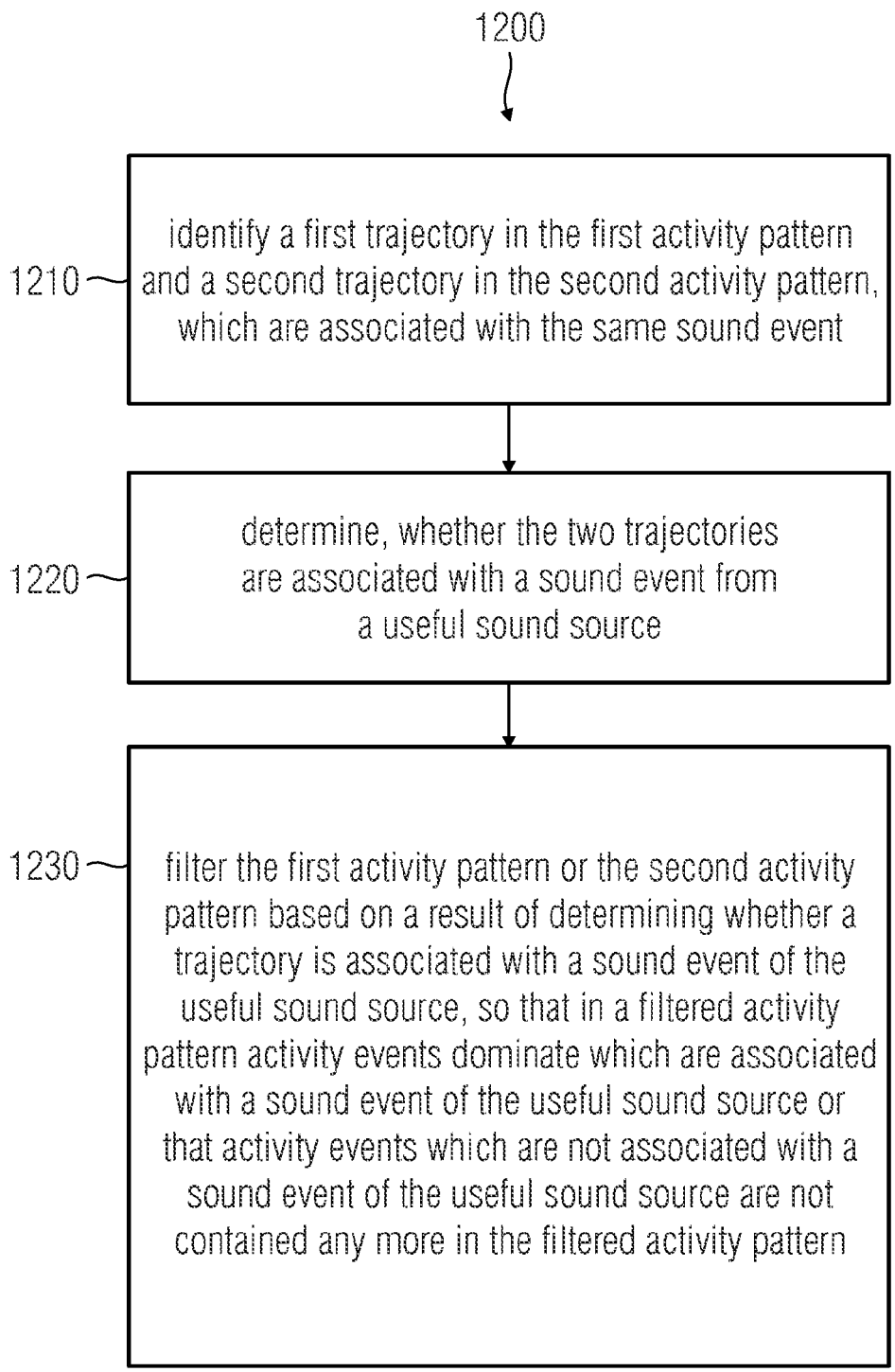
FIG. 12 shows a flowchart of an inventive method for generating a filtered activity pattern according to an embodiment of the present invention.

Apart from that, FIG. 12 shows a flowchart of an inventive method for generating a filtered activity pattern based on a first activity pattern at an auditory model of a first ear and a second activity pattern at an auditory model of a second ear. The method according to FIG. 12 is designated by 1200 in its entirety.

In a first step 1210, the method 1200 includes identifying a first trajectory in the first activity pattern and a second trajectory in the second activity pattern, which are associated with the same sound event.

In a second step 1220, the method 1200 includes determining whether the two trajectories are associated with a sound event of a useful sound source.

In a third step 1230 the method 1200 further includes filtering the first activity pattern or the second activity pattern based on a result of the determination whether a trajectory is associated with a sound event of the useful sound source, so that in a filtered activity pattern activity events dominate which are associated with a sound event of the useful sound source or that activity events which are not associated with a sound event of the useful sound source are no longer contained in the filtered activity pattern.

Apart from that, it is to be noted that the method 1200 may be supplemented or extended by all those steps performed by the above described inventive devices.

Figure 13:
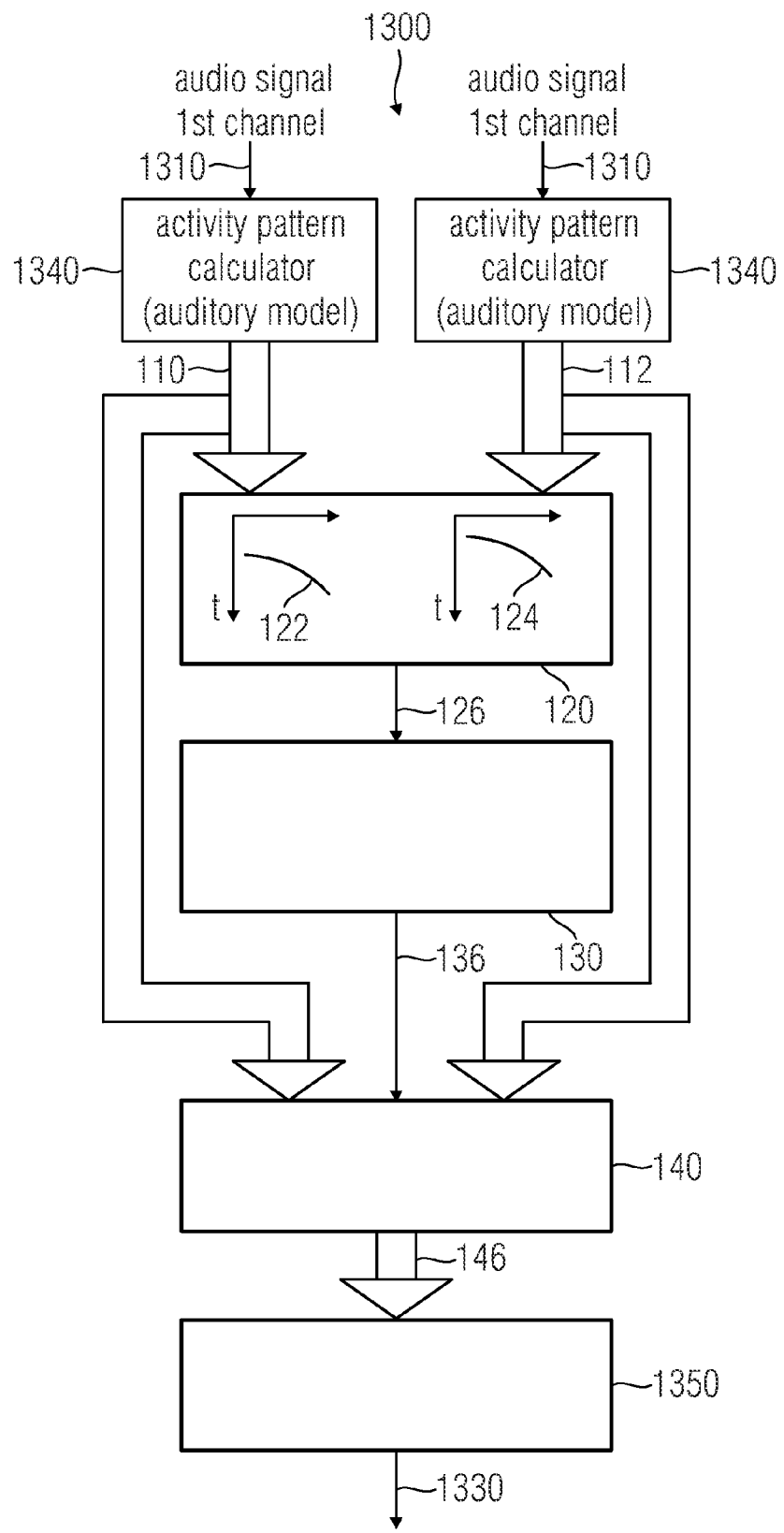
FIG. 13 shows a block diagram of an inventive source divider according to an embodiment of the present invention.

FIG. 13 shows a block diagram of an inventive source divider according to an embodiment of the present invention. The source divider of FIG. 13 is designated by 1300 in its entirety. The source divider 1300 is implemented to receive the first channel 1310 of an at least two-channel audio signal. The source divider 1300 is further implemented to receive a second channel 1320 of the at least two-channel audio signal. The source divider 1300 is further implemented to provide a debugged audio signal 1330 based on the audio signal having at least two channels.

The source divider 1300 includes a first activity pattern calculator 1340 which is implemented to calculate a first activity pattern 110 based on the first channel 1310 of the audio signal. The activity pattern calculator 1340 here includes or uses, respectively, for example an auditory model of an ear. The source divider 1300 further includes a second activity pattern calculator 1342 which is implemented to calculate a second activity pattern 112 based on the first channel 1320 of the audio signal. For this purpose, the activity pattern calculator 1342 is, for example, implemented to apply an auditory model of one ear to the second channel 1320 of the audio signal to obtain the second activity pattern 112.

The source divider 1300, apart from that, includes an identifier 120, a determiner 130 and a filter 140, as was already described with reference to FIG. 1. The means of the source divider 1300 which correspond to the means of the device 100 are designated by the same reference numerals as in FIGS. 1 and 2 and are not explained again here. Rather, reference is made to the description with regard to FIGS. 1 and 2.

The source divider 1300, in addition to the means of the device 100, 200, includes a synthesizer 1350 which is implemented to receive the filtered activity pattern 146 and to generate the debugged audio signal 1330 based on the filtered activity pattern 146. For this purpose, the synthesizer is implemented to transform the debugged activity pattern 146 into a time representation, a frequency representation or a subband representation. In other words, the synthesizer 1350 is implemented to at least partially reverse the calculations performed in the determination of the activity pattern using the auditory model. In other words, the synthesizer 1350 is, for example, implemented to reconstruct the debugged audio signal as a time range audio signal based on an activity pattern representing a neurotransmitter vesicle occurrence. Alternatively, the synthesizer 1350 may also be implemented, for example, to transform a neural activity pattern into a time range audio signal. Instead of the time range representation of the audio signal, apart from that also a frequency range representation may be used, i.e. for example a representation of energies or complex amplitude values in a plurality of spectral ranges or as a representation in the form of a plurality of complex indicators in a plurality of frequency bands.

Thus, the source divider 1300 enables a source division using a multi-channel (at least two-channel) audio signal, wherein the source division takes place on the basis of a detection of trajectories belonging together in two activity patterns representing the two channels of the audio signal.

Figure 14:
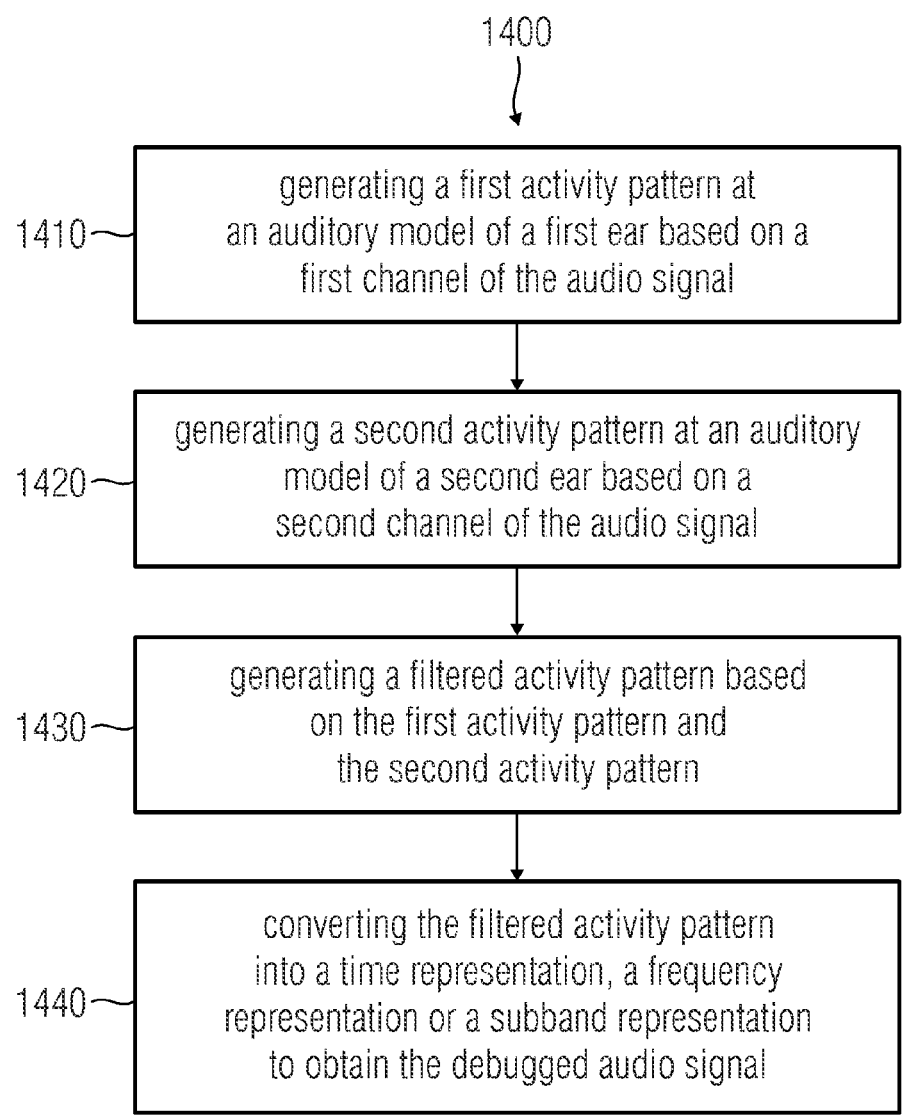
FIG. 14 shows a flowchart of an inventive method for generating a debugged audio signal according to an embodiment of the present invention.

FIG. 14 shows a flowchart of an inventive method for generating a debugged audio signal based on an audio signal having at least two channels. The method according to FIG. 14 is designated by 1400 in its entirety.

In a first step 1410, the method 1400 includes generating a first activity pattern at an auditory model of a first ear based on a first channel of the audio signal.

In a second step 1420, the method 1400 further includes generating a second activity pattern at an auditory model of a second ear based on a second channel of the audio signal.

In a third step 1430, the method 1400 further includes generating a filtered activity pattern based on the first activity pattern and the second activity pattern, as was already described with reference to FIGS. 1 and 2.

In a fourth step 1440, the method 1400 further includes converting the filtered activity pattern into a time representation, a frequency representation or a subband representation to obtain the debugged audio signal.

Apart from that, it is to be noted that the method 1400 may be extended by all those steps which are performed by the inventive devices described within the scope of the present application. Apart from that, it is to be noted that generating the filtered activity pattern based on the first activity pattern and the second activity pattern may, for example, take place using the method 1200 according to FIG. 12.

Figure 15:
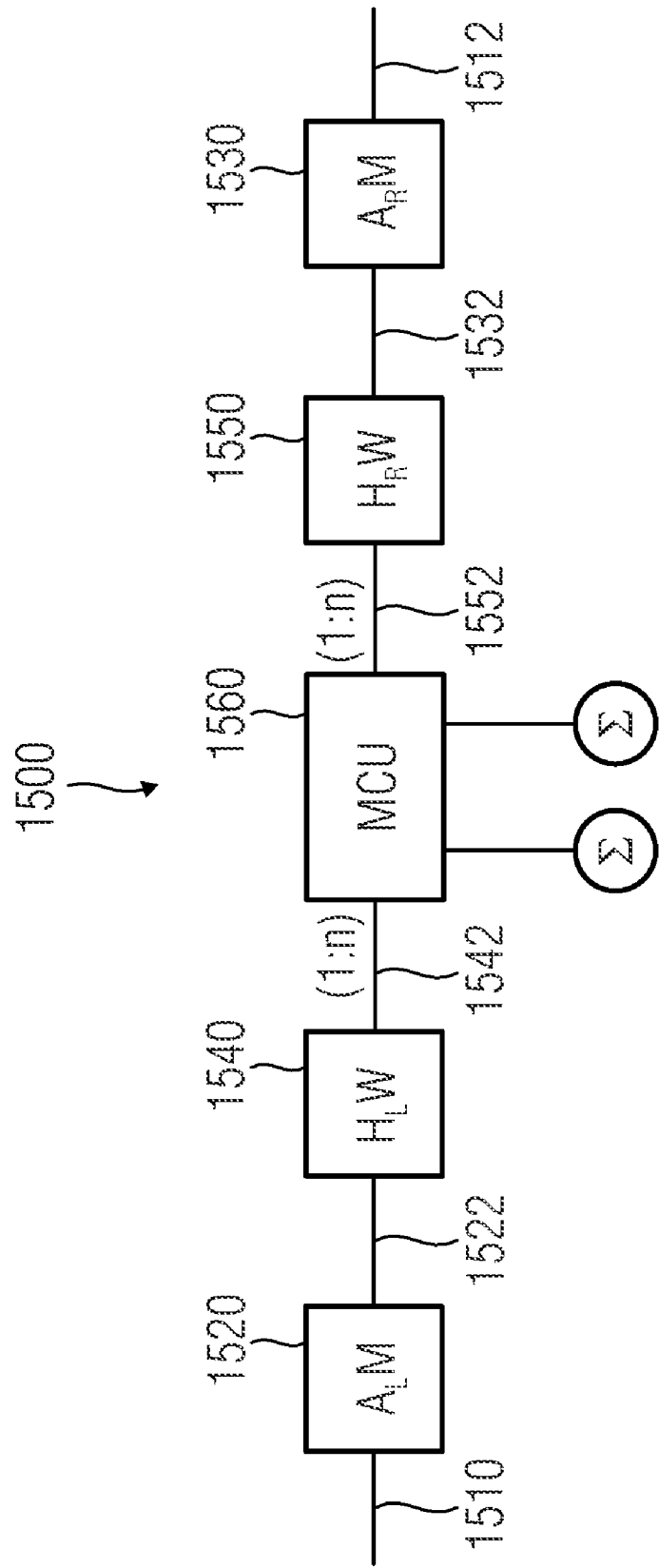
FIG. 15 shows an extract of a block diagram of an inventive device according to an embodiment of the present invention.

FIG. 15 also shows an extract from a block diagram of an inventive device for calculating a filtered activity pattern based on two audio signals. The device according to FIG. 15 is designated by 1500 in its entirety. The device 1500 is implemented to receive a first audio signal 1510 for example from a first microphone which is, for example, arranged in the vicinity of a first ear (for example of a human being). The device 1500 is further implemented to receive a second audio signal 1512 for example from a second microphone which is, for example, arranged in the vicinity of a second ear (for example a human ear). The device 1500 is further implemented, for example, to receive the first audio signal 1510 from a microphone arranged at the left side of a human head and to receive the second audio signal 1512 from a microphone arranged at the right side of a human head. The device 1500 further includes a first activity pattern calculator 1520 which is implemented to calculate a first activity pattern 1522 based on the first audio signal 1510, for example using an audio model. The device 1500 further includes a second activity pattern calculator 1530 which is implemented to calculate a second activity pattern 1532 based on the second audio signal 1512 using an auditory model. The device 1500 further includes a first Hubel-Wiesel network 1540 which is implemented to receive the first activity pattern 1522 and to generate a plurality of parallel signals 1542 based thereon which are implemented to indicate the presence of trajectories of different curvatures in the activity pattern 1522. In other words, the plurality of parallel signals 1542 are implemented to indicate when a trajectory with a curvature associated with a signal is present from a plurality of trajectories having different curvatures. The parallel lines 1542 here correspond to the signals 740, 742, 744, 746 of the device 700 with regard to their functioning and the first Hubel-Wiesel network 1540 corresponds to the first trajectory detector 730. The device 1500 further includes a second Hubel-Wiesel network 1550 which is implemented to generate a plurality of parallel signals 1552 based on the second activity pattern 1532. The parallel signals of the plurality 1542 of parallel signals here signalize the presence of a trajectory with a certain curvature in the second activity pattern 1532. With regard to the parallel lines of the plurality 1552 of parallel lines, what was said with regard to the plurality of parallel lines 1542 also applies. Further, the parallel lines 1552 correspond to the lines 750, 752, 754, 756 of the device 700 and the second Hubel-Wiesel network 1550 corresponds to the second trajectory detector 732 of the device 700.

The device 1500 further includes a multi-coincidence unit 1560 which is implemented to receive first input signals via the first plurality 1542 of parallel lines and to receive second input signals via the second plurality 1552 of parallel lines. Apart from that, it is to be noted that the multi-coincidence unit 1560 basically corresponds to the coincidence detector 770 of the device 700. It is to be noted that the multi-coincidence unit 1560 may, for example, be a multi-coincidence unit as was already described with regard to FIG. 5.

The multi-coincidence unit 1560 is thus implemented to determine, in connection with the Hubel-Wiesel networks 1540, 1550, whether trajectories of the same curvature are contained in the activity patterns 1522, 1532, and to further determine a time shift between the trajectories of the same curvature. The corresponding information may then be used to filter the first activity pattern 1522 and/or the second activity pattern 1532 to obtain a filtered activity pattern, as was already described above.

Figure 16:
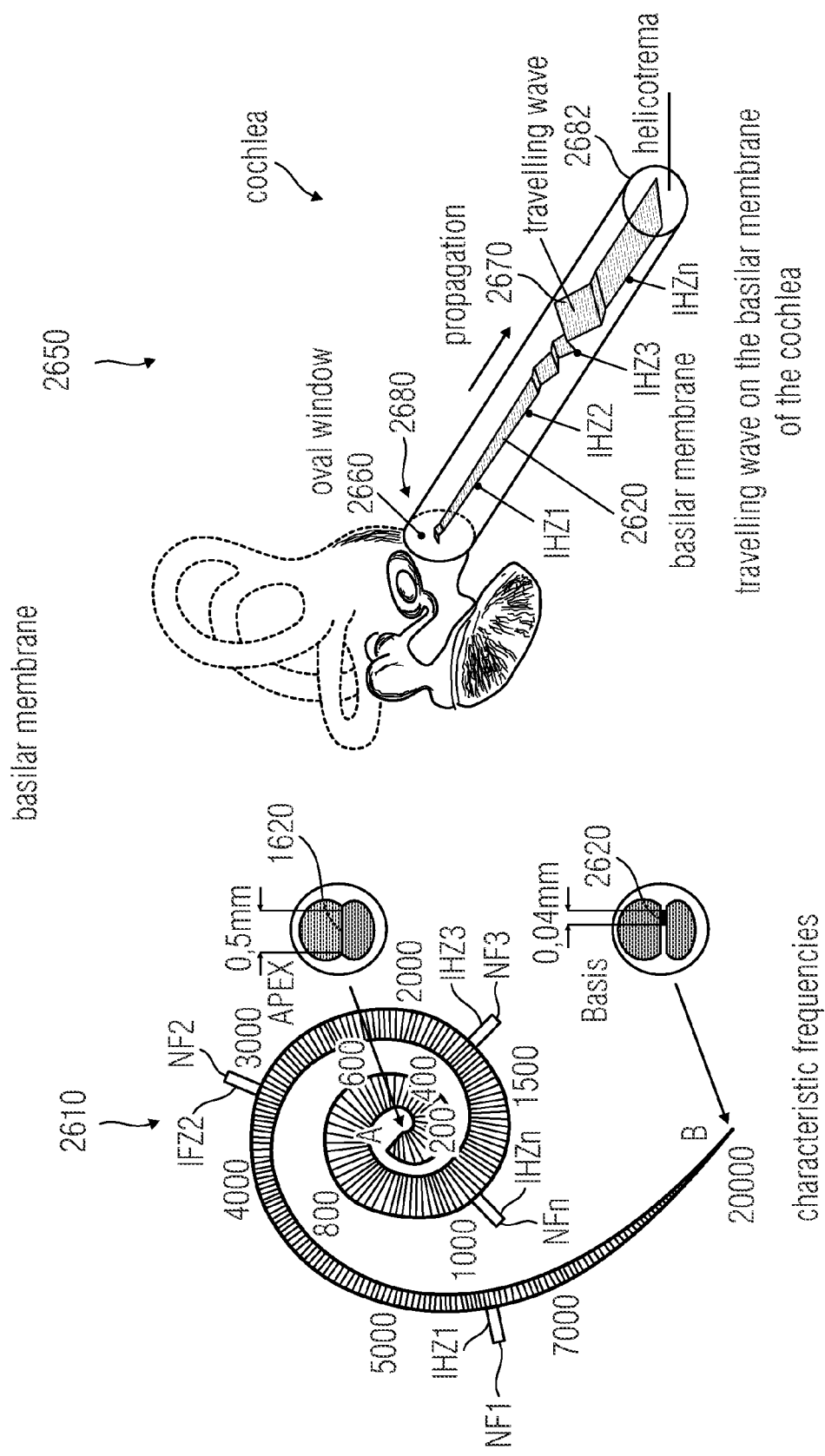
FIG. 16 shows a schematical illustration of a human cochlea and selected inner hair cells.

For reasons of clarity, FIG. 16 shows how the inner auditory cells or inner hair cells IHZ1, IHZ2, IHZ3, IHZ4, respectively, may be arranged along a basilar membrane.

For this purpose, FIG. 16 shows a graphical illustration of a geometry of the basilar membrane and a reaction of the basilar membrane to an excitation.

A first graphical illustration 2610 shows that the width of a basilar membrane 2620 increases from the base of the cochlea towards the end (apex) of the cochlea approximately by a factor of 10. Further, the graphical illustration 2610 shows different characteristic frequencies (in Hertz) with regard to which a maximum sensibility exists at different locations of the cochlea. In the proximity of the basis of the cochlea frequencies in a range of 20,000 Hertz are perceived to be strongest. Regarded from the base of the cochlea, the frequency for which a maximum sensibility results continuously decreases. The graphical illustration 610 further shows four exemplary inner hair cells IHZ1, IHZ2, IHZ3, IHZ4 which are arranged along the cochlea and which are coupled to the associated nerve fibers NF1, NF2, NF3, NFn. Assuming a sinusoidal excitation of the cochlea, for example the first inner hair cell IHZ1 responds most strongly to an excitation with a frequency of approx. 6,000 Hz. The second inner hair cell IHZ2, however, shows, for example, a maximum sensibility with an excitation with a frequency of approx. 3,300 Hz. Analog to that, the remaining inner hair cells IHZ3, IHZn comprise other frequencies of maximum sensibility.

A second graphical illustration 2650 further describes a coupling of an acoustic wave into the cochlea via an oval window 2660. The coupling via the oval window 2660 generates a traveling wave 2670 in the cochlea which runs from a base 2680 of the cochlea to an apex 2682 of the cochlea and thereby deflects the basilar membrane 2620. The nerve cells which are located closer to the base 2680 of the cochlea are excited earlier than the nerve cells located further away from the base 2680 of the cochlea. In other words, the location of the traveling wave 2670 as a function of time may be regarded as a trajectory of the traveling wave 2670. The trajectory may, of course, also be mapped to discrete nerve cells, so that a trajectory also describes in what temporal sequence several spatially separated nerve cells are excited by a traveling wave.

In the illustrated example, for example the inner hair cell IHZ1 is excited by the traveling wave 2670 earlier than the other inner hair cells IHZ2, IHZ3, IHZn. The first inner hair cell IHZ1 is closer to the oval window 2660, wherein the traveling wave 2670 propagates from the oval window (i.e. from the base 2680 of the cochlea) to the apex 2682 of the cochlea. Thus, one after the other the first inner hair cell IHZ1, the second inner hair cell IHZ2, the third inner hair cell IHZ3 and the $n^{th}$ inner hair cell IHZn are excited. In other words, one single traveling wave generates activity events at the illustrated inner hair cells in a time sequence, wherein the time distances are determined by the propagation speed of the traveling wave 2670 and the location of the corresponding inner hair cells IHZ1, IHZ2, IHZ3, IHZn. It is to be noted, however, that the activity events at the inner hair cells (considered in a two-dimensional illustration depending on the time and the index i of the inner hair cell IHZi) form a trajectory which, for example, corresponds to a temporal trajectory of a location of maximum deflection of the traveling wave 2670.

Further, the inventive methods, depending on the circumstances, may be implemented in hardware or in software. The implementation may be on a digital storage medium, for example a floppy disc, CD, DVD, ROM, PROM, EPROM, EEPROM or a flash storage medium having electronically readable control signals which may cooperate with a programmable computer system so that the corresponding method is performed. In general, the invention also consists in a computer program product having a program code stored on a machine-readable carrier for performing the inventive method, when the computer program product is executed on a computer. In other words, the invention may thus be realized as a computer program having a program code for performing the method, when the computer program is executed on a computer.

In summary it may be said that, within the scope of the present invention, delay trajectories (which, for example, result from the propagation of a traveling wave on a cochlea of an inner ear when the cochlea is excited by a sound event and which are reflected in activity patterns determined on the basis of the auditory model) run opposite to each other in a multi-coincidence unit (e.g. in a multi-coincidence unit 500 according to FIG. 5a). For this purpose, the multi-coincidence unit includes n anti-parallel delay paths of the length m, wherein n describes a number of inner hair cells (or nerve fibers) which are considered in a calculation of the activity pattern, and wherein m describes a number of bins and thus a maximum delay time and/or a maximum time resolution.

Within the scope of the present invention, two methods are of special advantage. Thus, for example activity patterns or activity events, respectively (e.g. vesicles) may be running directly opposite in the multi-coincidence unit (e.g. the multi-coincidence unit 500 according to FIG. 5a). Thereupon, a summation results (e.g. of multi-coincidence signals of coincidence outputs of coincidence cells 580) in integrator cells (or in summators 530, respectively). Each delay trajectory includes or comprises, respectively, for example n activity events or vesicles, respectively. Consequently, it is advantageous that each integrator (or summator 530, respectively) is provided with a threshold which is somewhat below m (e.g. at least 50% of n). The threshold is moreover represented in the block diagram according to FIG. 5a by the threshold value decider 540, wherein the following further applies: n=I. The integrators (or the summators 530, respectively) are further to be reset within an integration time of about 10 to 100 ms (to enable a reliable detection of individual trajectories and to prevent a mixing of coincidence events of different trajectories).

According to a further concept, it is possible to connect Hubel-Wiesel networks or Hough transformation networks, respectively, upstream from the multi-coincidence unit 500, as it is, for example, illustrated in FIG. 7. By this, the delay trajectories (in the activity patterns) are bent into a straight signal wave front. Detected delay trajectories are then matched in the multi-coincidence unit (e.g. in the coincidence detector 700). In other words it is detected in the coincidence detector 700, when trajectories or delay trajectories, respectively, exist in the activity patterns and further a time shift between the delay trajectories having the same curvature is determined.

The present invention thus provides a device for a binaural filtering of activity patterns or for a binaural vesicle filtering, respectively. Delay trajectories (in the activity patterns) are matched against each other by a time shift. Details with regard to that are, for example, contained in the U.S. Pat. No. 6,442,510 B1 whose teaching is hereby included herein by reference.

Further, a direct vesicle filtering with regard to one another takes place to determine coincidence pairs. Further, resulting from that, noise suppression or noise source suppression, respectively, or interference source suppression results by vesicles being raked out of noise sources (from the original activity patterns or from at least one of the original activity patterns, respectively).

Further, the present invention enables a precise clocking and synchronization of a left and a right cochlear implant, so that sound sources may be located in space with the right direction.

The present invention thus enables binaural noise source filtering, which makes it possible to reduce a cocktail party effect.

In summary, it may moreover be said that the present invention makes it possible to perform an angle determination of sound sources, for example by determining a time shift of trajectories belonging to the same sound event. It is further possible to select activity events or vesicles, respectively, (within the scope of filtering by the filter) depending on the sound source. In other words, depending on which sound source activity events or vesicles originate from, the activity events or vesicles, respectively, are taken over into the filtered activity pattern or the filtered activity patterns are attenuated or suppressed, respectively. This leads to a reduction of the cocktail party effect (for example for the carrier of a cochlear implant controlled using the filtered activity pattern), as in one embodiment of the present invention only sound sources from a certain direction (for example with regard to the patient with the cochlear implant) are reproduced.

Apart from that, it is to be noted that the inventive method brings special advantages when a cochlear implant is controlled by the filtered activity pattern (or, even better, by two filtered activity patterns, respectively). With a cochlear implant carrier, in some cases a binaural sound source location may no longer be performed by the brain. This is, for example, the case because the electrodes of the implants in both ears lie at different locations along the basilar membrane. Thus, an equal association to inner auditory cells or inner hair cells, respectively, is no longer possible.

An advantageous use of the inventive concept may further take place when outer hair cells are controlled afferently from an opposite ear (or an output of the multi-coincidence unit, respectively). Using this pre-calculated information, a cochlear implant may be assembled which excites intact outer hair cells in the same way, whereby a new generation of cochlear implants results.

In other words, the output or the output signals, respectively, of the multi-coincidence unit is an input variable for an efferent feedback control loop for controlling the outer motoric hair cells to selectively adjust a dynamic level range.

According to an embodiment of the present invention, an ear model is set up in pairs. Signals from inner auditory cells or inner hair cells, respectively, from the left and the right side are brought to coincidence in pairs in anti-parallel delay paths (circuit variant 1).

According to one aspect of the present invention, it must not be forgotten that the system is set up three times with separate signals from HSR, MSR and LSR spiral ganglion cells. As the same comprise a different response level range, the vesicle release is different for loud, medium and quiet tones. Thus, signal sources of different volumes may be separated.

The inventive concept serves to reduce a cocktail party effect by locating the sound sources by the inventive device or the inventive method, respectively. Thereupon vesicles belonging to a noise source (also to referred to as interfering sound source) (or belonging to an interfering sound source, respectively) are selectively filtered (or, respectively, filtered out or removed, respectively) (e.g. when generating the filtered activity pattern).

According to a further aspect of the present invention, moreover a Hubel-Wiesel network is connected upstream from the multi-coincidence unit.

According to a further aspect of the present invention, outputs of the multi-coincidence unit are supplied to a feedback circuit which innervates outer hair cells at the output by efferent connective traces. If the control circuit calculates a selective control signal from the input parameters, an action potential is triggered at the calculated efferent cell (or at the calculated efferent cells, respectively), and thus the outer hair cell is excited to contract. Thus, the supply of a stimulus from efferent neurons (or to efferent neurons, respectively, or using efferent neurons) to outer hair cells takes place.

The present invention thus provides a concept which may be used for the generation of a filtered activity pattern, wherein the filtered activity pattern may again be used advantageously for the control of a cochlear implant, so that the cocktail party effect which usually occurs is reduced for a cochlear implant carrier.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A device for generating a filtered activity pattern based on a first activity pattern at an auditory model of a first ear and a second activity pattern at an auditory model of a second ear, comprising:
    an identifier for identifying a first trajectory in a first activity pattern and a second trajectory in the second activity pattern, associated with the same sound event;
    a determiner for determining whether the two trajectories are associated with a sound event of a useful sound source; and
    a filter for filtering the first activity pattern or the second activity pattern based on a result of the determination whether a trajectory is associated with a sound event of the useful sound source, so that in a filtered activity pattern activity events dominate which are associated with a sound event of the useful sound source, or that the activity events not associated with a sound event of the useful sound source are no longer present in the filtered activity pattern;
    wherein the first activity pattern is based on a first audio signal processed by the auditory model of the first ear, and wherein the second activity pattern is based on a second audio signal processed by the auditory model of the second ear,
    wherein the first activity pattern and the second activity pattern describe two audio signals from different audio signal sources or audio signals from two channels of a multi-channel audio signal,
    wherein a trajectory in the activity pattern describes activity events in the activity pattern belonging together associated with a traveling wave on a basilar membrane of the ear model;
    wherein the identifier is implemented to identify a first curved trajectory in the first activity pattern and a second curved trajectory in the second activity pattern as trajectories belonging to the same sound event, when the first trajectory and the second trajectory comprise the same curvature within a predetermined tolerance range, and when the first trajectory and the second trajectory occur within a predetermined maximum time range;
    wherein the identifier is implemented to determine a time shift between the two identified trajectories which are associated with the same sound event; and
    wherein the determiner is implemented to determine using the time shift whether the two identified trajectories which are associated with the same sound event are associated with a sound event of a useful sound source.

2. The device according to claim 1, wherein the first ear is a left ear and wherein the second ear is a right ear or vice versa,
    wherein the first activity pattern is based on a first audio signal processed by the auditory model of the first ear, and wherein the second activity pattern is based on a second audio signal processed by the auditory model of the second ear,
    wherein the first audio signal describes an audio signal which may be perceived in an environment of the first ear and wherein the second audio signal describes an audio signal which may be perceived in an environment of the second ear.

3. The device according to claim 1, wherein the first activity pattern is a neural activity pattern over time at a plurality of nerve fibers of the auditory model of the first ear describing a reaction on the plurality of nerve fibers in the presence of a first audio signal at the first ear, wherein the second activity pattern is a neural activity pattern over time at a plurality of nerve fibers of the auditory model of the second ear describing a reaction on the plurality of nerve fibers in the presence of a second audio signal at the second ear, and
    wherein the activity pattern is a filtered neural activity pattern.

4. The device according to claim 3, wherein the neural activity pattern describes an activity of a plurality of nerve fibers of the ear model.

5. The device according to claim 3, wherein a trajectory comprises activity impulses on different nerve fibers based on the same event in the audio signal.

6. The device according to claim 1, wherein an activity event is an occurrence of an activity impulse on a nerve fiber.

7. The device according to claim 1, wherein the first activity pattern is a neurotransmitter vesicle occurrence at inner auditory cells of the auditory model of the first ear describing a reaction when a first audio signal is present at the first ear,
    wherein the second activity pattern is a neurotransmitter vesicle occurrence at inner auditory cells of the auditory model of the second ear describing a reaction to a presence of a second audio signal at the second ear, and wherein the filtered activity pattern is a filtered neurotransmitter vesicle occurrence.

8. The device according to claim 7, wherein a trajectory comprises a neurotransmitter vesicle occurrence in or at a plurality of inner auditory cells based on the same event in the audio signal.

9. The device according to claim 1, wherein an activity pattern is a neurotransmitter vesicle occurrence in or at an inner auditory cell.

10. The device according to claim 1, wherein the identifier is implemented to identify a first trajectory in the first activity pattern and a second trajectory in the second activity pattern as trajectories belonging to the same sound event, when the first trajectory and the second trajectory comprise the same length within a predetermined tolerance range, and when the first trajectory and the second trajectory occur within a predetermined maximum time range.

11. The device according to claim 1, wherein the identifier is implemented to determine a time shift between the two identified trajectories associated with the same sound event, and wherein the determiner is implemented to indicate that the two identified trajectories are associated with a sound event of the useful sound source when a time shift between the two identified trajectories lies within a firmly predetermined or settable range, and to otherwise indicate that the two identified trajectories are not associated with a sound event of the useful sound source.

12. The device according to claim 11, wherein the firmly predetermined or settable range comprises a time shift of zero.

13. The device according to claim 11, wherein the device further comprises a range setter which is implemented to set the settable range such that two trajectories belonging to the same sound event whose intensity is greater than a predetermined intensity threshold value comprise a time shift within the settable range, and that two trajectories belonging to the same sound event whose intensity is lower than the predetermined intensity threshold value comprise a time shift outside the selected range.

14. The device according to claim 11, wherein the device further comprises a range setter which is implemented to receive information describing an occurrence of trajectories for different time shifts between two trajectories which are associated with the same sound event,
to determine a time pattern or statistics for at least two ranges of time shifts in order to thus describe an occurrence of trajectories for the at least two ranges of time shifts, and
to set the settable range based on the time pattern or the statistics.

15. The device according to claim 11, wherein the device further comprises a range setter which is implemented to set the settable range based on an analysis of the first activity pattern or the second activity pattern so that trajectories belonging to a voice signal or a music signal comprise a time shift within the set range in the first activity pattern and in the second activity pattern.

16. The device according to claim 1, wherein the first activity pattern is a two-dimensional pattern which is described by time courses of signals in a first plurality of signals, wherein the signals of the first plurality of signals are associated with different auditory nerves or inner auditory cells of the auditory model of the first ear, and wherein the time courses of the signals of the first plurality of signals describe courses of a characteristic variable at the auditory nerves or at the inner auditory cells or in the inner auditory cells of the auditory model of the first ear;
wherein the second activity pattern is a two-dimensional pattern which is described by the time courses of signals of a second plurality of signals, wherein the signals of the second plurality of signals are associated with different auditory nerves or inner auditory cells of the auditory model of the second ear, and wherein the time courses of the signals of the first plurality of signals describe courses of a characteristic variable at the auditory nerves or at the inner auditory cells or in the inner auditory cells of the auditory model of the second ear.

17. The device according to claim 16, wherein the identifier is implemented to detect trajectories of at least approximately the same curvature in the first activity pattern and in the second activity pattern,
wherein the identifier is implemented to shift the first activity pattern and the second activity pattern against each other with regard to a time direction to detect locations in which the first activity pattern and the second activity pattern comprise coincidences for different shift states, and to decide, based on the locations of the coincidences detected for the different shift states, whether a trajectory in the first activity pattern and a trajectory in the second activity pattern comprise the same curvature and, if so, to detect, based on the detected locations of the coincidences, a time shift of the trajectories in the first activity pattern and the trajectories in the second activity pattern.

18. The device according to claim 16, wherein the identifier comprises an activity pattern shifter which is implemented to receive the first activity pattern in parallel in the form of a plurality of parallel time signals and to shift the same in a clocked or time-continuous way in a first direction, and which is further implemented to receive the second activity pattern in parallel in the form of a plurality of parallel time signals and to shift the same in a clocked or time-continuous way in a second direction which is opposite to the first direction,
wherein the activity pattern shifter comprises a first plurality of parallel branches which are implemented to shift the first activity pattern, and wherein the activity pattern shifter further comprises a second plurality of parallel branches which are implemented to shift the second activity pattern,
wherein an allocation between a branch of the first plurality of parallel branches and a branch of the second plurality of parallel branches exists,
wherein an allocation between individual positions along a first considered branch of the first plurality of parallel branches and positions along an associated second considered branch of the second plurality of parallel branches exists, such, that an activity event supplied to the first considered branch runs through the associated positions in the course of time in a first sequence, and that an activity event supplied to the second considered branch runs through the associated positions in the course of the time in a second sequence which is opposite to the first sequence,
wherein the identifier further comprises a coincidence detector which is implemented to detect, for a plurality of associated parallel branches and for a plurality of associated positions within the associated parallel branches, when two activity events simultaneously exist at two associated positions, and
wherein the identifier further comprises an evaluator which is implemented to detect, based on the information provided by the coincidence detector, when two trajectories associated with the same sound event are comprised in the first activity pattern and in the second activity pattern.

19. The device according to claim 18, wherein the evaluator is implemented to separately determine for a plurality of positions in the shifting direction of the activity patterns, how many coincidences of activity events in the first activity pattern and activity events in the second activity pattern occurred for a plurality of associated parallel branches in a predetermined time range overall, in order to identify a first trajectory in the first activity pattern and a second trajectory in the second activity pattern based thereon, which are associated with the same sound event, and to further determine a time shift between the two trajectories associated with the same sound event.

20. The device according to claim 18, wherein the identifier is implemented to detect, based on information as to how many coincidences of activity events occurred all in all in the first activity pattern and in the second activity pattern for a plurality of associated parallel branches at a considered position along the shifting direction of the activity patterns in a predetermined time range, that a first trajectory and a second trajectory associated with the same sound event exist in the first activity pattern and in the second activity pattern, when the numerical information indicates an occurrence of at least a predetermined minimum number of coincidences, and to determine, based on the considered position along the shifting direction of the activity patterns, the time shift between the two trajectories which are associated with the same sound event.

21. The device according to claim 16, wherein the identifier comprises a trajectory detector and is further implemented to supply the first activity pattern and the second activity pattern to the trajectory detector,
wherein the trajectory detector is implemented to provide information about a trajectory detected in the first activity pattern based on the first activity pattern, wherein the information about the trajectory detected in the first activity pattern describes a temporal position and a curvature of the detected trajectory;
wherein the trajectory detector is further implemented to provide information about a trajectory detected in the second activity pattern based on the second activity pattern, wherein the information about the trajectory detected in the second activity pattern describes a temporal position and a curvature of the detected trajectory;
wherein the identifier is implemented to determine, based on the information about the trajectory detected in the first activity pattern and the information about the trajectory detected in the second activity pattern, whether the first detected trajectory and the second detected trajectory are associated with the same sound event; and
wherein the identifier is further implemented to determine a time shift of the first detected trajectory and the second detected trajectory based on the information about the trajectory detected in the first activity pattern and the trajectory detected in the second activity pattern.

22. The device according to claim 21, wherein the trajectory detector is implemented to generate a first plurality of parallel output signals based on the first activity pattern,
wherein the trajectory detector is implemented to activate at least one output signal from the first plurality of output signals in the presence of a trajectory in the first activity pattern depending on a curvature of the trajectory in the first activity pattern, so that the activated output signal carries information about the curvature of the trajectory in the first activity pattern and about a point in time at which the trajectory occurs;
wherein the trajectory detector is implemented to generate a second plurality of parallel output signals based on the second activity pattern;
wherein the trajectory detector is implemented to activate at least one output signal from the second plurality of output signals in the presence of a trajectory in the second activity pattern depending on a curvature of the trajectory in the second activity pattern, so that the activated output signal carries information about the curvature of the trajectory in the first activity pattern and about a point in time at which the trajectory occurs.

23. The device according to claim 22, wherein the trajectory detector is implemented to perform a parallel Hough transformation to acquire the first plurality of parallel output signals and the second plurality of parallel output signals.

24. The device according to claim 22, wherein the identifier comprises a coincidence unit which is implemented to receive the output signals of the first plurality of output signals as a first curvature/time pattern and to receive the output signals of the second plurality of output signals as a second curvature/time pattern, to shift the first curvature/time pattern and the second curvature/time pattern with regard to a time direction opposite to each other in order to detect locations in which the first curvature/time pattern and the second curvature/time pattern coincide for different shifting states, and to determine, based on the coincidence locations detected for the different shifting states, whether a trajectory in the first activity pattern and in the second activity pattern comprise the same curvature, and, if so, to determine, based on the detected coincidence locations, a time shift of the first trajectory in the first activity pattern and the second trajectory in the second activity pattern.

25. The device according to claim 16, wherein the identifier comprises a shifter which is implemented to shift the first activity pattern and the second activity pattern in parallel in opposite directions through a field of shift register cells,
wherein the field of shift register cells comprises a plurality of lines and a plurality of columns;
wherein the field of shift register cells is implemented to receive the first activity pattern as a plurality of parallel line signals as the input signal of a first column and to receive the second activity pattern as a plurality of parallel line signals as the input signal of a last column;
wherein a shift register cell in a considered line and in a considered column is implemented to store an information value of the first activity pattern which may take on an active state and an inactive state and an information value of the second activity pattern which may take on an active state and an inactive state, to pass on the information value belonging to the first activity pattern to an adjacent shift register cell of the considered line and a first adjacent column, and to pass on the information value belonging to the second activity pattern to an adjacent shift register cell of the considered line and a second adjacent column;
wherein a shift register cell is further implemented to detect a coincidence event when information values present in the shift register cell and belonging to the first activity pattern and the second activity pattern simultaneously indicate an active state; and
wherein the identifier is further implemented to separately determine for the plurality of columns how many coincidence events occurred within a predetermined time interval in a considered column and to determine, based thereon, whether, and, if so, with what time shift trajectories occurred in the activity patterns associated with the same sound event.

26. The device according to claim 25, wherein the first identifier comprises a plurality of counters, adders or integrators which are associated with columns of the field and which are implemented to determine how many coincidence events occurred in the considered time interval in the columns.

27. The device according to claim 21, wherein the trajectory detector comprises a recognizer for pattern recognition which is implemented to detect a straight or curved line-shaped pattern as a trajectory in a two-dimensional illustration which is formed by the activity pattern over time, to determine the temporal position of the trajectory and to provide time information belonging to the trajectory.

28. The device according to claim 27, wherein the recognizer for pattern recognition is further implemented to provide information about the length of the trajectory.

29. The device according to claim 27, wherein the recognizer for pattern recognition is implemented to detect a straight or hyperbolically curved trajectory.

30. The device according to claim 27, wherein the recognizer for pattern recognition comprises a comparator for pattern comparison which is implemented to compare a two-dimensional illustration describing the activity pattern over time to at least one comparison pattern, to detect a trajectory and to acquire time information describing a temporal position of the trajectory.

31. The device according to claim 30, wherein the comparison pattern comprises a straight or hyperbolic curve.

32. The device according to claim 27, wherein the recognizer for pattern recognition is implemented to distort a two-dimensional illustration of the activity pattern over time step by step to acquire a distorted two-dimensional illustration of the activity pattern over time and to detect, when in the distorted two-dimensional illustration of the activity pattern over time an approximately straight line is comprised, to detect the approximately straight line as a trajectory, to determine the temporal position of the trajectory and to provide the time information belonging to the trajectory.

33. The device according to claim 32, wherein the recognizer for pattern recognition is implemented to distort the two-dimensional illustration of the neural activity pattern over time step by step such that a curved trajectory is bent to be straight step by step in the neural activity pattern by distorting step by step, wherein a plurality of distortion steps which are needed for bending the curved trajectory to be straight depend on a curvature of the curved trajectory, and wherein a number of the distortion steps which are needed for bending the curved trajectory to be straight comprises an indication about an original form of the trajectory.

34. The device according to claim 27, wherein the recognizer for pattern recognition comprises a curve recognizer which is implemented to receive the neural activity pattern in the form of a plurality of signals in parallel to pass on the signals at different speeds in parallel through a plurality of series-connected stages, wherein at least one predetermined stage comprises a threshold detector which is implemented to detect when at least a predetermined number of signals are active simultaneously in the predetermined stage.

35. The device according to claim 34, wherein at least one stage is implemented to delay several signals to a different degree when passing them on through the stage.

36. The device according to claim 1, wherein the device is implemented to transmit the filtered activity pattern or a signal derived therefrom to a cochlear implant.

37. The device according to claim 1, wherein the device is implemented to couple the filtered activity pattern or a signal derived therefrom to human or animal auditory cells or auditory nerves.

38. The device according to claim 1, wherein the filter is implemented to acquire the filtered activity pattern from the first activity pattern or from the second activity pattern by attenuating or removing activity events which are not associated with a sound event of the useful sound source.

39. The device according to claim 1, wherein the filter is implemented to acquire the filtered activity pattern from the first activity pattern or from the second activity pattern by taking over activity events into the filtered activity pattern which are associated with a sound event of the useful sound source.

40. The device according to claim 1, wherein the filter is implemented to identify or to mark activity events belonging to trajectories based on the event of the determiner which indicates when two trajectories are associated with the sound event of the useful sound source and to acquire the filtered activity pattern based on the identified or marked activity events.

41. The device according to claim 1, wherein the filter is implemented to filter the first activity pattern or the second activity pattern based on the result of the determiner whether a trajectory is associated with a sound event of the useful sound source to acquire a second filtered activity pattern so that in the second filtered activity pattern activity events dominate which are associated with a sound event of the useful sound source or that activity events not associated with a sound event of the useful sound source are no longer present in the filtered activity pattern,
   so that all in all two filtered activity patterns result, one of which is based on the first activity pattern and a further one of which is based on the second activity pattern.

42. The device according to claim 1, wherein the device is implemented to receive an activity pattern in or at inner auditory cells of a first response sensibility at the auditory model of the first ear as the first activity pattern and to receive an activity pattern in or at inner auditory cells of the first response sensibility at the auditory model of the second ear as the second activity pattern,
   to receive a third activity pattern in or at inner auditory cells of a second response sensibility at the auditory model of the first ear and to receive a fourth activity pattern in or at inner auditory cells of the second response sensibility at the auditory model of the second ear,
   wherein the identifier is implemented to identify a third trajectory in the third activity pattern and a fourth trajectory in the fourth activity pattern which are associated with the same sound event;
   wherein the determiner is implemented to determine whether the first trajectory, the second trajectory, the third trajectory and the fourth trajectory are associated with a sound event of a useful sound source,
   wherein the determiner is implemented to determine volume information for the trajectories and thus for the activity events associated with the trajectories based on the result of a comparison whether in the first activity pattern and in the third activity pattern within a predetermined temporal tolerance range trajectories of the same curvature within a predetermined curvature tolerance range exist,
   and to determine information whether the identified trajectories are associated with a useful sound event based on said volume information.

43. The device according to claim 42, wherein the filter is implemented to filter the first activity pattern, the second activity pattern, the third activity pattern or the fourth activity pattern using the volume information or information derived from the volume information with regard to whether the trajectories are associated with the useful sound event in order to acquire the filtered activity pattern, so that in the filtered activity pattern activity events whose associated volume information lies within a predetermined volume range dominate with regard to activity events whose volume information lies outside the predetermined volume range, or so that in the filtered activity pattern activity events whose volume information lies outside the predetermined volume range is no longer present.

44. The device according to claim 42, wherein the device is implemented to receive a fifth activity pattern in or at inner auditory cells of a third response sensibility at the auditory model of the first ear and to receive a sixth activity pattern in or at inner auditory cells of a third response sensibility at the auditory model of the second ear, wherein the determiner is implemented to determine volume information for the trajectories and thus for the activity events associated with the trajectories based on the result of a comparison whether in the first activity pattern and in the third activity pattern within a predetermined temporal tolerance range trajectories comprising the same curvature within a predetermined curvature tolerance range exist, and whether in the third activity pattern and in the fifth activity pattern within a predetermined temporal tolerance range trajectories comprising the same curvature within a predetermined curvature tolerance range exist.

45. The device according to claim 42, wherein the inner auditory cells of the first response sensibility comprise auditory cells of a low spontaneous emission rate, auditory cells of a medium spontaneous emission rate or auditory cells of a high spontaneous emission rate, wherein the inner auditory cells of the second response sensibility comprise auditory cells of a low spontaneous emission rate, auditory cells of a medium spontaneous emission rate or auditory cells of a high spontaneous emission rate, wherein the inner auditory cells of the third response sensibility comprise auditory cells of a low spontaneous emission rate, auditory cells of a medium spontaneous emission rate or auditory cells of a high spontaneous emission rate, and wherein the first response sensibility, the second response sensibility and the third response sensibility are different to each other.

46. The device according to claim 1, further including a feedback circuit, wherein the feedback circuit is implemented to receive output signals from a multi-coincidence unit and to provide control signals for outer hair cells based on the output signals of the multi-coincidence unit.

47. A source divider for generating a debugged audio signal based on an audio signal comprising at least two channels, comprising:

an activity pattern generator for generating a first activity pattern at an auditory model of a first ear based on a first channel of the audio signal and for generating a second activity pattern at an auditory model of a second ear based on a second channel of the audio signal;

a device for generating a filtered activity pattern based on the first activity pattern and the second activity pattern for generating a filtered activity pattern based on a first activity pattern at an auditory model of a first ear and a second activity pattern at an auditory model of a second ear, comprising:

an identifier for identifying a first trajectory in a first activity pattern and a second trajectory in the second activity pattern, associated with the same sound event;

a determiner for determining whether the two trajectories are associated with a sound event of a useful sound source; and a filter for filtering the first activity pattern or the second activity pattern based on a result of the determination whether a trajectory is associated with a sound event of the useful sound source, so that in a filtered activity pattern activity events dominate which are associated with a sound event of the useful sound source, or that the activity events not associated with a sound event of the useful sound source are no longer present in the filtered activity pattern;

wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model;

wherein the identifier is implemented to identify a first curved trajectory in the first activity pattern and a second curved trajectory in the second activity pattern as trajectories belonging to the same sound event, when the first trajectory and the second trajectory comprise the same curvature within a predetermined tolerance range, and when the first trajectory and the second trajectory occur within a predetermined maximum time range;

wherein the identifier is implemented to determine a time shift between the two identified trajectories which are associated with the same sound event; and wherein the determiner is implemented to determine using the time shift whether the two identified trajectories which are associated with the same sound event are associated with a sound event of a useful sound source; and a synthesizer for converting the filtered activity pattern into a time illustration, a frequency illustration or a subband illustration to acquire the debugged audio signal.

48. A method for generating a filtered activity pattern based on a first activity pattern at an auditory model of a first ear and a second activity pattern at an auditory model of a second ear, comprising:

identifying a first trajectory in the first activity pattern and a second trajectory in the second activity pattern, which are associated with the same sound events;

determining a time shift between the two identified trajectories associated with the same sound event;

determining whether the two trajectories are associated with a sound event of a useful sound source; and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern;

wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model;

wherein identifying a first trajectory and a second curved trajectory comprises identifying a first curved trajectory in the first activity pattern and a second curved trajectory in the second activity pattern as trajectories belonging to the same sound event, when the first trajectory and the second trajectory comprise the same curvature within a predetermined tolerance range; and wherein determining whether the two identified trajectories are associated with a sound event of a useful sound source is executed using the time shift.

49. A method for generating a debugged audio signal based on an audio signal comprising at least two channels, comprising:

generating a first activity pattern at an auditory model of a first ear based on a first channel of the audio signal and generating a second activity pattern at an auditory model of a second ear based on a second channel of the audio signal;

generating a filtered activity pattern based on the first activity pattern and the second activity pattern according to a method for generating a filtered activity pattern based on a first activity pattern at an auditory model of a first ear and a second activity pattern at an auditory model of a second ear, comprising:

identifying a first trajectory in the first activity pattern and a second trajectory in the second activity pattern, which are associated with the same sound events;

determining a time shift between the two identified trajectories associated with the same sound event;

determining whether the two trajectories are associated with a sound event of a useful sound source; and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern;

wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model;

wherein identifying a first trajectory and a second curved trajectory comprises identifying a first curved trajectory in the first activity pattern and a second curved trajectory in the second activity pattern as trajectories belonging to the same sound event, when the first trajectory and the second trajectory comprise the same curvature within a predetermined tolerance range; and wherein determining whether the two identified trajectories are associated with a sound event of a useful sound source is executed using the time shift; and converting the filtered activity pattern into a time illustration, a frequency illustration or a subband illustration to acquire the debugged audio signal.

50. A non-transitory computer readable medium storing a computer program for performing, when the computer program is executed on a computer, a method for generating a filtered activity pattern based on a first activity pattern at an auditory model of a first ear and a second activity pattern at an auditory model of a second ear, the method comprising:

identifying a first trajectory in the first activity pattern and a second trajectory in the second activity pattern, which are associated with the same sound events;

determining a time shift between the two identified trajectories associated with the same sound event;

determining whether the two trajectories are associated with a sound event of a useful sound source; and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern;

wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model;

wherein identifying a first trajectory and a second curved trajectory comprises identifying a first curved trajectory in the first activity pattern and a second curved trajectory in the second activity pattern as trajectories belonging to the same sound event, when the first trajectory and the second trajectory comprise the same curvature within a predetermined tolerance range; and wherein determining whether the two identified trajectories are associated with a sound event of a useful sound source is executed using the time shift, when the computer program is executed on a computer.

51. A non-transitory computer readable medium storing a computer program for performing, when the computer program is executed on a computer, a method for generating a debugged audio signal based on an audio signal comprising at least two channels, the method comprising:

generating a first activity pattern at an auditory model of a first ear based on a first channel of the audio signal and generating a second activity pattern at an auditory model of a second ear based on a second channel of the audio signal;

generating a filtered activity pattern based on the first activity pattern and the second activity pattern according to a method for generating a filtered activity pattern based on a first activity pattern at an auditory model of a first ear and a second activity pattern at an auditory model of a second ear, comprising:

identifying a first trajectory in the first activity pattern and a second trajectory in the second activity pattern, which are associated with the same sound events;

determining a time shift between the two identified trajectories associated with the same sound event;

determining whether the two trajectories are associated with a sound event of a useful sound source; and filtering the first activity pattern or the second activity pattern based on a result of determining whether a trajectory is associated with a sound event of the useful sound source, so that in a filtered activity pattern activity events associated with a sound event of the useful sound source dominate with regard to activity events not associated with a sound event of the useful sound source, or that the activity events which are not associated with a sound event of the useful sound source no longer exist in the filtered activity pattern;

wherein the first activity pattern is based on a first audio signal processed by the auditory model of the first ear, and wherein the second activity pattern is based on a second audio signal processed by the auditory model of the second ear, wherein the first activity pattern and the second activity pattern describe two audio signals from different audio signal sources or audio signals from two channels of a multi-channel audio signal, wherein a trajectory in the activity pattern describes activity events in the activity pattern belonging together associated with a traveling wave on a basilar membrane of the ear model;

wherein identifying a first trajectory and a second curved trajectory comprises identifying a first curved trajectory in the first activity pattern and a second curved trajectory in the second activity pattern as trajectories belonging to the same sound event, when the first trajectory and the second trajectory comprise the same curvature within a predetermined tolerance range; and wherein determining whether the two identified trajectories are associated with a sound event of a useful sound source is executed using the time shift; and converting the filtered activity pattern into a time illustration, a frequency illustration or a subband illustration to acquire the debugged audio signal, when the computer program is executed on a computer.

* * * * *